(12) United States Patent
Hampapur et al.

(10) Patent No.: US 12,094,010 B1
(45) Date of Patent: Sep. 17, 2024

(54) INTELLIGENT AUTHORIZATION SYSTEM

(71) Applicant: Bloom Value Corporation, Norwalk, CT (US)

(72) Inventors: Arun Hampapur, Norwalk, CT (US); Sampoorna Hegde, Bengaluru (IN); Sharathchandra Pankanti, Darien, CT (US); Roona Shree, Bengaluru (IN); Priyanka Rajesh, Bengaluru (IN); Yashpal Gulab Dhawle, Bengaluru (IN); Moumita Dhar, Bengaluru (IN); Venu Kondle, Norwalk, CT (US)

(73) Assignee: Bloom Value Corporation, Norwalk, CT (US)

( * ) Notice: Subject to any disclaimer, the term of this patent is extended or adjusted under 35 U.S.C. 154(b) by 0 days.

(21) Appl. No.: 18/613,199

(22) Filed: Mar. 22, 2024

(51) Int. Cl.
*G06Q 40/08* (2012.01)
*G16H 40/20* (2018.01)

(52) U.S. Cl.
CPC ............. *G06Q 40/08* (2013.01); *G16H 40/20* (2018.01)

(58) Field of Classification Search
CPC ................................................ G06Q 50/20–26
See application file for complete search history.

(56) References Cited

U.S. PATENT DOCUMENTS

| | | | | |
|---|---|---|---|---|
| 11,860,852 | B1 * | 1/2024 | Harvey | G06Q 40/03 |
| 11,880,888 | B1 * | 1/2024 | Gold | G06Q 10/00 |
| 2020/0327988 | A1 * | 10/2020 | Borans | G06Q 40/08 |
| 2020/0410601 | A1 * | 12/2020 | Laumeyer | G06F 40/186 |
| 2021/0200896 | A1 * | 7/2021 | Lilja | G06F 21/6227 |
| 2021/0256615 | A1 * | 8/2021 | Hayward | G06N 3/08 |
| 2021/0335470 | A1 * | 10/2021 | Nambirajan | G06N 7/01 |

(Continued)

OTHER PUBLICATIONS (n.a.), "Weight (Artificial Neural Network)", 2022, DeepAI, all pages, https://web.archive.org/web/20221124132929/https://deepai.org/machine-learning-glossary-and-terms/weight-artificial-neural-network (Year: 2022).*

(Continued)

*Primary Examiner* — Christopher L Gilligan
*Assistant Examiner* — Jessica Marie Webb
(74) *Attorney, Agent, or Firm* — Kevin J Fournier Intellectual Property Legal Services Ltd.; Kevin J Fournier

(57) ABSTRACT

A system and method to authorize requests for procedures or medical claim requests is described. In one aspect, datasets from multiple data sources, including historical authorizations associated with various medical claims, are processed. The machine learning engines and the machine learning models are trained based on the received data. Simultaneously, real-time authorization requests are received and analyzed from secondary data sources. Each request is split into service requests based on second attributes, which include identifiers linked to services. The services are encoded using fixed-length encoding, and unique numeric identifiers are assigned to categorical variables. For each encoded service request, contexts, actions, and decisions are determined by comparing the first attributes of historical authorization requests with the second attributes of real-time requests. Service requests are then categorized into cohorts based on similarity metrics between their second attributes and those of historical authorizations. This comparison enables efficient processing and informed decision-making.

20 Claims, 27 Drawing Sheets

(56) References Cited

U.S. PATENT DOCUMENTS

| | | | | |
|---|---|---|---|---|
| 2021/0338387 A1* | 11/2021 | Inam | ............... | G06T 7/0012 |
| 2021/0343400 A1* | 11/2021 | Inam | ............... | G16H 40/67 |
| 2022/0309592 A1* | 9/2022 | Zahora | ............... | G06Q 10/10 |
| 2023/0084146 A1* | 3/2023 | Singh | ............... | G06Q 10/10 |
| | | | | 705/4 |
| 2023/0215549 A1* | 7/2023 | Kaneria | ............... | G16H 40/20 |
| | | | | 705/2 |
| 2023/0260638 A1* | 8/2023 | Hampapur | ............... | G16H 50/30 |
| | | | | 705/2 |
| 2023/0360778 A1* | 11/2023 | Cochran | ............... | G16H 40/20 |
| 2024/0135460 A1* | 4/2024 | Singh | ............... | G06Q 40/08 |

OTHER PUBLICATIONS

Veras Magalhaes Junior et al., "A Study of the Influence of Textual Features in Learning Medical Prior Authorization," 2019 IEEE 32nd Int'l Symposium on Computer-Based Medical Systems, Cordoba, Spain, 2019, pp. 56-61, doi: 10.1109/CBMS.2019.00021. (Year: 2019).*

Nian et al., Auto insurance fraud detection using unsupervised spectral ranking for anomaly, 2016, J Finance and Data Sci, vol. 2, Issue 1, pp. 58-75, https://doi.org/10.1016/j.jfds.2016.03.001 (Year: 2016).*

Peng et al., A machine learning approach to uncovering hidden utilization patterns of early childhood dental care among medicaid-insured children, 2021, Frontiers in Pub Health, vol. 8, all pages, https://www.frontiersin.org/journals/public-health/articles/10.3389/fpubh.2020.599187 (Year: 2021).*

* cited by examiner

| Auth# | Date | Age | Request1 (CPT1) | Request2 (CPT2) | Diagnosis1 (ICD1) | Diagnosis2 (ICD2) |
|---|---|---|---|---|---|---|
| | | | | | | |

FIG. 5

FIG. 6A (600A): Auth# | Date | Age | Request1 (CPT1) | Request2 (CPT3) | DIAGNOSIS1 (ICD2) | DIAGNOSIS2 (ICD4) | ...

FIG. 6B (600B): CPT1 | ICD2 | ICD4 | CPT1 | CPT3 | Date | Age | Auth# | ...

FIG. 6C (600C): CPT3 | ICD2 | ICD4 | CPT1 | CPT3 | Date | Age | Auth# | ...

*700A*

CPT CODE LIST      CPT CODE LIST - 2014 - 2015

| CPT CODE | DESCRIPTION OF SERVICE | FEE |
|---|---|---|
| | EYEBALL - REMOVAL OF EYE | |
| 65091 | EVISCERATION OF EYE, WITHOUT IMPLANT | 389.63 |
| 65093 | EVISCERATION OF EYE WITH IMPLANT | 388.84 |
| 65101 | ENUCLEATION WITHOUT IMPLANT | 448.91 |
| 65103 | ENUCLEATION W/IMPLANT, MUSCLES NOT ATTACHED | 469.19 |
| 65105 | ENUCLEATION W/IMPLANT, MUSCLES ATTACHED TO IMPLANT | 517.99 |
| 65110 | EXENTERATION OF ORBIT W/O SKIN GRAFT REM ORBIT CONTENT | 757.20 |
| 65112 | EXENTERATION, W/THERAPEUTIC REMOVAL OF BONE | 890.15 |
| 65114 | EXENTERATION, WITH MUSCLE OR MYOCUTANEOUS FLAP | 927.92 |
| | SECONDARY IMPLANT(S) PROCEDURES | |
| 65125 | MODIFICATION, OCULAR IMPLANT (SEPARATE PROCEDURE) | 275.36 |
| 65130 | EVISCERATION, EYE IMPLANTATION IN SCLERAL SHELL | 444.63 |
| 65135 | AFTER ENUCLEATION, MUSCLES NOT ATTACHED TO IMPLANT | 452.88 |
| 65140 | AFTER ENUCLEATION, MUSCLES ATTACHED TO IMPLANT | 493.55 |
| 65150 | REINSERTION/OCULAR IMPLANT W/WO | 356.78 |

FIG. 7A

| CODE | SHORT DESCRIPTION (VALID ICD-10 FY 2023) |
|---|---|
| A000 | Cholera due to Vibrio cholerae 01, biovar cholerae |
| A001 | Cholera due to Vibrio cholerae 01, biovar eltor |
| A009 | Cholera, unspecified |
| A0100 | Typhoid fever, unspecified |
| A0101 | Typhoid meningitis |
| A0102 | Typhoid fever with heart involvement |
| A0103 | Typhoid pneumonia |
| A0104 | Typhoid arthritis |
| A0105 | Typhoid osteomyelitis |
| A0109 | Typhoid fever with other complications |
| A011 | Paratyphoid fever A |
| A012 | Paratyphoid fever B |
| A013 | Paratyphoid fever C |
| A014 | Paratyphoid fever, unspecified |
| A020 | Salmonella enteritis |
| A021 | Salmonella sepsis |
| A0220 | Localized salmonella infection, unspecified |
| A0221 | Salmonella meningitis |
| A0222 | Salmonella pneumonia |
| A0223 | Salmonella arthritis |
| A0224 | Salmonella osteomyelitis |
| A0225 | Salmonella pyelonephritis |
| A0229 | Salmonella with other localized infection |
| A028 | Other specified salmonella infections |
| A029 | Salmonella infection, unspecified |
| A030 | Shigellosis due to Shigella dysenteriae |
| A031 | Shigellosis due to Shigella flexneri |
| A032 | Shigellosis due to Shigella boydii |
| A033 | Shigellosis due to Shigella sonnei |
| A038 | Other shigellosis |
| A039 | Shigellosis, unspecified |
| A040 | Enteropathogenic Escherichia coli infection |
| A041 | Enterotoxigenic Escherichia coli infection |
| A042 | Enteroinvasive Escherichia coli infection |
| A043 | Enterohemorrhagic Escherichia coli infection |
| A044 | Other intestinal Escherichia coli infection |
| A045 | Campylobacter enteritis |
| A046 | Enteritis due to Yersinia enterocolitica |
| A047 | Enterocolitis due to Clostridium difficile |
| A0471 | Enterocolitis due to Clostridium difficile, recurrent |
| A0472 | Enterocolitis d/t Clostridium difficile, not spcf as recur |
| A048 | Other specified bacterial intestinal infections |
| A049 | Bacterial intestinal infection, unspecified |
| A050 | Foodborne staphylococcal intoxication |
| A051 | Botulism food poisoning |

FIG. 8A

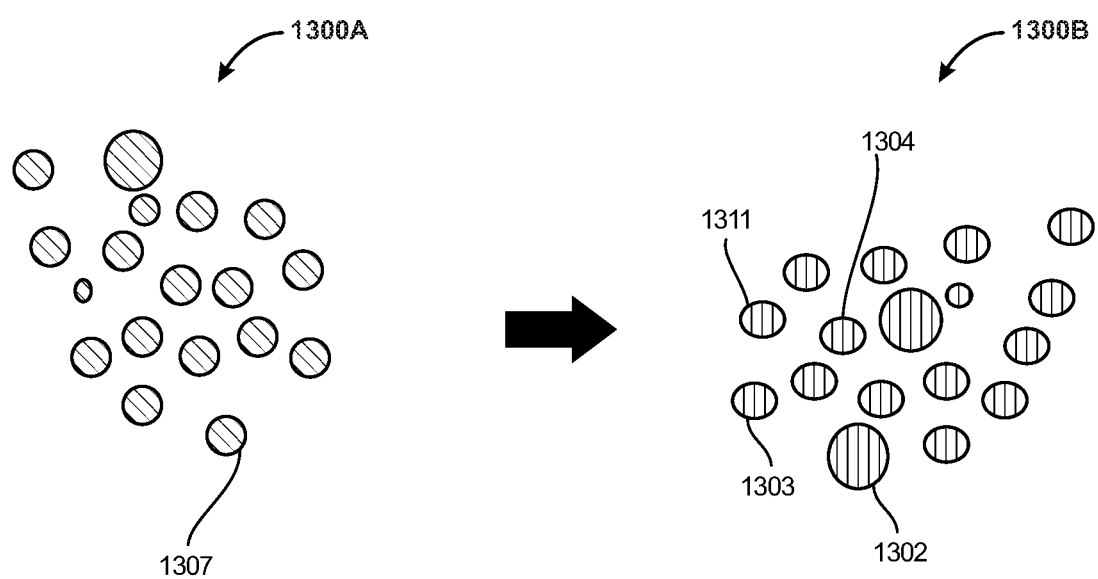
FIG. 13A        FIG. 13B

|  | CLASSIFIER APPROVE | CLASSIFIER REVIEW |
|---|---|---|
| TRUE APPROVE | 98 (1%)<br>994 (11%) | 8339 (93%)<br>7443 (82%) |
| TRUE DENY | 7 (0.07%)<br>55 (0.6%) | 505 (6%)<br>457 (5%) |

Approved Authorization Details — 1900

| CPT Code | CPT Code Desc | Auth No | Action | Speciality | Diagnosis Descriptions | Member ID | HP Group |
|---|---|---|---|---|---|---|---|
| 00120 | ANESTH EAR | 20230313T8800200 | Review | Interventional | Q899 CONGENITAL MALFORMATION, UNSPECIFIED:: | ID_Key_000000212415 | MEDI-CAL |
| 0055T | BONE SRGRY | 20230316T8800357 | Review | Orthopedic | M1711 UNILATERAL PRIMARY OSTEOARTHRITIS, RIGHT KNEE:: | ID_Key_000000198009 | MEDI-CAL |
| 00731 | ANES UPR GI | 20230313T8800024 | Review | Gastroenterolo | K2900 ACUTE GASTRITIS WITHOUT BLEEDING:: | ID_KEY_52071 | MEDI-CAL |
| 00731 | ANES UPR GI | 20230313T8800161 | Review | Hospital | K2080 OTHER ESOPHAGITIS WITHOUT BLEEDING:: | ID_KEY_31500 | MEDI-CAL |
| 00731 | ANES UPR GI | 20230313T8800360 | Review | Gastroenterolo | K219 GASTRO-ESOPHAGEAL REFLUX DISEASE WITHOUT ESOPHAGITIS:: | ID_KEY_87935 | MEDI-CAL |
| 00811 | ANES LWR | 20230313T8800182 | Review | Gastroenterolo | K5792 DIVERTICULITIS OF INTESTINE, PART UNSPECIFIED, WITHOUT PERFORATION OR ABSCESS WITHOUT BLEEDING:K625 HEMORRHAGE OF ANUS AND RECTUM: | ID_Key_000000211754 | MEDI-CAL |
| 00811 | ANES LWR | 20230316T8800379 | Review | Gastroenterolo | R195 OTHER FECAL ABNORMALITIES:IZ1211 ENCOUNTER FOR SCREENING FOR MALIGNANT NEOPLASM OF COLON: | ID_KEY_97100 | MEDICARE |
| 0121 | Medical/Surgic | 20221212T8800368 | Review | Hospital | M25579 PAIN IN UNSPECIFIED ANKLE AND JOINTS OF UNSPECIFIED FOOT:: | ID_KEY_106244 | MEDI-CAL |
| 0174 | Newborn-Level | 20230123T8800169 | Review | Hospital | P22 :: | ID_KEY_78582 | MEDI-CAL |
| 0550 | Skilled nursing | 20221115T8800302 | Review | Skilled Nursing | K5669 OTHER INTESTINAL OBSTRUCTION:: | ID_Key_000000172315 | MEDI-CAL |
| 0550 | Skilled nursing | 20221212T8800591 | Review | Skilled Nursing | R41 :: | ID_KEY_75142 | MEDI-CAL |
| 0550 | Skilled nursing | 20221214T8800300 | Review | Federally | I629 NONTRAUMATIC INTRACRANIAL HEMORRHAGE, UNSPECIFIED:: | ID_KEY_114029 | MEDI-CAL |
| 0550 | Skilled nursing | 20230316T8804459 | Review | Skilled Nursing | G70 :: | ID_Key_000000220086 | OTHER |
| 0658 | Hospice Room | 20230227T8800208 | Review | Hospice | I672 CEREBRAL ATHEROSCLEROSIS:: | ID_Key_000000220080 | MEDI-CAL |
| 0659 | Other hospice | 20230227T8800208 | Review | Hospice | I672 CEREBRAL ATHEROSCLEROSIS:: | ID_Key_000000220080 | MEDI-CAL |

FIG. 19

INTELLIGENT AUTHORIZATION SYSTEM

CROSS-REFERENCE

This application claims the benefit of an Indian provisional patent application filed on Mar. 25, 2023, in the Indian Patent Office and assigned an application Ser. No. 2023410020600, titled "INTELLIGENT AUTHORIZATION SYSTEM," which is hereby incorporated by reference in their entirety.

FIELD

Various embodiments of the disclosure relate to artificial intelligence-based intelligent authorization systems. More specifically, the intelligent authorization system may include multiple engines, models, frameworks, etc., that may execute operations independently or in cooperation to achieve specific outcomes or results.

BACKGROUND

The processing and authorization of medical claims have long been a complex and labor-intensive task in the healthcare industry. The current state of the art involves reviewing the medical claims, checking the dimensions of the claims, and adjudication of medical claims. However, when the volume or number of medical claims increases, the dimensions or parameters associated with the medical claims may increase, and the claim review and adjudication become overly complex, cumbersome, and time-consuming. The processes involved in the current state of the art are not only time-consuming but also prone to various inaccuracies, inconsistencies, and fraudulent activities. Further, processing medical claims using processes or techniques in the current state of the art may become cumbersome when the volume of medical claims increases, thereby leading to backlogs, delays, and suboptimal outcomes for both healthcare providers and patients.

The reliance on human judgment in the medical claim authorization process introduces several significant disadvantages. When claim requests are flagged for manual review, the approval process can be delayed, causing frustration for healthcare providers and potentially impacting patient care. Moreover, human reviewers are not immune to errors, biases, and oversights, which may cause inconsistent or incorrect claim decisions. The limited time and resources available to human reviewers may also prevent them from scrutinizing each claim's merits, leading to superficial evaluations based on incomplete information.

Another critical issue with the current state of the art is the need for comprehensive access to relevant information. This leads to a fragmented approach, resulting in inconsistent and inappropriate claim authorizations. The claim authorization process's manual nature makes it difficult to detect and prevent fraudulent activities. Unscrupulous actors may exploit the system's vulnerabilities, submitting false or inflated claims that may go unnoticed by human reviewers. The inability to identify and flag suspicious patterns or anomalies in claim requests leaves the healthcare system vulnerable to financial losses and may compromise the integrity of the medical claim ecosystem.

SUMMARY

A system and method for authorizing requests associated with medical claims are described. In an embodiment, the system and method implement steps that include a first dataset received from multiple first data sources. This dataset includes historical authorizations linked to one or more medical claims and one or more service requests that may need prior authorization, each historical authorization request consisting of several first attributes. Using multiple machine learning engines, multiple machine learning models are trained based on the received first dataset. This arrangement enables the system and method to learn patterns and trends from historical data, thereby improving its ability to make informed decisions regarding real-time authorization requests.

In an embodiment, a second dataset is obtained from multiple second data sources. This dataset includes real-time authorization requests related to one or more medical claims associated with various medical procedures, treatments, medications, hospital stays, or combinations thereof. Each authorization request includes several second attributes, such as identifiers linked to specific services. In an embodiment, the system and method process and analyze each authorization request by using multiple machine learning engines. By splitting each request into multiple service requests based on the second attribute and encoding each service request using a fixed-length encoding, unique numeric identifiers are assigned to categorical variables. For each encoded service request, contexts, actions, and decisions are identified or determined by applying the trained machine learning models that compare the first attributes associated with each authorization request with the second attributes associated with each authorization request in real-time.

In an embodiment, the service requests are then categorized into various cohorts by identifying or determining similarity metrics based on the first and second attributes. A distance function is applied to compute the distance metric between each service request and each historical authorization request, and the service requests are grouped accordingly based on the results. In an embodiment, the technical advantage of the above-described system and method is its ability to process large volumes of data efficiently, enabling real-time decision-making while also learning from past experiences. Additionally, by continuously retraining machine learning models based on new data, the system and method remain adaptive and responsive to changing conditions. Based on the analysis and processing, one or more outputs are generated and rendered on one or more UIs. For instance, one or more outputs (e.g., first output, second output, third output, etc.) may correspond to one or more authorization requests or service requests received in real-time are approved, rejected, or subjected to an audit for review or redirected to Medicaid or Medicare for further scrutiny. These authorizations correspond to the service requests within their respective cohorts. In response to one or more outputs, machine learning models are retrained using the machine learning engines. The system and method are adaptive and may learn from historical data while processing real-time requests, significantly enhancing the decision-making capabilities and improving overall medical claim authorization processes.

In an embodiment, the system and method may provide that one or more service requests are encoded using one-hot encoding. This enables efficient representation and processing of categorical data, improving the system and method's ability to handle complex requests and reducing computational complexity. The system and method may generate outputs that may be rendered on user interfaces. For example, the outputs may correspond to providing authorization requests or service requests based on multiple classifiers, including but not limited to eligibility, coverage, medical necessity, trust model, cost, or a combination thereof. This arrangement enhances the system and method's decision-making capabilities by considering multiple factors and improving overall accuracy and fairness in authorizing services.

In an embodiment, the system and method may provide the distance metric computed based on the distance function, for example, a triple distance metric, which enables more precise measurement of similarity between service requests and historical data, leading to better recommendations and improved user experience. The system and method may provide that in response to the execution of one or more operations, visualizations are generated or created and displayed on user interfaces. This enables users to easily understand the authorization requests and make informed decisions based on the presented information. This arrangement improves user engagement and satisfaction while reducing the need for extensive manual analysis.

In an embodiment, forecasts may be created or generated in real-time based on patterns associated with historical authorization requests, enabling the system and method to identify or determine trends and correlations between current and past data. This enables more accurate predictions and proactive decision-making, improving the system's overall efficiency and effectiveness. The system and method may provide that trust scores are computed for each provider and group of providers, enabling the system to evaluate or classify their performance and reliability based on objective data. This arrangement improves transparency, accountability, and fairness in the authorization process while reducing potential errors and inconsistencies.

BRIEF DESCRIPTION OF THE DRAWINGS

FIG. 5 is a block diagram showing an illustration of an electronic format of an authorization form, according to an exemplary embodiment.

FIGS. 6A, 6B, and 6C, respectively, show block diagrams that illustrate a splitting mechanism of an authorization request into multiple service requests, according to an exemplary embodiment.

FIG. 7A is a block diagram illustrating a table including CPT® codes, according to an exemplary embodiment.

FIG. 8A is a block diagram showing an illustration of a table of sample ICD codes, according to an exemplary embodiment.

FIGS. 13A and 13B are illustrations showing the implementation of the machine learning model by the IAS for authorizing requests, according to an exemplary embodiment.

FIG. 19 is a block diagram showing an illustration of a dashboard, including a detailed view of authorization requests, according to an exemplary embodiment.

DETAILED DESCRIPTION

Figure 1:
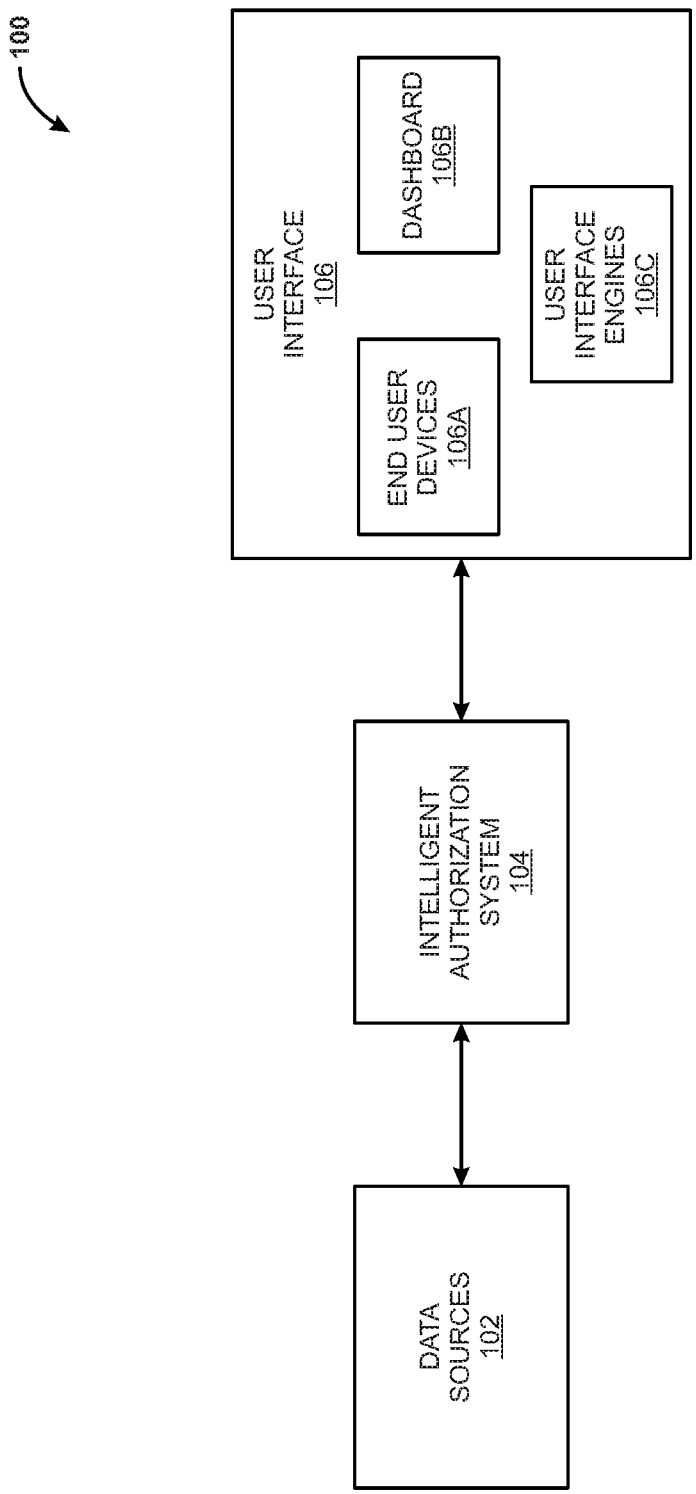
FIG. 1 is a block diagram showing an environment that includes an intelligent authorization system, according to an exemplary embodiment.

The following description provides numerous specific details to provide a thorough understanding of the present disclosure. However, one skilled in the art will realize that the present disclosure may be practiced without these specific details. In other instances, systems, apparatuses, and methods are shown in block diagram form only to avoid obscuring the present disclosure.

In this specification, reference to "one embodiment," "an embodiment," or "example embodiment" means that a particular feature, structure, or characteristic described in connection with the embodiment is included in at least one embodiment of the present disclosure. The appearance of the phrase "in one embodiment" in various places in the specification does not necessarily all refer to the same embodiment, nor are separate or alternative embodiments mutually exclusive of other embodiments. Further, the terms "a" and "an" do not denote a limitation of quantity but denote at least one of the referenced items. Moreover, various features are described, which may be exhibited by some embodiments and not by others. Similarly, various requirements are described, which may be requirements for some embodiments but not for other embodiments.

The terms "comprise," "comprising," "includes," or any other variations thereof are intended to cover a non-exclusive inclusion, such that a setup, device, or method that comprises a list of components or steps does not include only those components or steps but may include other components or steps not expressly listed or inherent to such setup or device or method. In other words, one or more elements in a system or apparatus proceeded by "comprises . . . a" does not, without more constraints, preclude the existence of other elements or additional elements in the system or method.

The terms machine learning model or machine learning engine may refer to a computational, statistical, or mathematical model or engine that is trained on machine learning modeling techniques. The machine learning model or the machine learning engine may be trained over a set of data using techniques or mechanisms that are used to learn or model based on the information in the dataset.

An artificial intelligence model may refer to a model built using simple or complex Neural Networks, deep learning techniques, and computer vision techniques or mechanisms. The artificial intelligence model learns from the data and applies that learning to achieve specific pre-defined objectives.

An artificial intelligence (AI) based intelligence authorization system (IAS) is described herein. In an embodiment, the IAS may also be referred to as a system, an integrated system, etc., when embodied with one or more hardware processing elements. The IAS may further include a communicatively coupled integrated framework of multiple machine learning engines and machine learning models that may execute operations independently or in cooperation to perform certain operations or functions. The AI-based IAS may also be interchangeably referred to as IAS or an integrated system and may include an independent or collaborative execution of operations by multiple engines, models, circuitries executing logic, code, etc. An authorization request or a request for authorization may correspond to a request for authorizing one or more medical services or procedures or one or more medical claims, either prior to a procedure or after the procedure has been performed. The claims process after the procedure may be associated with medical claims bill settlements. An engine may correspond to a special purpose program or an executable code that enables the execution of core and/or supplementary functions or operations. The IAS may implement the execution of multiple engines that may be configured to train multiple machine learning models and may execute specific operations or tasks either independently or in cooperation. In an embodiment, the training and retraining steps may include adjusting the weights of nodes in the machine learning models. A model or a means or a mechanism of modeling may include creating or improvising a functional or operational aspect of a system or features of the system by referencing an existing or known knowledge base. The outcome of the modeling process is to learn or train continually from the data, modify the data, and optimize or improve the functional or operational aspects or features of the system.

In an embodiment, the IAS may execute operations that may include, for example, identification, determination, processing or analysis, computations, evaluation, quantification, and visualization. Modeling may be automated through a continual process of training the machine learning model with data from multiple sources. The engines, the models, the circuitries executing logic, the code, etc., may implement an execution of the functions or operations based on configured rules and/or a sequence of steps to produce specific outcomes. In an embodiment, the IAS may adapt to execute operations based on the data, modifications, or changes in the data. For example, metrics may be computed using the input data, modifications to the data, one or more rules, one or more policies, one or more techniques or mechanisms, one or more outputs of the machine learning engines, one or more outputs of the machine learning models, etc. In an embodiment, the term automatic in the subject specification may correspond to the adaptation that may be in response to the execution of operations by the engines, circuits, models, systems, etc., without any human intervention. The term real-time may correspond to a system response that is immediately based on received data or modifications in the received data.

The following terms may be used in the subject specification that are described as follows. An authorization request, also interchangeably referred to as medical authorization requests, medical claims request, claims request, etc., may correspond to a formal request submitted by a healthcare provider (doctor, hospital, etc.) to a patient's health insurance company seeking approval for a specific medical service, procedure, or medication before it is provided. In an embodiment, different types of medical authorization requests may include multiple attributes (e.g., also referred to as first attributes, second attributes, etc.) that may correspond to inpatient admissions (e.g., hospital stays) for hospitalizations or stays in skilled nursing facilities; outpatient procedures such as surgeries, certain diagnostic tests, or specialist consultations; medications, especially for expensive, brand-name, or specialty drugs; durable medical equipment (DME) such as wheelchairs, oxygen tanks, etc.

In an embodiment, attributes or parameters (e.g., also referred to as first attributes, second attributes, etc.) associated with the authorization requests may include Patient Information, such as Name, Date of Birth, Insurance ID number, and Contact Information, Provider Information, such as Name of the physician or facility, National Provider Identifier (NPI), Tax ID Number, and Contact information (address, phone, fax); Service/Procedure Details such as Specific code for the procedure or service (e.g., CPT codes, ICD-10 codes), Description of the service, Date of service (proposed or actual), Place of service (hospital, clinic, etc.), Diagnosis codes (ICD-10). In an embodiment, one or more identifiers may be associated with one or more services provided by the hospitals.

In an embodiment, some common medical codes used in healthcare may include Current Procedural Terminology (CPT) Codes. The purpose of CPT codes is to describe specific medical procedures and services performed by healthcare providers. CPT codes are used by doctors, hospitals, and other healthcare providers for billing purposes. Typically, CPT codes are primarily numeric codes (5 digits) with some letters used as modifiers. For example, 99213-Office visit for an established patient; 36558-Insertion of a central venous catheter. In an embodiment, the medical codes may include ICD (International Classification of Diseases) Codes. The purpose of ICD codes is to classify diagnoses and medical conditions. This creates a standardized language for reporting diseases, injuries, and causes of death. The ICD codes are typically used by healthcare providers, researchers, and public health organizations. Typically, ICD codes are alphanumeric, and typically in use is ICD-10-CM (Clinical Modification). For example, ICD codes may include E11.9-Type 2 diabetes without complications; S82.101A-Unspecified fracture of the right tibia, initial encounter for closed fracture.

FIG. 1 is a block diagram showing an environment 100 that includes an intelligent authorization system, according to an exemplary embodiment. FIG. 1 is an illustration showing an environment 100 that includes a communicatively coupled arrangement of data sources 102, an intelligent authorization system (IAS) 104, and a user interface 106. In an embodiment, the data sources 102 may include information or data from multiple sources. For example, the data sources 102 may include internal data repositories and external data repositories. In an embodiment, the external data repositories may include external data from outside the healthcare entities, such as healthcare data, World Health Organization, national health services, center for disease control, and including data such as healthcare data, world health organization, national health services, Center for Disease Control, etc. The internal data repositories may include internal data from inside of the healthcare entities and including data such as clinical data, electronic medical record (EMR), administrative data, claims data, patients, care coordinators, medical licensed providers, pharmacies, and other providers, medical claims data, data associated with authorization requests, such as historical authorization requests (e.g., historically approved authorization requests, historically rejected or denied authorization requests, historical authorization requests flagged for reviews, redirecting the authorization requests to Medicaid or Medicare for further scrutiny, etc.), and the like. The data in the internal repositories and external repositories may be stored in multiple formats that may be normalized and processed by the machine learning engines and/or machine learning models (not shown) in the IAS 104. In an embodiment, the data in the external repositories may additionally store or include measures or metrics that may be used for benchmarking. For example, key performance indicators (KPIs) that measure the quality of tasks related to healthcare provisioning, a measure of information or data associated with the treatment of prevalent diseases, such as cancer, a measure of cost associated with healthcare provisioning for diagnosis and/or treatment of the prevalent diseases, etc. The metrics may also correspond to the quality of tasks related to healthcare provisioning, which may be defined and managed by national healthcare regulators, such as the Healthcare Effectiveness Data and Information Set (HEDIS).

In an embodiment, the internal data repositories may be private or restricted to a specific healthcare entity or a hospital that may be provisioning healthcare services in specific geographical areas. Such internal data repositories may include information or data related to services offered and associated costs, demographic coverage-related information, patient population information, risk factors associated with the patients that are based on the patient's health conditions, lifestyle habits, socioeconomic factors, etc. Further, information or data may include the influence of demographic factors such as Medicaid and disability status, gender, age, and whether a beneficiary or a patient is living in a community or an institution. For example, the patient or beneficiary may live in a skilled nursing facility.

Further, the information may include data corresponding to assessed risk, healthcare common procedure coding system (HCPCS), data associated with care coordinators, licensed providers, healthcare services, etc. Further internal data repositories may also include information associated with budget data, current and planned expenditures, expected income, budget targets, etc. The data stored in the external data repositories and the internal data repositories may store data that may be interchangeably referred to as the first dataset, the second dataset, the third dataset, etc. The multiple engines and/or the models of the system may execute operations on the data (e.g., the first dataset, the second dataset, the modified dataset, etc.) to perform processing or analysis, and the results of the processing or analysis may provide insights into one or more tasks that may be used to make further decisions.

In an embodiment, the IAS 104 may include an integration of multiple machine learning engines and machine learning models (not shown). The IAS 104 may implement the execution of multiple machine learning engines, machine learning models, circuitries, code executed by the circuitries, etc., to execute specific operations or functions. The machine learning engines may execute operations by augmenting or accessing data related to historical data, real-time data, data from internal data repositories (e.g., independent hospitals, hospital networks, etc.), external data repositories, etc.

In an embodiment, the IAS 104 may implement the execution of multiple operations on the data that is stored in the external repositories and the external repositories. The results or outcomes of the execution of the operations may include organizing or grouping the authorization requests into cohorts based on one or more criteria, splitting the authorization requests based on one or more criteria into one or more services, encoding the authorization requests or service requests using fixed-length encoding, automatically approving the authorization requests, automatically denying the authorization requests, and providing recommended actions/decisions that may aid in the authorization of requests (e.g., for rejected or denied authorization requests, for authorization requests that may be flagged for review or redirecting the authorization requests to Medicaid or Medicare for further scrutiny, etc.) received in real-time. Further, each recommended action may be supported by the previously harvested or historical authorization requests. For example, previously harvested authorization requests may correspond to the authorization requests that may have been scrutinized and audited with clear explanations for supporting decisions and recommendations. Such previously harvested authorization requests may also be referred to as historical authorization requests. The historical authorization requests could be supplemented with additional information by the human operators/reviewers. The IAS 104 may use such supplemental information and execute operations to recalibrate or make decisions for either approving, denying, or flagging the authorization of requests for review or redirecting the authorization requests to Medicaid or Medicare for further scrutiny that may be received in real-time.

In an embodiment, in response to the recommended actions and decisions, stakeholders or end users consuming the outcome or results of the IAS 104 may be able to identify or determine the basis (or context) of the recommended actions and decisions. By being able to relate the recommended actions and decisions for the authorization request in terms of the decisions (or recommendations) of a similar historical authorization request, the end users may have a natural and intuitive way of either rejecting the recommended action in whole or in part. The end users may provide feedback to the IAS 104, thereby reinforcing the decision-making mechanism. In an embodiment, by being able to relate the recommended actions and decisions in terms of their previous actions (e.g., historically approved requests, historically rejected requests, historically recommended actions, etc.), the end users may have a natural and intuitive way of either rejecting the recommended action in whole or in part and providing granular feedback to IAS 104 on what part of the explanation process went wrong.

In an embodiment, by being able to aggregate the metrics or statistics of the components of the correct or erroneous actions and recommendations, the IAS 104 may be able to provide granular feedback in terms of their strengths or limitations as well as any specific, explicit corrective action. For instance, consider a scenario in which the IAS 104 executed operations, the recommended action explanation was correct, and the authorization request was approved. However, a similar or identical historic authorization request may have the recommended action that needed to be corrected, and the authorization request was denied. In such a scenario, the IAS 104 may execute operations to learn the granular details of the authorization request that was approved and the historical authorization request that was denied or rejected and make suitable recommendations for actions in the future. In an embodiment, since the strengths and limitations of the IAS 104 may be naturally captured during routine operation, the metrics or the basis on which the authorization requests are either approved or denied may constitute a basis for credibility. The historically credible decisions of the IAS 104 may further constitute the basis of trust for the stakeholders or decision-makers. The overall statistics, for example, of errors or correct decisions, may collectively form a basis for the feedback to the regulator authorities in terms of revising the rule content, format, presentation, or training the machine learning engines in the IAS 104.

In an embodiment, the user interface (UI) 106 system may include end user devices 106A, dashboards 106B, and user interface engines 106C. The UI 106 system may be configured to create or generate dashboards and UIs to display the visualizations created or generated in response to the execution of the operations by the IAS 104. The dashboards and UIs created or generated may be configured to receive inputs, and based on the received inputs, the IAS 104 may execute further operations for authorization of requests.

Figure 2:
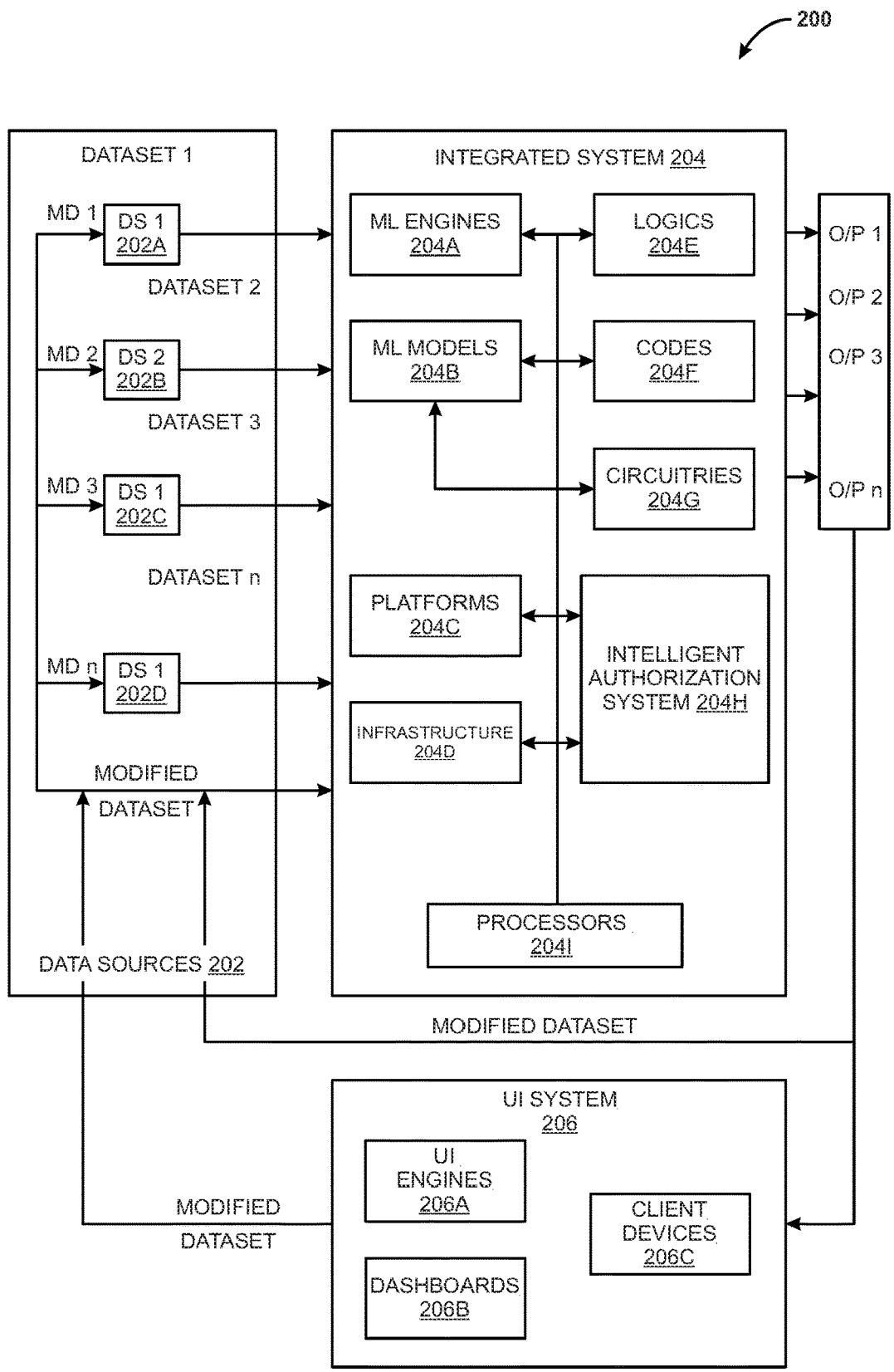
FIG. 2 is a block diagram showing an environment that includes the deployment of an integrated system, according to an exemplary embodiment.

FIG. 2 is a block diagram showing an environment 200 that includes a deployment of an integrated system, according to an exemplary embodiment. FIG. 2 is described in conjunction with FIG. 1. FIG. 2 shows an illustration of an environment 200 that includes a communicatively coupled arrangement of data sources 202, an integrated system 204, and a UI system 206. As described with reference to FIG. 1, the data sources (e.g., 102 and 202) may include multiple data repositories (e.g., DS1 202A, DS2 202B, DS3 202C, . . . DSn 202D) respectively storing multiple datasets (e.g., DATASET 1, DATASET 2, DATASET 3, . . . . DATASET n). In an embodiment, the data sources 202 may source data or information from multiple data sources (e.g., 202A, 202B, 202C, and 202D). For example, such data sources (e.g., 202A, 202B, 202C, and 202D may include internal data repositories and external data repositories, as described with reference to FIG. 1.

The internal data repositories and the internal data repositories may store the data in multiple formats that may be pre-processed and normalized by the machine learning engines (e.g., 204A), machine learning models 204B, platforms 204C, infrastructure 204D, intelligent authorization system 204H, etc. In an embodiment, the data sources 202 may include modified data (e.g., MD1, MD2, MD3, . . . . MDn) that may be generated in response to the execution of operations by the integrated system 204. Further, the modified dataset may be generated or produced when external users provide inputs via the UI system 206. In an embodiment, the modified dataset may be generated or produced when the machine learning engines 204A execute operations on the data received, and this modified data is stored back into the data sources.

In an embodiment, the integrated system 204 may include multiple machine learning engines 204A, machine learning models 204B, platforms 204C, logic 204E, codes 204F, circuitries 204G, intelligence authorization system 204H, infrastructure 204D, and processors 204I that may be communicatively coupled with each other. For instance, a machine learning engine may correspond to a special purpose program or an executable code that performs or executes one or more core functions or operations. The machine learning models 204B may be trained by the machine learning engines 204A in real-time or based on historical information or training data based on data from multiple data sources. In an embodiment, the training and retraining involve adjusting the weights of nodes in the machine learning models based on patterns detected in the dataset, for example, the first data set, the second dataset, etc. The machine learning engine 204A may execute operations on the data, and the machine learning models 204B may be retrained based on the modified dataset. The weights of the nodes of the machine learning models 204B may be adjusted or modified based on the patterns in the modified dataset. In an embodiment, the dataset may include historically approved authorization requests, historically rejected authorization requests, historical authorization requests flagged for reviews, reviews, and decisions related to previously submitted authorization requests, etc. The machine learning engines 204A and/or machine learning models 204B may be configured to execute operations or functions independently or in conjunction with one or more engines or models. In an embodiment, the training or retraining of the machine learning models 204B may be based on the outputs, including adjusting the weights of the nodes using back-propagation. The above-described arrangement enables the machine learning models 204B to continuously improve its accuracy and adapt to new data or changing circumstances, thereby improving the overall performance of the authorization request processing compared to manual processes.

In an embodiment, the execution of operations by the machine learning engines 204A, the machine learning models 204B, etc., may produce outputs or specific outcomes (e.g., o/p1 1, o/p 22, o/p 3, . . . o/p n). The outputs or specific outcomes (e.g., o/p 1, o/p 2, o/p 3, . . . o/p n) may be received and displayed at the UI system 206. In an embodiment, the outputs or specific outcomes (e.g., o/p 1, o/p 2, o/p 3, . . . o/p n) may represent a modified dataset. Further, the outputs or specific outcomes (e.g., o/p 1, o/p 2, o/p 3, . . . o/p n) may be used by the end-user or be modified through suitable user interfaces (UIs) (e.g., dashboards, screens, etc.) or computing devices (e.g., mobile phones, computers, PDAs, portable electronic equipment, etc.) in the UI system 206. The modified dataset (e.g., MD 1, MD 2, MD 3 . . . . MD n) may be stored back into the multiple data stores (e.g., DS1 202A, DS2 202B . . . DSn 202D). Further, the modified dataset may be used to retrain the machine learning engines 204A or the machine learning models 204B in the integrated system 204.

In an embodiment, the integrated system 204 may execute operations to perform multiple analyses. For instance, such analysis may be performed in multiple dimensions. For example, such analysis may include performing identifications or determinations based on multiple key performance indicators or metrics associated with the authorization requests. Based on the analysis, integrated system 204 may generate or create multiple multidimensional visualizations that may provide insights associated with a measure of key performance indicators (KPIs). For example, the KPIs may be associated with multiple patterns of authorization of requests associated with medical claims. The created or generated visualizations may further provide insights into data patterns associated with the approval of authorization requests, denial or rejection of authorization requests, authorization requests that may be flagged for further review, etc. The integrated system 204 may generate or create recommendations related to improving the chances of approval of the denied or rejected authorization requests or authorization requests that may be flagged for further review or redirecting the authorization requests to Medicaid or Medicare for further scrutiny.

In an embodiment, the integrated system 204 may implement the execution of operations of the machine learning engines 204A, the machine learning models 204B, the platforms 204C, the intelligent authorization system 204H, and the infrastructure 204D via one or more logics (e.g., 204E), one or more circuitries (e.g., 204G), and/or one or more codes (e.g., 204F) that are executable by the processors (e.g., 204I). Such implementation may facilitate the execution of operations by the machine learning engines 204A, the machine learning models 204B, the platforms 204C, the intelligent authorization system 204H, the infrastructure 204D via one or more logics (e.g., 204E), one or more circuitries (e.g., 204G), and/or one or more codes (e.g., 204F) that are executable by the processors (e.g., 204I). In an embodiment, the machine learning engines 204A and the machine learning models 204B may execute operations to augment datasets (e.g., the first datasets, the second datasets, modified datasets, etc.), perform contextual-based analysis and identifications or determinations based on the datasets (e.g., first datasets, second datasets, modified datasets, historical information, or historical datasets, etc.), perform situational based analysis and identifications or identifications or determinations based on the datasets (e.g., first datasets, second datasets, modified datasets, historical information, or historical datasets, etc.), etc.

In an embodiment, the UI system 206 may include UI engines 206A, dashboards 206B, and client devices 206C that may display the integrated system's 204 results or outcome of the execution of the operations. The UI engines 206A may be configured to create or generate UIs that may provide an interface to interact with the end users. For example, the UIs created or generated by the UI engines may be configured to receive inputs from end users, and based on these inputs (e.g., represented by modified datasets), the machine learning engines 204A and the machine learning models 204B may be trained or retrained. The mechanism of training or retraining the machine learning engines 204A or the machine learning models 204B may further enable improvising or refining the specific outcomes or specific results. In an embodiment, refining or improvising may correspond to improving technical outcomes or technical metrics, such as key performance indicators or key performance values, thereby leading to improved outcomes associated with the approvals or denials or flagging for the review of authorization requests or redirecting the authorization requests to Medicaid or Medicare for further scrutiny. The operations or functions may be maximized by implementing automatic approval and/or denial mechanisms that may optimize the operations, tasks, etc., executed at the hospital. The machine learning engines 204A, the machine learning models 204B, etc., may execute operations to perform computations or re-computations based on specific modifications of the dataset (e.g., the first dataset, the second dataset, etc., represented by the modified dataset) and may retrain the machine learning engines 204A and the machine learning models 204B thereby providing improvisation of the services, tasks, processes, operational parameters associated with hospital ecosystem. In an embodiment, the mechanism or training or retraining of the machine learning models 204B using the machine learning engines 204A may adjust or modify the weights of the nodes in the machine learning models 204B.

For example, let us consider an example of how the weights of nodes in a neural network-based machine learning model may be adjusted during training in the context of medical claims authorization. Suppose we have the machine learning model 204B that takes various attributes of a medical claim as input (e.g., patient age, diagnosis codes, procedure codes, medication codes) and predicts whether the claim should be authorized or not. Initially, the weights of the nodes in the machine learning models 204B are randomly initialized. During training, the model is presented with a batch of training examples, each consisting of input attributes and the corresponding authorized/not authorized label.

Let us consider the following Input attributes: [age: 45, diagnosis_code: D123, procedure_code: P456, medication_code: M789]; Actual label: Authorized.

The machine learning models 204B processes this input through its layers, applying the current weights to compute the activations of the nodes in each layer. At the output layer, the machine learning models 204B may generate a probability score indicating the likelihood of the claim being authorized.

Suppose the machine learning models 204B predicts a probability of 0.3 for the "Authorized" class, while the actual label is "Authorized" (which may be represented as a probability of 1.0). In an embodiment, the training or retraining process then computes the prediction error, which is the difference between the predicted probability and the actual label. In this case, the error is 1.0-0.3=0.7. The objective of training or retraining is to minimize this prediction error. To achieve this, the machine learning model 204B uses an optimization technique, such as gradient descent, to update the weights of the nodes in the network.

In an embodiment, the optimization mechanism or technique may compute the error gradients with respect to each weight in the network using backpropagation. The gradients indicate how much each weight contributes to the prediction error. Based on the computed gradients, the optimization algorithm adjusts the weights in the direction that reduces the error. A learning rate hyperparameter controls the magnitude of the weight update. For example, if the gradient of the error with respect to a particular weight is positive, it means increasing that weight will reduce the error. The optimization algorithm will update the weight by subtracting a small value (learning rate*gradient) from its current value. Conversely, if the gradient is negative, the weight will be updated by adding a small value to its current value.

This process is repeated for all the weights in the network, gradually adjusting them to minimize the prediction error. The training or retraining process iterates over multiple batches of training examples, updating the weights each time until a satisfactory level of performance is achieved, or a predefined number of iterations (epochs) is completed. As the weights are updated based on the training data, the model learns to make more accurate predictions about medical claims authorization. The adjusted weights capture the patterns and relationships in the data that are relevant to authorization decisions. In an embodiment, when the machine learning models 204B encounters new, data or new authorization requests that are unfamiliar, it uses the learned weights to process the input attributes and predict the likelihood of authorization based on the patterns it has learned during training.

In an embodiment, the machine learning models 204B may include neural networks that may be trained by the machine learning engines 204A using backpropagation and gradient descent algorithms. The training process may include hyperparameter tuning to optimize the accuracy and efficiency of the machine learning models 204B.

Figure 3:
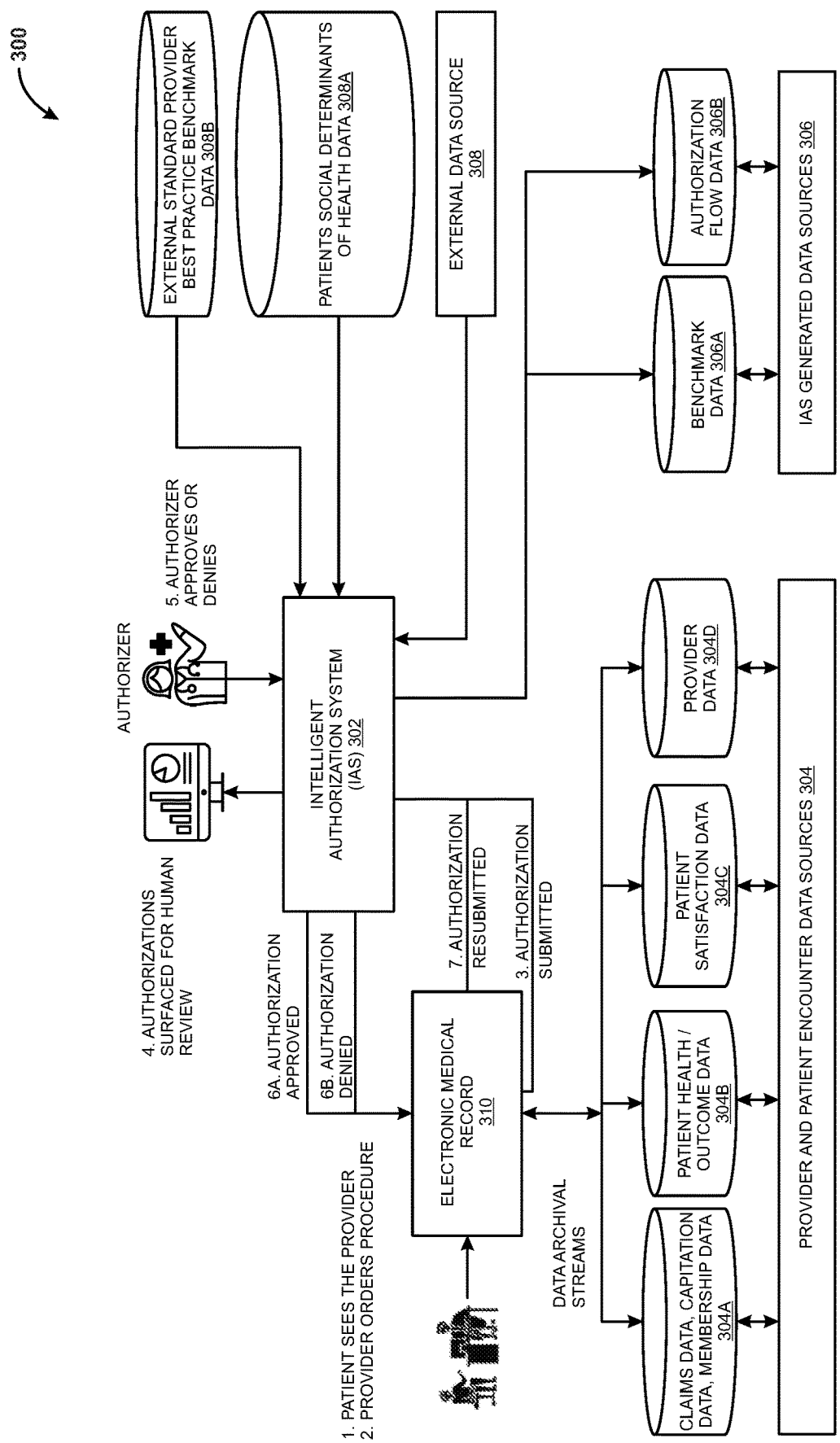
FIG. 3 is a block diagram illustrating the deployment of the IAS in a hospital ecosystem, according to an exemplary embodiment.

FIG. 3 is a block diagram 300 illustrating the deployment of the IAS in a hospital ecosystem, according to an exemplary embodiment. FIG. 3 is described in conjunction with FIGS. 1 and 2. FIG. 3 is a block diagram 300 showing an illustration of the deployment 300 of the IAS 104 and 302 in a hospital ecosystem. In an embodiment, the IAS 104 and 302 may implement the execution of multiple circuitries, engines, models, etc., to execute specific operations, as described in FIG. 1 and FIG. 2. IAS 104 and 302 may execute the above-described operations on the information, including data assimilated from multiple data sources 102. The data sources 102 may include internal data repositories or external data repositories (e.g., 308), including data identifiers and information related to operations, processes, actions, patient information, authorization requests, etc., associated with a hospital. The external data repositories may include data or information corresponding to patients' social health determinants of health data 308A and external standard provider best practice benchmark data (e.g., 308B).

In an embodiment, the data sources 102 may include data or information related to one or more service providers (also referred to as providers), patients, patient encounter data (e.g., 304), and the IAS generated data 306. Further, the data may include health insurance data, also referred to as claims data, capitation data, membership data (e.g., 304A), patient health and/or outcome data (e.g., 304B), patient satisfaction data (e.g., 304C), provider data (e.g., 304D), etc. The patient health and/or outcome data 304B may include an electronic medical record (EMR) 310, patient satisfaction data 304C, and provider data 304D. In an embodiment, the provider data 304D may correspond to individual provider data or a group of providers. The IAS generated data 306 may include benchmark data 306A and authorization flow data 306B.

In an embodiment, the IAS 104 and 302 may implement execution of multiple circuitries, decision logic, engines, etc. (not shown) that may work independently or in cooperation to execute operations. For example, the machine learning engines in the IAS 104 and 302 may execute operations to authorize requests automatically based on multiple evaluations and processing or analysis mechanisms. Such mechanisms may be implemented on the basis of the computation of a trust score, identifying or determining similarities between authorization requests, computing distances between the authorization requests, etc. In an embodiment, the machine learning engines in the IAS 104 and 302 may be configured to execute operations to perform computations based on various attributes or parameters. For example, such attributes or parameters may include identifying or determining the trustworthiness of individuals (e.g., licensed professionals, doctors, nurses, support staff, etc.), the trustworthiness of individual service providers, the trustworthiness of groups of service providers, the trustworthiness of serving entities, and the trustworthiness of managing entities. The identification or determination of trustworthiness may be computed with respect to time and may be based on parameters such as previous outcomes, competence, credibility, integrity, patient satisfaction data, etc.

Referring to FIG. 3, there is shown that a patient may visit the hospital or healthcare facility, for example, the healthcare facility provider (e.g., shown as Step 1: patient sees the provider). Upon visiting the healthcare facility, the doctor attending to the patient may order or submit a request to perform a medical diagnosis and/or a surgical procedure (e.g., shown as Step 2: provider orders procedure). The requested medical diagnosis and/or the surgical procedure may need authorization for Its execution, which may be received by the IAS 104 and 302 (e.g., shown as Step 3. Authorization submitted). The IAS 104 and 302 may execute operations to perform operations, such as processing or analysis, computations, identifications, determinations, evaluations, verifications, etc., and provide recommendations and actions based on the submitted medical diagnosis and/or surgical procedures. The recommendations and actions may be displayed on a dashboard or UI for review.

In an embodiment, the IAS 104 and 302 may execute operations that may include identifying or determining the similarity metrics of the authorization requests with reference to the historical authorization requests. For example, suppose the authorization requests received in real-time have metrics that are similar to the historically approved authorization requests or historically denied or rejected authorization requests. In such a scenario, the similarity metric may be attributed as a basis for an automatic measure of confidence with reference to decision-making by IAS 104 and 302. In an embodiment, the automatic measure of confidence may also correspond to a recommended action that IAS 104 and 302 may execute and provide as a response to the execution. Such measure of confidence may further be leveraged to prioritize the attention of the authorizer, for example, sponsor agents toward the efforts that are most productive in their productivity measures. The sponsor agents may also have the flexibility to incorporate their productive measures to customize their most high-priority work.

For instance, when all the authorization requests received in real-time are the closest historical authorization requests were credible, and they all recommended approval for the closest historical authorizations, the IAS 104 and 302 confidences in the recommended action (e.g., approval) may be high. For example, the distance of the presented authorization request to their corresponding nearest neighbors may be identified or determined by their respective similarity metrics. Other visual attributes of their presentation may further modulate aspects of their similarity (or differences). For example, the age groups of the patients associated with the requests may be indicated using the colors of their respective presentations.

In an embodiment, one effective approach to handling authorization requests involves comparing them using a similarity metric. This metric may be used to evaluate the requests as a whole or to break them down into individual components, which may then be compared. The metric may be designed manually, learned, or a combination of both. Using the similarity metric, a new authorization request may be compared with historical authorization requests to identify any similarities. By processing or analyzing the historical decisions made for similar requests, the IAS 104 and 302 may either automatically approve, deny, or reject the authorization request or suggest appropriate action for the authorization requests received in real-time. The execution of operations by IAS 104 and 302 may generate or create results that lead to confidence in the recommended action based on the credibility of the agents involved in the historical decisions. Furthermore, the similarity metric may consider distinct factors, such as the time of day, the department or team involved, and the specific assets or resources requested. This mechanism may lead to more accurate and consistent decision-making, as it considers a wide range of variables that may influence authorization decisions. Overall, the use of a similarity metric to compare the authorization requests may improve the efficiency and accuracy of the authorization process while also ensuring that the system makes fair and consistent decisions.

Referring to FIG. 3, an authorized or qualified end user may review the submitted request for the medical diagnosis and/or the surgical procedure. (e.g., shown as Step 4. Authorizations surfaced for human review). In an embodiment, the authorized or qualified end user may either approve or deny the execution of services in the authorization request that is submitted (e.g., shown as Step 5. Authorizer approves or denies). When the authorization request is denied or rejected, the request may be resubmitted to the IAS 104 and 302 (e.g., shown as Step 14. Authorization resubmitted.) Upon receiving the resubmitted request, the IAS 104 and 302 may execute operations and based on the trust score, may automatically approve the authorization request (e.g., shown as Step 6A. Authorization approved) or automatically deny the authorization request (e.g., shown as Step 6B. Authorization denied) to execute the requested medical diagnosis and/or surgical procedure.

In an embodiment, the IAS 104 and 302 may enable or implement a mechanism for authorizing requests for the execution of services. For example, such services may be associated with insurance procedures, medical treatment, or diagnostic procedures. The IAS 104 and 302 may cooperatively work or execute operations with the UI engine 106C and may execute operations to generate or create user interfaces (UIs) or dashboards. The UIs may provide or facilitate displaying information or data in response to the execution of operations by the engines, models, circuits, framework, etc., of the IAS 104 and 302. In an embodiment, the IAS 104 and 302 may execute operations to provide means for organizing information or data based on an execution of operations or functions.

In an embodiment, the end user may be able to provide inputs via user interfaces or dashboards. Based on the user inputs, the machine learning engines in the IAS 104 and 302 may execute operations and provide recommendations. For example, recommendation engine in the IAS 104 and 302 may provide recommendations that may be based on historical data or information related to patient healthcare records, patient demographic information, socio-economic factors, etc. In an embodiment, the machine learning engines may execute operations for receiving and processing or analyzing user inputs and processing and analyzing the input in a recommended decision or a recommended outcome.

In an embodiment, the machine learning engines in the IAS 104 and 302 may cooperatively work with the UI engine 106C to render the recommended decision to the end user. The rendered recommended decision may provide additional input or information that may aid the end user in deciding the final disposition of the authorization request. In an embodiment, the basis of the recommended decision for the input decision is explained in terms of attributes of prior (historical) authorization requests. In an embodiment, UI or dashboards may enable end users to modify the disposition of the authorization requests or modify at least one attribute of the prior request.

In an embodiment, the IAS 104 and 302 may enable comparing historical authorization requests with the new authorization requests or authorization requests received in real-time that may be organized as cohorts of input service requests based on the similarity of the attributes of the authorization requests with the historical authorization requests. For example, the historical authorizations requesting identical service requests may be grouped into cohorts. More specifically, if authorization requests A1, A2, and A3 . . . all are requesting the same CPT code 97161 (initial evaluation) service request, they will constitute 97161 cohorts. Further, IAS 104 and 302 may enable the execution of operations that may include the recommended decision for the request being identified or determined by at least the historical disposition of one of the prior cohort requests associated with the request. In an embodiment, the recommended decisions for the request may be categorized into "approved" and "review." The approved authorization requests may not necessitate or require further human inspection.

In an embodiment, a human supervisor may further review the authorization requests recommended for review to determine the final disposition of the authorization request. The authorization of requests and the cohorts are organized to reflect the relationship with respect to historical authorization requests. In an embodiment, at least one attribute of the prior or historical authorization request may be associated with attributes of the identification process of the historical authorization request.

In an embodiment, attributes or parameters that may be used for the identification process may include at least one attribute that may uniquely determine the identity of the operator, determining the final disposition of the historical authorization request associated with the cohort. The final disposition of the authorization request may include determining at least one aspect of the operator determining the final disposition of the associated prior request. When there is a human override of IAS 104 and 302's recommended decision of the authorization request, the trust associated with at least one agency associated with the final disposition of the historical authorization request may be weakened. In an embodiment, when there is a concurrence on the final disposition with the IAS 104, and 302 recommended decisions of the authorization request, the trust associated with at least one agency associated with the final disposition of the historical authorization request may be strengthened.

In an embodiment, a prioritization aspect of the organized authorization request may be represented by a visualization on the user interface. The visualization may be determined by, for example, the size, shape, and texture of the attribute associated with the authorization request. The visualization may include visually highlighting the attributes of the cohort requests associated with the authorization request. In an embodiment, there may be a visual distance associated with the cohort quantifying the similarity of the authorization request with the cohorts of the authorization requests.

Figure 4:
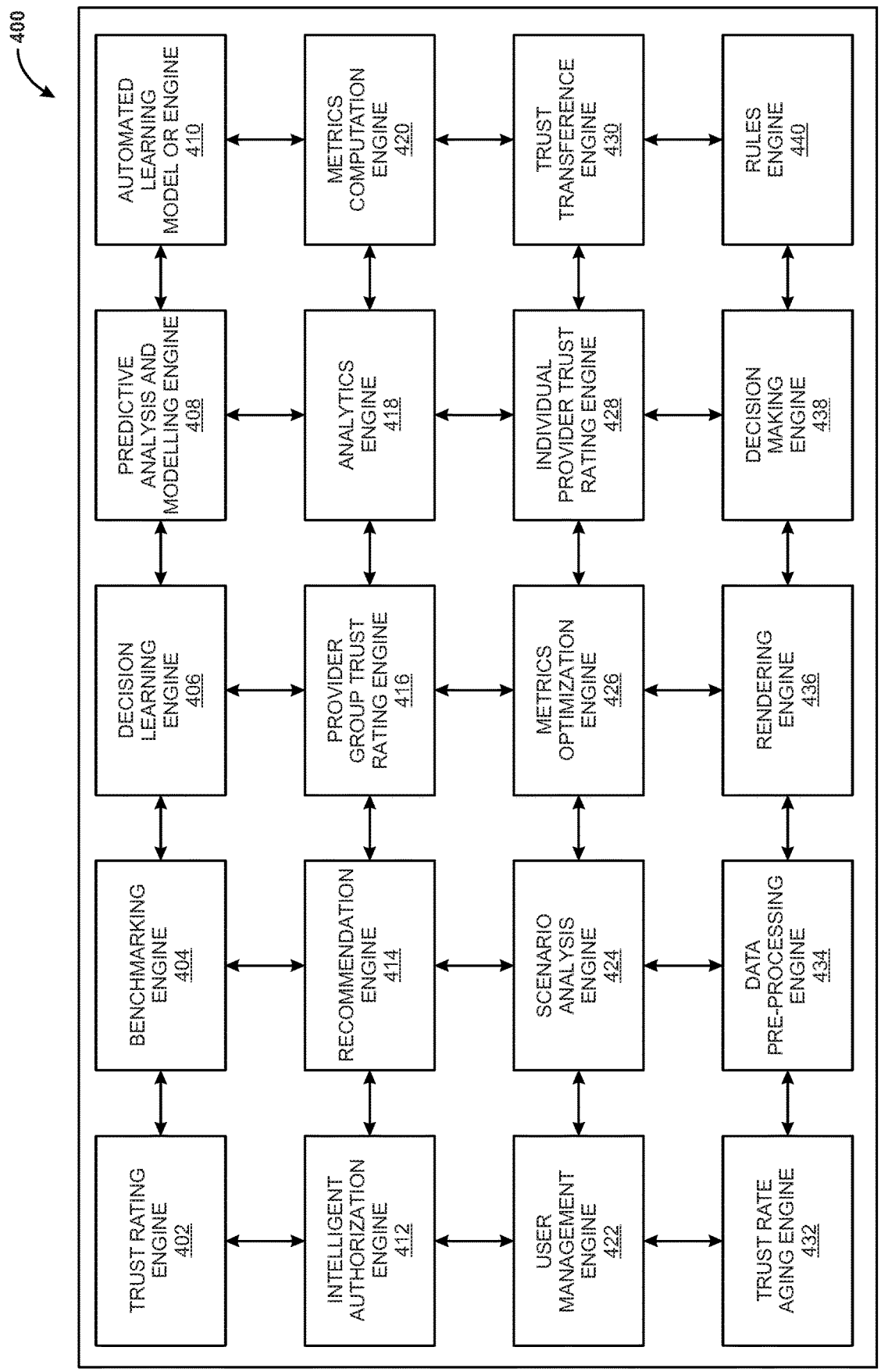
FIG. 4 is a block diagram showing integrated machine learning engines of the IAS, according to an exemplary embodiment.

FIG. 4 is a block diagram 400 showing an integration of machine learning engines of the IAS, according to an exemplary embodiment. FIG. 4 is described in conjunction with FIGS. 1-3. FIG. 4 is a block diagram 400 showing an illustration of the IAS 104 and 302 system. In an embodiment, the IAS 104 and 302 include multiple machine learning engines and machine learning models that are trained by the machine learning engines. The IAS 104 and 302 may include an integration of a trust rating engine 402, a benchmarking engine 404, a decision learning engine 406, a predictive analysis and modeling engine 408, an automated learning model 410, an intelligent authorization engine 412, a recommendation engine 414, a provider group trust rating engine 416, an analytics engine 418, a metrics computation engine 420, a user management engine 422, a scenario analysis engine 424, a metrics optimization engine 426, an individual provider trust rating engine 428, a trust transference engine 430, a trust rate aging engines 432, a data pre-processing engine 434, a rendering engine 436, a decision-making engine 438 and a rules engine 440.

In an embodiment, the trust rating engine 402 may execute operations for computing and assigning trust scores based on historical behavior, and real-time data are used to classify or evaluate the credibility of the providers. The trust rating engine 402 may execute operations to implement a reputation-scoring mechanism that may incorporate factors like past performance, user feedback, and compliance records. The trust rating engine 402 may implement risk assessment technique or mechanisms that process or analyze data patterns to identify potential risks or anomalies with providers. The trust rating engine 402 may be configured to receive feedback from the end users. For example, a feedback loop mechanism may continuously update trust scores based on current information or new data that may be received in real-time. The trust rating engine 402 may further execute operations to identify or determine risk profiles based on score computations. For example, the risk profiles may be identified by performing computations and assigning scores indicating the likelihood of a provider being unable to provide the desired services. The trust rating engine 402 may further execute operations for real-time monitoring of the users and the provider's activities for any changes in trustworthiness. Further, the trust rating engine 402 may execute operations to make dynamic adjustments, such as updating trust ratings in response to new data or events. The technical advantage of the trust rating engine 402 is that it provides accurate trust ratings that enable more informed decisions related to authorization requests.

In an embodiment, the benchmarking engine 404 may execute operations to compare the performance of the providers. For example, the providers may be identified based on the best fit for specific operations. The benchmarking engine 404 may implement the execution of machine learning techniques or mechanisms for comparing the providers. For example, parameters such as accuracy, efficiency, and other relevant parameters may be used to determine the providers' performance metrics. The benchmarking engine 404 may also rely on historical information or data that may be stored as a reference (e.g., past benchmarking data) for future operations or authorization requests. The machine learning models may be updated with new benchmarks or model rankings based on new data or information.

In an embodiment, the decision learning engine 406 may execute operations to learn from the decisions continually. For example, the decision learning engine 406 may implement the execution of techniques or mechanisms to make decisions regarding authorization requests in real-time. The decisions may be based on historical or previous authorization requests and/or other relevant parameters, such as contextual information associated with the authorization requests. The decision learning engine 406 may implement rule-based mechanisms for incorporating pre-defined rules for common scenarios. The decision learning engine 406 may work in cooperation with other machine learning engines and machine learning models in the IAS 104 and 302 and combine multiple machine learning models and machine learning engines' outcomes for more robust decision-making. The decision learning engine 406 may execute operations to process or analyze the authorization requests in real-time. Based on the processing or analysis, the authorization requests may be processed (e.g., outputs may be generated for each service request and rendered or displayed on UIs), and relevant data may be sourced or retrieved. The decision learning engine 406 may execute operations in cooperation with other machine learning engines and machine learning models for predictive modeling. For example, predictive modeling may include evaluating the likelihood of approval or rejection of authorization requests based on historical patterns. The decision learning engine 406 may execute operations with the other machine learning engines and the machine learning models to provide clear, actionable recommendations. The technical advantage of the decision learning engine 406 is that it provides automated decision-making, thereby streamlining the process and reducing human errors.

In an embodiment, a predictive analysis and modeling engine 408 may execute operations by implementing advanced techniques or mechanisms, machine learning techniques, and vast amounts of historical data to streamline and optimize the claims authorization process. The primary objective of the predictive analysis and modeling engine 408 is to accurately process and predict the likelihood of a claim being approved or denied based on several factors and patterns identified in previous claims data. In an embodiment, predictive analysis and modeling engine 408 implement machine learning techniques or mechanisms trained on historical claims data. These models may include decision trees, random forests, support vector machines, or deep-learning neural networks. The choice of technique or mechanism depends on the complexity of the data and the desired level of interpretability. The predictive analysis and modeling engine 408 identifies the most relevant features that contribute to the prediction of claim authorization outcomes. These features may include patient demographics, medical history, procedure codes, provider information, and historical claims patterns. Feature selection techniques help reduce dimensionality and improve model performance. In an embodiment, predictive analysis and modeling engine 408 trains the machine learning models (e.g., 410) using a subset of the historical claims data, typically employing techniques like cross-validation to assess model performance and prevent overfitting. The models (e.g., 410) are fine-tuned based on evaluation metrics such as accuracy, precision, recall, etc., to ensure optimal performance. In an embodiment, predictive analysis and modeling engine 408 may process new authorization requests in real-time. The predictive analysis and modeling engine 408 takes input data related to a specific claim, such as patient information, procedure details, and provider credentials, and applies the trained models using machine learning engines to generate outputs, including predictions of the claim's likelihood of approval or denial.

In an embodiment, the automated learning model 410 may execute operations to cooperatively work with other machine learning engines and machine learning models in the IAS 104 and 302. The automated learning model 410 may learn or train from other machine learning engines using real-time data. The automated learning model 410 may be updated in response to current information without retraining from the beginning. In an embodiment, multiple versions of the automated learning model 410s may be maintained for comparison and rollbacks. The automated learning model 410 may adjust the parameters or attributes based on real-time data. The real-time updates may be propagated to other machine learning engines and machine learning models in the IAS 104 and 302. The automated learning model 410 may enable the new models that are created or generated and recreated or regenerated to remain accurate and relevant. The technical advantage of the automated learning model 410 is that it enables faster adaptations to changing conditions based on real-time data, thereby reducing the need for manual intervention.

In an embodiment, the intelligent authorization engine 412 may execute operations to coordinate, collate, and integrate the outputs of other machine learning engines and machine learning models in the IAS 104 and 302. The intelligent authorization engine 412 may execute operations to coordinate the flow of data, including the authorization requests, and collate and integrate the responses of the machine learning engines in the IAS 104 and 302. The intelligent authorization engine 412 may implement the execution of additional rules and scores for decision logging. For example, the intelligent authorization engine 412 may execute operations to determine the authorization requests that have been flagged for auditing or review or redirect the authorization requests to Medicaid or Medicare for further scrutiny and may send such authorization requests to appropriate machine learning engines for further processing. In an embodiment, the intelligent authorization engine 412 may execute operations to split or partition the authorization requests based on specific criteria. For example, the criteria may be based on codes (e.g., CPT codes, ICD codes, etc.), based on the number of services associated with the authorization requests, etc. The intelligent authorization engine 412 may also execute operations for encoding the service requests or the authorization requests using a fixed-length encoding. For example, the fixed-length encoding may assign a unique numeric identifier based on the presence of a categorical variable.

In an embodiment, when authorization requests are split into multiple service requests, fixed-length encoding may be used to assign a unique numeric identifier to each categorical variable in the service requests. For example, consider the one-hot encoding in the context of fixed-length encoding for authorizing requests in a medical claims processing system.

Suppose that the following categorical variables are related to authorization requests:
  Claim Type: Inpatient; Outpatient; Emergency.
  Procedure Code: 1234; 5678; 9012.
  Diagnosis Code: A123; B456; C789.

In an embodiment, using one-hot encoding, the above-referenced categorical variables may be represented as binary vectors. Each unique category within a variable is assigned a separate binary feature.

The corresponding one-hot encoded representation may include:
  Claim Type: Inpatient: [1, 0, 0]; Outpatient: [0, 1, 0]; Emergency: [0, 0, 1].
  Procedure Code: 1234: [1, 0, 0]; 5678: [0, 1, 0]; 9012: [0, 0, 1].
  Diagnosis Code: A123: [1, 0, 0]; B456: [0, 1, 0]; C789: [0, 0, 1].

Now, let us consider an authorization request for processing a medical claim with the following details:
  Claim Type: Outpatient; Procedure Code: 5678; Diagnosis Code: B456.

Using one-hot encoding, the above authorization request may be represented as follows:
  [0, 1, 0, 0, 1, 0, 0, 1, 0].

In the above-described representation, the first three elements correspond to the Claim Type, the next three elements correspond to the Procedure Code, and the last three elements correspond to the Diagnosis Code. The presence of a 1 indicates the specific category for each variable.

To implement fixed-length encoding, the binary vectors may be padded with zeros when the number of categories varies across different variables. This way, all encoded requests will have the same length, making it easier to process and compare them. In an embodiment, when the IAS 104 and 302 may receive such encoded authorization requests, the IAS 104 and 302 may execute operations to interpret the binary vectors and make authorization decisions based on the specific combination of Claim Type, Procedure Code, and Diagnosis Code.

In an embodiment, fixed-length encoding converts categorical variables into compact numeric representations. This encoding scheme allows for efficient storage, comparison, and processing of the authorization requests or service requests. The fixed-length coding ensures that each encoded value occupies the same number of digits, making it easier to parse and handle the data.

In an embodiment, when the IAS 104 and 302 receive these encoded service requests, they may decode the numeric identifiers back to their original categorical values based on the defined encoding scheme. Fixed-length encoding is particularly useful when dealing with a fixed set of categorical variables and when the number of values for each variable is known in advance. Fixed-length coding provides a compact and efficient way to represent and process categorical data in authorization systems and other applications that involve splitting requests into multiple service requests. In an embodiment, the fixed-length encoding process may reduce the dimensionality of the authorization requests or service requests and improve the efficiency of the authorization request processing by enabling faster comparison and categorization of the requests.

In an embodiment, the intelligent authorization engine 412 may also execute operations to determine contexts, actions, and decisions associated with the authorization requests. For example, the intelligent authorization engine 412 may execute operations in cooperation with the analytics engine 418 to process or analyze the authorization requests received in real-time with the historical authorization requests. The intelligent authorization engine 412 may execute operations to categorize the service requests or authorization requests received in real-time into cohorts. The intelligence authorization engine 412 may execute operations in cooperation with the metrics computation engine 420 to determine similar metrics or similarities between the historical authorization requests and the authorization requests received in real-time. Based on the determination of similarities, the intelligent authorization engine 412 may execute operations to authorize the authorization requests automatically (e.g., approve, reject, flag, audit for review, or redirect the authorization requests to Medicaid or Medicare for further scrutiny, etc.). In an embodiment, the intelligent authorization engine 412 may also execute operations resolving conflicts between two or more authorization requests. For example, authorization requests that may overlap or may have conflicting requests may be flagged for human intervention or redirect the authorization requests to Medicaid or Medicare for further scrutiny. The technical advantage of the intelligent authorization engine 412 is that it provides centralized control and ensures consistency and transparency in the authorization process.

In an embodiment, the recommendation engine 414 may cooperatively work with other machine learning engines and machine learning models in the IAS 104 and 302 to provide personalized recommendations for authorized actions based on user profiles and historical behavior. The recommendation engine 414, in cooperation with the intelligent authorization engine 412, may implement a mechanism for collaborative filtering that may identify similar authorization requests. The technical advantage of the recommendation engine 414 is that it provides personalized recommendations based on multiple attributes and parameters of the data to improve user experience and engagement.

In an embodiment, the provider group trust rating engine 416 may execute operations to evaluate the trustworthiness and classify the provider groups based on their collective performance. The provider group trust rating engine 416 may implement a mechanism for computing group scoring that may compute and assign a group-level score based on individual providers' ratings. The provider group trust rating engine 416 may execute operations to track group-wide metrics like average trust scores and incident rates. Further, the provider group trust rating engine 416 may track collaboration by monitoring interactions between providers within the group. The provider group trust rating engine 416 may combine provider ratings to determine overall trustworthiness and identify or determine areas of improvement. The provider group trust rating engine 416 may generate or create alerts when a meaningful change in the trust of the providers and/or provider groups occurs. The technical advantage of the provider group trust rating engine 416 is that it evaluates and classifies provider groups, helps users make more informed decisions, and manages risk.

In an embodiment, the analytics engine 418 may execute operations to analyze data from multiple data sources and provide insights for decision-making. The analytics engine 418 may execute operations on historical data and real-time data and provide insights that may be used to train the machine learning models using the machine learning engines in the IAS 104 and 302. The analytics engine 418 may generate or create forecasts based on historical patterns in the data (e.g., patterns associated with historical authorization requests), based on the patterns in the data, identify trends and correlations, track performance in real-time, and cooperatively work with UI engines and other machine learning engines to create or generate several types of visualizations based on the processing and analysis.

In an embodiment, the metrics computation engine 420 may execute multiple machine learning techniques to improve decision-making accuracy. The engine may execute operations to determine similarity metrics between historical authorization requests and authorization requests received in real-time. By computing the distance between these similarity metrics, the metrics computation engine 420 may flag authorization requests for auditing for further review or redirect the authorization requests to Medicaid or Medicare for further scrutiny and assist in making decisions related to approval, denial, or rejection.

The metrics computation engine 420 then implemented advanced techniques or mechanisms and machine learning techniques to compute similarity metrics between historical authorization requests and incoming real-time requests. These similarity metrics may be based on several factors, such as patient demographics, medical history, procedure codes, provider information, and historical authorization outcomes. The choice of similarity metrics depends on the specific requirements and characteristics of the healthcare organization and the types of medical claims being processed. For example, distance function mechanisms or techniques, such as distance metric learning, may be implemented or used for computing similarity metrics. The distance metric learning mechanism or technique or mechanism measures the proximity or dissimilarity between two authorization requests in a high-dimensional feature space. By representing each authorization request as a vector of relevant features, the metrics computation engine 420 may calculate the distance between them and determine their similarity.

For example, let us consider a scenario where a patient submits an authorization request for a complex surgical procedure. The metrics computation engine 420 receives this request in real time and begins the similarity analysis process. The metrics computation engine 420 extracts relevant features from the request, such as the patient's age, medical history, procedure codes, and provider information. These features are then compared against a database of historical authorization requests using the chosen distance-based technique or mechanism. The metrics computation engine 420 computes the similarity metrics between the incoming request and the historical requests, considering the extracted features and their respective weights or importance. The metrics computation engine 420 may assign higher weights to critical features, such as the procedure codes or the patient's specific medical conditions, to emphasize their significance in the similarity calculation.

Based on the computed similarity metrics, the metrics computation engine 420 determines the distance between the authorization requests received in real-time and the historical authorization requests. When the distance falls below a predefined threshold, indicating a high degree of similarity, the metrics computation engine 420 may flag the authorization request received in real-time for further review or redirect the authorization requests to Medicaid or Medicare for further scrutiny. This flagging or redirecting mechanism may alert and request for human intervention to examine the request closely and consider additional factors or expert opinions before making a final decision. The similarity metrics and flagged requests or redirected requests are then integrated into the metrics computation engine's overall decision-making process. The metrics computation engine 420 may implement rule-based techniques or mechanisms or machine learning models to process and analyze the similarity metrics alongside other relevant factors, such as clinical guidelines, insurance policies, and historical authorization patterns. The technique mechanisms and models are implemented to determine the appropriate course of action for each authorization request, whether it is approval, denial, or rejection. For instance, if the similarity metrics indicate a high resemblance between the incoming request and historical requests that were historically approved, the metrics computation engine 420, in cooperation with the other machine learning engines (e.g., decision learning engine 406, automated learning model 410, the recommendation engine 414, the intelligent authorization engine 412, and the metrics computation engine 420), may recommend approving the request. Conversely, if the similarity metrics suggest a strong similarity to requests that were denied or rejected in the past, the metrics computation engine 420, in cooperation with the other machine learning engines (e.g., decision learning engine 406, automated learning model 410, the recommendation engine 414, the intelligent authorization engine 412, and the metrics computation engine 420), may recommend denying or rejecting the request, or subject to an audit or further review by the authorization team.

In an embodiment, the metrics computation engine 420 continuously learns and adapts based on the outcomes of the authorization decisions by incorporating feedback loops and real-world results to refine its similarity metrics, technique or mechanisms, and automated learning modes 410 over time. When the volume of data or the number of authorization requests increases, the metrics computation engine 420 may process a larger volume of authorization requests. In an embodiment, the metrics computation engine 420 executes operations for learning distance metrics that automatically generate or create a function to map pairs of authorization requests to a scalar value representing their similarity or dissimilarity. Specifically, the distance metric learning mechanism may be used to implement a representation for authorization requests that better facilitates the discrimination of approved authorizations versus denied authorizations. In an embodiment, the categorization of the authorization requests or the service requests into cohorts using similarity metrics and a distance function may improve the accuracy of the authorization request processing by enabling the machine learning models to identify patterns and similarities among the authorization requests or the service requests.

In an embodiment, a supervised learning mechanism may be implemented to formulate distance metric learning. Distance metric learning may be implemented using various machine learning techniques such as supervised learning, unsupervised learning, or semi-supervised learning. In the supervised learning mechanism, the distance metric is learned by optimizing a loss function that measures the discrepancy between the predicted distances and the true distances between pairs of authorization requests. The learned distance metric may be leveraged by the decision learning engine 406, the automated learning model 410, the decision making engine 438, and the recommendation engine 414 of IAS 104 and 302. By using a distance metric that better reflects the underlying similarity structure of the approved and denied prior authorizations, the IAS 104 and 302 may execute operations to achieve better performance than using a fixed distance metric or a simple distance measure.

In an embodiment, distance metric learning may be used to transform and normalize the feature space by learning a distance metric that considers the underlying similarity structure of the objects (e.g., the authorization requests) in the feature space. This may improve the performance of machine learning techniques or mechanisms that rely on the similarity between objects, such as clustering, classification, and retrieval.

In an embodiment, the distance metric learning for feature space may be executed as a transformation function or mechanism (e.g., also referred to as transformation 2"), and normalization may be described as follows: Consider choosing a suitable distance metric learning technique or mechanism. For example, distance metric learning techniques or mechanisms may include metric learning by similarity propagation, neighborhood components processing and analysis, and a large margin nearest neighbor. The choice of technique or mechanism may depend on the specific outcomes and the characteristics of the authorization requests.

In an embodiment, the distance function, for example, the triplet distance metric learning formulation, may be implemented as described below. The first step is to define a loss function. The loss function specifies the objective that the distance metric learning technique or mechanism should optimize. The loss function may be designed to machine-learn the underlying similarity structure of the authorization requests. The loss function may be defined in terms of pairwise distances between authorization requests, or it may be defined using more complex structures, such as graphs or trees.

In an embodiment, the triplet distance metric-based loss function is described as follows: the next step is to train the distance metric learning technique or mechanism. Once the loss function has been defined, the distance metric learning technique or mechanism may be trained using the feature (e.g., fixed-length representation) vectors of the prior authorization requests. The distance metric learning technique or mechanism will learn a distance metric that maps pairs of authorization requests to a scalar value representing their similarity (among approved authorizations and among denied authorizations) or dissimilarity (between approved and denied authorizations).

The next step is to apply the learned distance metric to normalize the feature space. Once the distance metric has been learned, it may be used to transform and normalize the feature space by mapping the feature vectors of the authorization requests to a new space where the distances between authorization requests better reflect their underlying similarity structure. In an embodiment, the distance metric may be applied to the original feature vectors or used to define a new set of features that capture the relevant similarity information. The next step is to use the normalized feature space for tasks of determining recommendations for an incoming authorization request. For instance, by using a distance metric that better reflects the underlying similarity structure of the authorizations, IAS 104 and 302 may achieve better outcomes.

In an embodiment, triplet distance metric learning may be implemented, enabling one to learn a distance metric. Further, the triple distance metric may enable comparing pairs of prior authorization requests in a way that reflects their similarity or dissimilarity in terms of whether they were approved or denied. The above-described approach is based on learning a mapping from the feature space of authorization requests to a distance space, such that the distances between pairs of authorization requests in the distance space reflect their similarity or dissimilarity.

In an embodiment, the triplet distance metric learning formulation may include defining a loss function that may encourage the learned distance metric to preserve the relative distances between triplets of authorization requests. A triplet may include a set of three authorization requests: an anchor authorization request, a positive authorization request, and a negative authorization request. The anchor and positive authorization requests are similar to each other, while the negative authorization request is dissimilar to the anchor authorization request.

The loss function for triplet distance metric learning may be defined as follows.

$$L = \max(0, d(a,p) - d(a,n) + \text{margin}).$$

Where d(a, p) is the distance between the anchor authorization request a and the positive ("Approved") authorization request p in the distance space, d(a, n) is the distance between the anchor authorization request a and the negative ("denied") authorization request n in the distance space, and margin is a hyperparameter that controls the minimum difference between the distances d(a, p) and d(a, n) that must be enforced.

In an embodiment, the objective of the triplet distance metric learning is to learn a mapping from the feature space of authorization requests to the distance space that minimizes the loss function over a set of triplets. This may be done using stochastic gradient descent, where the gradient of the loss function with respect to the parameters of the distance metric is estimated using a small batch of triplets. The learned distance metric may then be used to compare pairs of authorization requests in a way that reflects their similarity or dissimilarity in the recommending correct action (approve or review) for an authorization request.

In an embodiment, to measure the similarity or dissimilarity between the authorization requests, consider three elements: an anchor element, a positive element, and a negative element. The objective of the machine learning models and engines is to learn an embedding space where the anchor element is closer to the positive element and farther away from the negative element. This concept may be applied to authorizing requests related to medical claims by comparing the similarity between a new authorization request and historical authorization requests.

For example, consider a dataset that includes historical authorization requests for medical claims. Each request is represented by a set of features such as claim type, procedure code, diagnosis code, patient age, etc. Based on the authorization decision, each historical authorization request is labeled as either approved or denied.

Now, let us consider whether a new authorization request will be received in real-time. To determine the authorization logic, the triple distance metric may be implemented to find the most similar historical requests and decide based on their outcomes.

Embedding Space: An embedding space may be created where each authorization request is represented as a vector. Machine learning models may learn the embedding space based on historical authorization requests. The embedding space should be learned so that similar requests are closer to each other and dissimilar requests are farther apart.

Triple Selection: For each new authorization request (anchor), select a positive example from the historical requests that have the same authorization outcome (approved or denied). Further, select a negative example from the historical requests that have the opposite authorization outcome. Create triples of (anchor, positive, negative) for training the embedding space.

Loss Function: Define a loss function that encourages the anchor request to be closer to the positive example and farther away from the negative example. For example, a common loss function used for this purpose is the triplet loss, which is defined as:

$$L(\text{anchor}, \text{positive}, \text{negative}) = \max(0, d(\text{anchor}, \text{positive}) - d(\text{anchor}, \text{negative}) + \text{margin})$$

In an embodiment, d (anchor, positive) represents the distance between the anchor and positive example, d (anchor, negative) represents the distance between the anchor and negative example, and margin is a hyperparameter that defines the desired separation between positive and negative examples.

Authorization Logic: When a new authorization request arrives, embed it into the learned embedding space. Compute the distances between the new request and the historical requests in the embedding space. Find the k-nearest neighbors (k-NN) of the new request based on the computed distances. Process and analyze the authorization outcomes of the k-nearest neighbors. Make the authorization decision based on the majority outcome of the k-nearest neighbors or using a weighted scheme.

For example, consider that a new authorization request is received for an outpatient claim with procedure code 1234 and diagnosis code X789. This request may be embedded into the learned embedding space and find its k-nearest neighbors (e.g., k=5) from the historical requests.

The k-nearest neighbors and their authorization outcomes are as follows:

Request 1 (Outpatient, 1234, X789): Approved
Request 2 (Outpatient, 1234, Y456): Approved
Request 3 (Inpatient, 1234, X789): Denied
Request 4 (Outpatient, 5678, X789): Approved
Request 5 (Outpatient, 1234, Z123): Approved Based on the majority outcome of the k-nearest neighbors, the IAS 104 and 302 may authorize the new authorization request as approved. By using the triple distance metric and the learned embedding space, metrics computation engine 420 may effectively compare the similarity between new authorization requests and historical requests to make informed authorization decisions.

In an embodiment, the user management engine 422 may execute operations to manage user accounts, permissions, and access control. The user management engine 422 may implement a mechanism of role-based access control that may enable assigning roles based on user responsibilities. The user management engine 422 may implement mechanisms for executing operations, such as secure login, account management, protecting sensitive information, processing new user accounts, assigning permissions, and controlling access to resources based on roles. The technical advantage of the user management engine 422 is that it enables managing users by maintaining data privacy and data integrity.

In an embodiment, the scenario analysis engine 424 may execute operations for analyzing different context-based scenarios and providing inputs to the other machine learning engines in the IAS 104 and 302. For example, the context-based scenarios may be analyzed to determine any risks associated with the authorization requests, including the medical procedures. The scenario analysis engine 424 may execute operations to create hypothetical situations based on historical data and real-time data. The risk assessment may include evaluating the impact of risk on each scenario and integrating such assessments with the other machine learning engines in the IAS 104 and 302 to evaluate or test the authorization requests. The scenario analysis engine 424 may continually be updated based on new data or changes in the data and be configured to identify potential vulnerabilities and improve IAS 104 and 302 resilience.

In an embodiment, the metrics optimization engine 426 may be configured to execute operations for analyzing the performance metrics of the machine learning engines in the IAS 104 and 302. The metrics optimization engine 426 may implement the execution of multiple machine learning techniques or mechanisms for comparing the current and historical trends and patterns of the data. The metrics optimization engine 426 may modify the IAS 104 and 302 parameters or attributes to influence performance metrics such as accuracy, efficiency, and resource utilization. The technical advantages of the metrics optimization engine 426 may include enhanced adaptability to changing real-time requirements.

In an embodiment, the individual provider trust rating engine 428 may execute operations to provide ratings of individual service providers. For example, the individual provider trust rating engine 428 may collect data on provider outcomes, reliability, historical performance, etc., The individual provider trust rating engine 428 may execute operations to compute and assign trust scores based on multiple criteria. The individual provider trust rating engine 428 may provide an indication or assessment of the trustworthiness in real-time. The trust scores may provide an assessment of provider trustworthiness in real-time, thereby preventing potential issues or circumstances of fraud.

In one embodiment, the performance of individual providers is processed or analyzed and compared against the aggregated performance. Such processing and analysis may enable the identification of gaps in the providers' training or understanding. For instance, if the provider's performance in a specific area, like cardiology authorizations, is lower than the aggregate performance level, the individual provider trust rating engine 428 may indicate a gap in their training or understanding of cardiology. In such cases, feedback may be given to the human operators to retrain the machine learning models, which may be recalibrated or retrained to improve the performance.

In an embodiment, the trust transference engine 430 may execute operations to process and analyze the trustworthiness of the providers based on multiple dimensions. Such analysis may include analyzing the interactions of the providers with the end users and cooperatively working with other machine learning engines to transfer trust based on the processing and analysis and learned patterns. The trust may be transferred from, for example, one provider to another based on the processing and analysis and some criteria. Some technical advantages of the trust transference engine 430 may include the dynamic distribution of trust across the providers, thereby reducing reliance on single providers for trust-related decisions. Further, the trust transference engine 430, in cooperation with the other machine learning engines, may facilitate trust evolution with time. In an embodiment, the trust transference engine 430 may execute operations to map the individual service providers to specific groups based on the trust score of the individual service providers. The trust transference engine 430 may further execute operations to evaluate the trust score of each service provider and may classify or aggregate them into specific groups. The aggregation of the individual service providers to specific groups of providers may influence the trust score associated with the group of providers.

In an embodiment, the trust transference engine 430 may be configured to execute operations to evaluate the trust score of each service provider from the providers' group and execute a decision, for example, to retain or exclude the individual service provider from the group of providers. Further, the trust transference engine 430 may be able to compute or create integrated trust ratings based on the execution of the operations as mentioned above. In an embodiment, the trust transference engine 430 may execute operations to update the trust scores associated with the individual service provider or the group of service providers based on incremental changes or modifications in the data. The influence of the incremental data modifications on the existing trust score may be dynamically learned by the trust transference engine 430 based on real-time data that may include feedback from users.

In an embodiment, the trust rate aging engine 432 may execute operations to manage the trust scores. For example, the trust rate aging engine 432 may execute operations to reduce the weights of historical data in trust score computations by introducing a decay factor. Such a mechanism may ensure or facilitate that the trust score computations are influenced more by up-to-date information or data, thereby reducing the impact of outdated or biased information or data on decision-making. The technical advantages of the trust rate aging engine 432 may include adaptability to changing market conditions and user preferences, minimization of the risk of overreliance on past performance, and enhancement of overall trust dynamics.

In an embodiment, the data pre-processing engine 434 may execute operations for cleaning, transforming, and structuring raw input data from multiple data sources. For example, the raw input data from the multiple data sources are described in reference to FIG. 1 and FIG. 2. The data pre-processing engine 434 may include a data ingestion module (not shown) that may be configured to execute operations of receiving data from multiple sources in different formats. For example, the data may be structured, semi-structured, unstructured, etc., and may be received through APIs or files. The data pre-processing engine 434 may execute operations to standardize the data types and remove inconsistencies to ensure consistency across the machine learning models. The data pre-processing engine 434 may identify relevant features from raw data for implementing machine learning techniques or mechanisms. The data pre-processing engine 434 may execute operations to ensure compliance with privacy regulations by removing personally identifiable information (PII). The data pre-processing engine 434 may execute operations that may include removing duplicates, missing values, and outliers, converting categorical variables to numerical or binary formats, and creating new features from existing ones for improved model performance. The technical advantage of the data pre-processing engine 434 is efficient data pre-processing that enables the machine learning models to learn from high-quality input, reducing bias and improving accuracy.

In an embodiment, the rendering engine 436 may be configured to execute operations in cooperation with the other machine learning engines, for example, the UI engine, to convert data from various formats to visual representations for easy understanding. For instance, the rendering engine 436 may display charts, graphs, and other forms of visualization based on the execution of operations by the machine learning engines in the IAS 104 and 302. For example, such visualizations may be related to trust rating, decisions related to authorization requests, recommendations for rejecting or denying authorization requests, and the like. The visualizations rendered by the rendering engine 436 may enhance the interpretation of complex information.

In an embodiment, the decision-making engine 438 may execute operations to integrate the results of the execution of the other machine learning engines in the IAS 104 and 302 to make or interpret decisions related to authorization requests. The decision-making engine 438 may implement the execution of logical rules, techniques, or mechanisms and learned patterns to approve, reject, or provide recommendations with reference to the authorization requests. The technical advantages of the decision-making engine 438 may include an automated, efficient decision-making process with consistent application of the learned patterns and knowledge. The decision-making engine 438 may also be configured to execute operations that adapt to changing authorization policies and patterns associated with the authorization requests.

In an embodiment, the rules engine 440 may be configured or adapted to work with, for example, other machine learning engines in the IAS 104 and 320. The rules engine 440, in the context of medical claims authorization, may execute operations to streamline and automate the process of evaluating and approving, denying, flagging for review, or redirecting the claims to Medicare or Medicaid for a further review based on a complex set of predefined rules and criteria. The rules engine 440 may be configured to execute operations based on multiple parameters, including Medicare and Medicaid regulations, provider-specific guidelines, patient history, and other relevant factors.

In an embodiment, the rules engine 440, in cooperation with the automated learning model 410, may execute operations to learn the knowledge base that encapsulates all the necessary rules, policies, and guidelines related to medical claims authorization. These rules are derived from various sources, such as government regulations, insurance company policies, and healthcare provider practices. The knowledge base is continually updated to ensure that the rules engine 440 remains current and compliant with the latest standards and requirements.

In an embodiment, the rules engine 440 implements advanced machine learning techniques or mechanisms, such as decision trees, random forests, and neural networks, to process and analyze incoming claims data and authorization requests to determine whether a claim or authorization request may be approved, denied, flagged for review, or redirected to other authorities for further scrutiny.

In an embodiment, the rules engine 440 may be automatically adapted to configure and reconfigure rules based on various parameters. For example, if a new Medicare regulation is introduced, the rules engine 440 may be updated to incorporate the new rule into its decision-making process. Similarly, if a healthcare provider's trust rating changes based on their performance or patient feedback, the rules engine 440 may adjust its authorization criteria accordingly.

To illustrate the implementation of the rules engine 440, let us consider an example scenario involving the trust transference engine 430 and the individual provider trust rating engine 428. Suppose a patient submits a claim for a knee replacement surgery performed by a specific healthcare provider. The rules engine 440 may execute operations to retrieve all relevant rules and guidelines related to knee replacement surgeries, including Medicare and Medicaid regulations, the provider's specific policies, and any applicable patient-specific factors.

The rules engine 440 may cooperatively work with the trust transference engine 430 to gather additional information about the healthcare provider. The trust transference engine 430 may execute operations to process and analyze the provider's historical performance data, patient feedback, and other relevant metrics to assign a trust rating to the provider. This trust rating is then fed into the rules engine 440, which uses it as one of the factors in its decision-making process.

In an embodiment, the rules engine 440 may collaborate with the individual provider trust rating engine 428 to assess the healthcare provider's overall trustworthiness and reliability. The individual provider trust rating engine 428 may consider a broader set of factors, such as the provider's adherence to best practices, their record of successful outcomes, and their reputation within the medical community. The resulting trust rating is also incorporated into the rules engine's 440 evaluation process.

Based on the comprehensive processing and analysis of all relevant factors, including the applicable rules and regulations, the patient's medical history, the provider's trust rating, and the provider's overall trustworthiness, the rules engine 440 provides inputs to the decision-making engine 438 to determine whether to approve or deny or flag for review or redirect the claim to Mediclaim or Medicare for further scrutiny of the authorization request or claim for the knee replacement surgery. If approved, the authorization request or claim is processed, and the appropriate payments are authorized. If denied, IAS 14 and 302 generate or create a detailed explanation of the reasons for the denial, which may be communicated to the patient and the healthcare provider.

In an embodiment, the rules engine 440 maintains an elevated level of transparency and audibility, ensuring that all decisions are based on objective criteria and may be easily traced and reviewed if necessary. The IAS 104 and 302 may continuously learn and adapt based on feedback and outcomes, thereby enabling them to refine their decision-making capabilities over time and improve the accuracy and efficiency of the medical claims authorization process.

FIG. 5 is a block diagram 500 showing an illustration of an electronic format of an authorization form, according to an exemplary embodiment. FIG. 5 is an illustration showing a block diagram 500 of an electronic form for making authorization requests. In an embodiment, the electronic form may be represented as a table, including, for example, multiple data fields represented by the columns of the table. The data fields represented by the columns may include authorization number (e.g., Auth #), date, age, service request 1 (CPT1), service request 2 (CPT2), associated diagnosis 1 (ICD1), associated diagnosis 2 (ICD2), etc. FIG. 5 shows that the authorization request includes multiple service requests. For instance, each service request may correspond to a patient's diagnosis and treatment. For example, the service requests may be related to surgical procedures, medical procedures, pre- and post-procedure tests, and diagnostic procedures, such as X-rays, blood tests, MRIs, etc.

FIGS. 6A, 6B, and 6C respectively show block diagrams 600A, 600B and 600C that illustrate a splitting mechanism of an authorization request into multiple service requests, according to an exemplary embodiment. FIGS. 6A, 6B, and 6C are described in conjunction with FIGS. 1-5. FIG. 6A is a block diagram 600 showing an illustration of an authorization request in the electronic format, as shown and described with reference to FIG. 5. In an embodiment, the electronic format of the authorization request 600A may be split or divided into two or more authorization requests (e.g., 600B and 600C) based on a criterion. For example, FIG. 6B and FIG. 6C are such illustrations showing the splitting of the authorization request shown in FIG. 6A. In an embodiment, each row of the table (e.g., shown in FIG. 6A) that corresponds to the authorization request may include one or more service requests. The service requests may be associated with a single patient based on the patient's health condition and the initial diagnosis. Each authorization request (AR) may include multiple services. The request may be divided or split into multiple service requests (SR), each service request focusing only on one service. In an embodiment, the AR consisting of two or more service requests may be split into multiple single service requests so that each service request may be considered for recommendation individually.

FIG. 7A is a block diagram 700 illustrating a table including CPT® codes, according to an exemplary embodiment. FIG. 7A is a block diagram 700 showing an illustration of a table including CPT® codes. The table includes the CPT® code, a corresponding description of the service, and associated costs (e.g., Fee) for each service. The Current Procedural Terminology (CPT®) codes are a standardized system of five-digit numerical codes used by healthcare providers to report medical, surgical, and diagnostic procedures they perform. CPT® codes are essential for billing and reimbursement by insurance companies and government programs like Medicare and Medicaid. They are maintained by The American Medical Association (AMA). In an embodiment, the CPT® Code Structure may be organized into 3 categories.

Category I: The most common codes representing widely accepted medical procedures and services.

Category II: Supplemental codes used for performance measurement and tracking.

Category III: Temporary codes for emerging technologies and procedures.

Category I CPT® codes are divided into sections: Anesthesia (00100-01999, 99100-99140); Surgery (10004-69990); Radiology (70010-79999); Pathology and Laboratory (80047-89398); Medicine (90281-99607); Evaluation and Management (99202-99499).

Figure 7B:
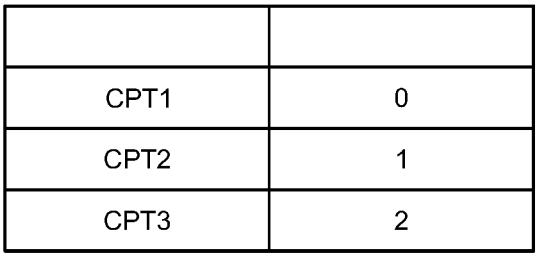
FIG. 7B is a block diagram showing an illustration of a fixed-length representation of CPT® encoding, according to an exemplary embodiment.

FIG. 7B is a block diagram 700B showing an illustration of a fixed-length representation of CPT® encoding, according to an exemplary embodiment. FIG. 7B is described in conjunction with FIGS. 1-4. FIG. 7B is a block diagram 700B showing the illustration of a table including a fixed-length representation of CPT® encoding. FIG. 7B shows the fixed-length coding referred to as one-hot-encoding. Specifically, the fixed-length representation relies on assigning a unique numeric identifier to the presence of a categorical variable. For example, the presence of service request CPT3 will be encoded as position "2," as illustrated in FIG. 7B.

In an embodiment, one-hot encoding is a technique used to convert categorical variables into a binary vector representation. In one-hot encoding, each unique category is represented by a binary vector where only one element is set to 1 (hot), and all other elements are set to 0. This encoding scheme creates a separate binary feature for each category, enabling the machine learning models and the machine learning engines to process categorical data effectively. The one-hot encoding technique is implemented by the intelligent authorization engine 412, as described in FIG. 4.

In an embodiment, one-hot encoding may have multiple technical advantages. For example, the one-hot coding technique may enable machine learning models and machine learning engines to process categorical data effectively since it converts categories into numerical features. Further, one-hot encoding avoids introducing any ordinal relationship between categories, as each category is represented independently. Further, one-hot encoding enables easy comparison and matching of categorical values during the authorization process. In an embodiment, one-hot encoding, combined with fixed-length encoding, provides a structured and efficient way to represent and process categorical variables in authorization requests for the IAS 104 and 302.

Figure 7C:
FIG. 7C is a block diagram showing an illustration of a fixed-length representation of CPT® encoding, according to an exemplary embodiment.

FIG. 7C is a block diagram showing an illustration of a fixed-length representation of CPT® encoding, according to an exemplary embodiment. FIG. 7C is described in conjunction with FIGS. 1-4. FIG. 7C is a block diagram 700C showing the illustration of a table including a fixed-length representation of CPT® encoding. For example, the presence of service requests CPT1 and CPT3 in an authorization request will be encoded by the value "1" in the first (0th) and third (2nd) positions. The absence of the CPT2 code is encoded by the value "0" in the second (1st) position, as illustrated in FIG. 7C.

FIG. 8A is a block diagram 800A showing an illustration of a table of sample ICD codes, according to an exemplary embodiment. FIG. 8A is a block diagram 800A showing an illustration of a sample of International Classification of Diseases (ICD) codes. The table includes codes and a concise description of diseases that may be used for the classification of diseases. The ICD codes are a comprehensive system of codes used globally to represent a vast range of diseases, injuries, symptoms, and other health conditions. Developed and maintained by the World Health Organization (WHO), ICD codes provide a shared language for medical professionals, researchers, and health insurers. The standardization offered by ICD codes has several critical applications.

Reimbursement and Billing: Healthcare providers rely on ICD codes to document diagnoses accurately, justify the medical necessity of procedures, and ensure appropriate reimbursement from insurance companies.

Global Health Analysis: ICD codes help us track disease prevalence, mortality rates, and patterns of health and illness across populations worldwide. This data is vital for public health initiatives and policy decisions.

Healthcare Research: Researchers use ICD codes to analyze large datasets, identifying potential risk factors, treatment efficacy, and long-term disease trends.

Communication: ICD codes bridge the gap between different healthcare systems and providers, ensuring clear and consistent communication about diagnoses and patient histories.

In an embodiment, ICD codes may provide critical knowledge on the extent, causes, and consequences of human disease and death worldwide via data that is reported and coded with the ICD. Clinical terms coded with ICD are the main basis for health recording and statistics on disease in primary, secondary, and tertiary care, as well as on cause of death certificates. These data and statistics support payment systems, service planning, administration of quality and safety, and health services research. Diagnostic guidance linked to categories of ICD also standardizes data collection and enables large-scale research.

Figure 8B:
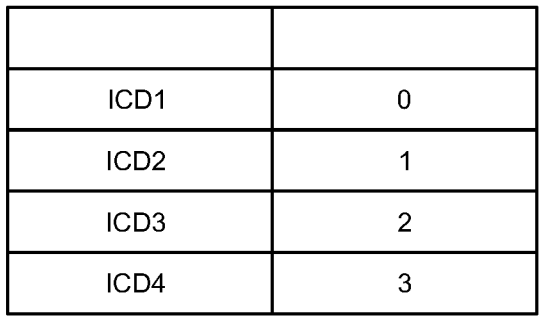
FIG. 8B is a block diagram showing an illustration of a fixed-length representation of ICD coding, according to an exemplary embodiment.

FIG. 8B is a block diagram 800B showing an illustration of a fixed-length representation of ICD coding, according to an exemplary embodiment. FIG. 8B is a block diagram 800B showing an illustration of a table including a fixed-length representation of the ICD coding. Specifically, the fixed-length representation relies on assigning a unique numeric identifier to the presence of a categorical variable. This is like the CPT code as shown and described in FIG. 7B.

Figure 8C:
FIG. 8C is a block diagram showing an illustration of a fixed-length representation of ICD coding, according to an exemplary embodiment.

FIG. 8C is a block diagram 800C showing an illustration of a fixed-length representation of ICD coding, according to an exemplary embodiment. FIG. 8C is a block diagram 800C showing an illustration of a table including a fixed-length representation of the ICD coding. For example, the presence of service requests ICD2 and ICD4 in an authorization request will be encoded by the value "1" in the second ($1^{st}$) and fourth ($3^{rd}$) positions. The absence of the ICD code is encoded by the value "0" in the first ($0^{th}$) position and third ($2^{nd}$) position, as illustrated in FIG. 8C.

Figures 9A, 9B, 9C:
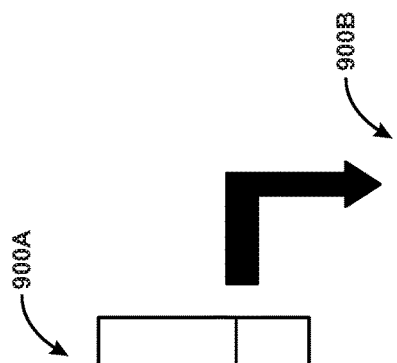
FIGS. 9A, 9B, and 9C illustrate the splitting of service requests according to an exemplary embodiment.

FIGS. 9A, 9B, and 9C are illustrations showing the splitting of service requests, according to an exemplary embodiment. FIGS. 9A, 9B, and 9C respectively show block diagrams 900A, 900B and 900C including the splitting of service requests based on ICD and CPT® codes. In an embodiment, FIG. 9A illustrates the splitting of an authorization request having multiple service (CPT) requests into multiple service requests, each with one single service request. For instance, FIG. 9A illustrates a single authorization request with two (e.g., CPT1=97161 and CPT3=99215) service requests that have been split into two service requests, as illustrated in FIG. 9C, in which the first service request is with a single service, for example, CPT1=97161, and the second is with a single service request, CPT3=99215. In an embodiment, each service request is represented by fixed-length representations that are derived from FIG. 9B, as shown and described in FIGS. 7A to 8C, respectively.

Figure 10:
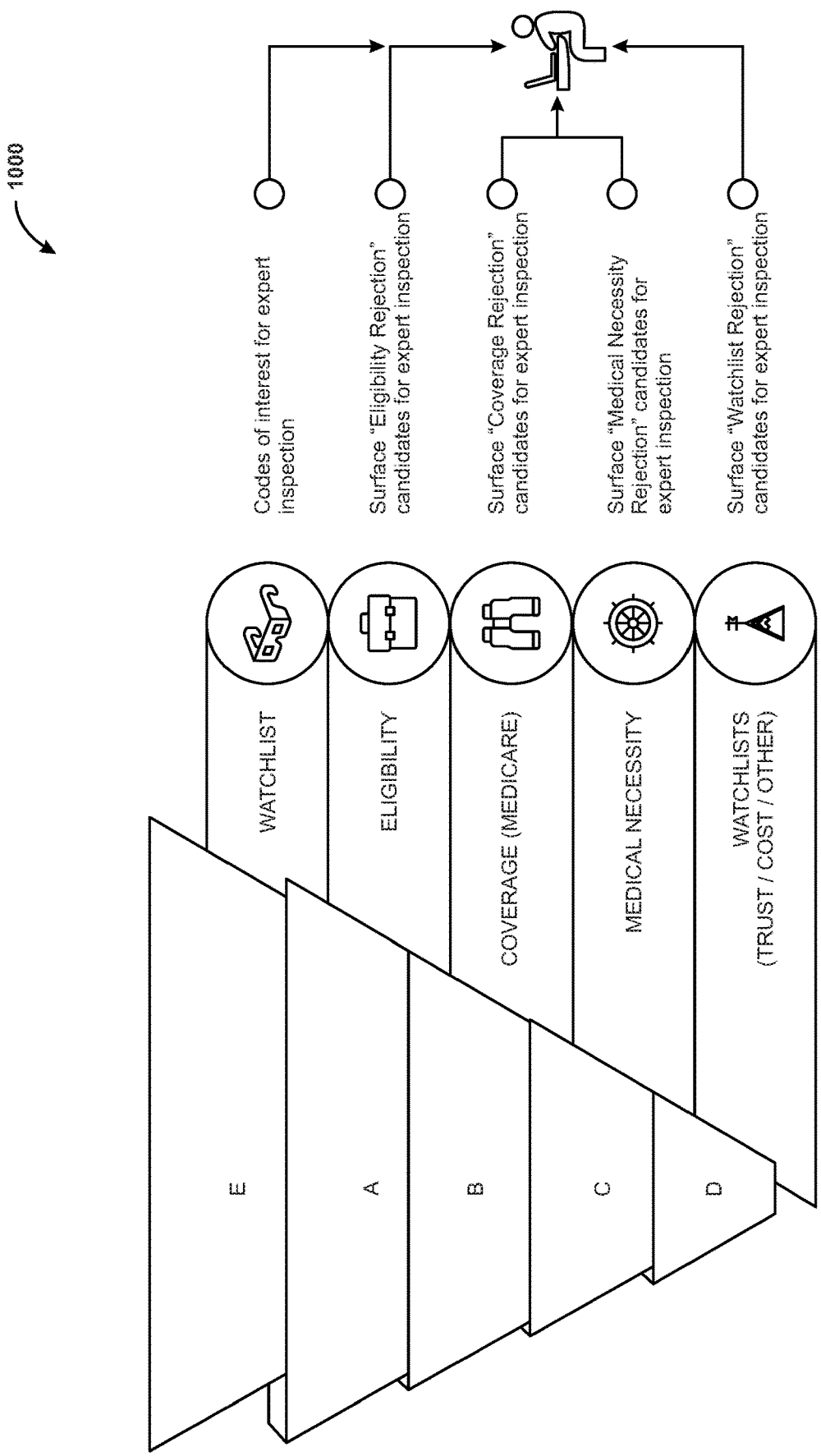
FIG. 10 is a block diagram showing an implementation of the IAS based on classifier models, according to an exemplary embodiment.

FIG. 10 is a block diagram 1000 showing an implementation of the IAS based on classifier models, according to an exemplary embodiment. FIG. 10 is described in conjunction with FIGS. 1-4. FIG. 10 is a block diagram 1000 showing an illustration of an implementation of the IAS 104 and 302 based on classifier models. Such classifier models may be implemented based on machine-learned classifier models or rule-based models, for example. Such machine-learned classifier models or rule-based models may be developed by training the machine learning models using the machine learning engines in the IAS 104 and 302. In an embodiment, implementing the machine-learned classifier models or rule-based models may facilitate or enable the IAS 104 and 302 to execute operations by automating assessments by combining various modeling techniques. For example, the machine-learned classifiers or attributes that may be used may include watchlist, eligibility, coverage (Medicare), medical necessity, and other factors such as trust, cost, other factors, etc. FIG. 10 shows an illustration where the classifiers are cascaded. The IAS 104 and 302 may implement the execution of operations based on the cascaded classifiers and may either approve, deny, or provide recommendations for further review of the authorization requests.

In an embodiment, the cascaded classifier establishes a sequential decision evaluation in stages to streamline the authorization of requests. Each stage represents a specific criterion, and the machine learning engines are trained on the classifiers and may represent the machine-learned classifiers. In an embodiment, the watchlist may correspond to codes of interest for expert inspection. For example, consider the following.

Eligibility—The machine learning engines in the IAS 104 and 302 are trained using classifiers, such as patient demographic data, insurance plan details, etc. These engines may determine whether the patient is even eligible for the claimed service.

Coverage—The machine learning engines in the IAS 104 and 302 are trained on classifiers, such as insurance policy rules, procedure codes, and diagnosis codes. The IAS 104 and 302 execute operations to verify whether the claimed service is covered under the patient's plan.

Medical Necessity—The machine learning engines in the IAS 104 and 302 are trained using classifiers, such as medical guidelines, clinical data, and treatment histories. The IAS 104 and 302 execute operations to determine whether the service is medically necessary for the patient's condition.

Trust Model—The machine learning engines in the IAS 104 and 302 are trained using classifiers, for example, on historical authorization requests, approvals or denials of authorization requests, authorization request patterns, provider reputation, provider trust score, and fraud indicators. The machine learning engines in IAS 104 and 302 execute operations to evaluate the trustworthiness of the authorization requests to identify potentially fraudulent activity.

Cost—The machine learning engines in the IAS 104 and 302 are trained using classifiers, such as market rates, standard fees, and cost outliers. They may analyze whether the requested cost is reasonable and customary.

In an embodiment, a healthcare provider submits an insurance claim or authorization request for services rendered or for rendering the services. The claim enters the cascaded classifier mechanism that the IAS 104 and 302 implement and execute operations. Eligibility Check: The stage 1 classifier quickly determines basic eligibility. If ineligible, the claim is rejected, providing fast feedback to the provider. Coverage Assessment: If eligible, the Stage 2 classifier checks if the procedure is covered. If covered, the claim is accepted with an obvious reason. Further Analysis: If covered, the claim continues through the cascade. Each subsequent stage adds a layer of scrutiny. Final Determination: If the claim passes all stages, it is likely to be authorized. If the claim fails at any stage, it might be rejected, flagged for further review, or redirected to Medicaid or Medicare for further scrutiny or payment amounts adjusted.

Figure 11:
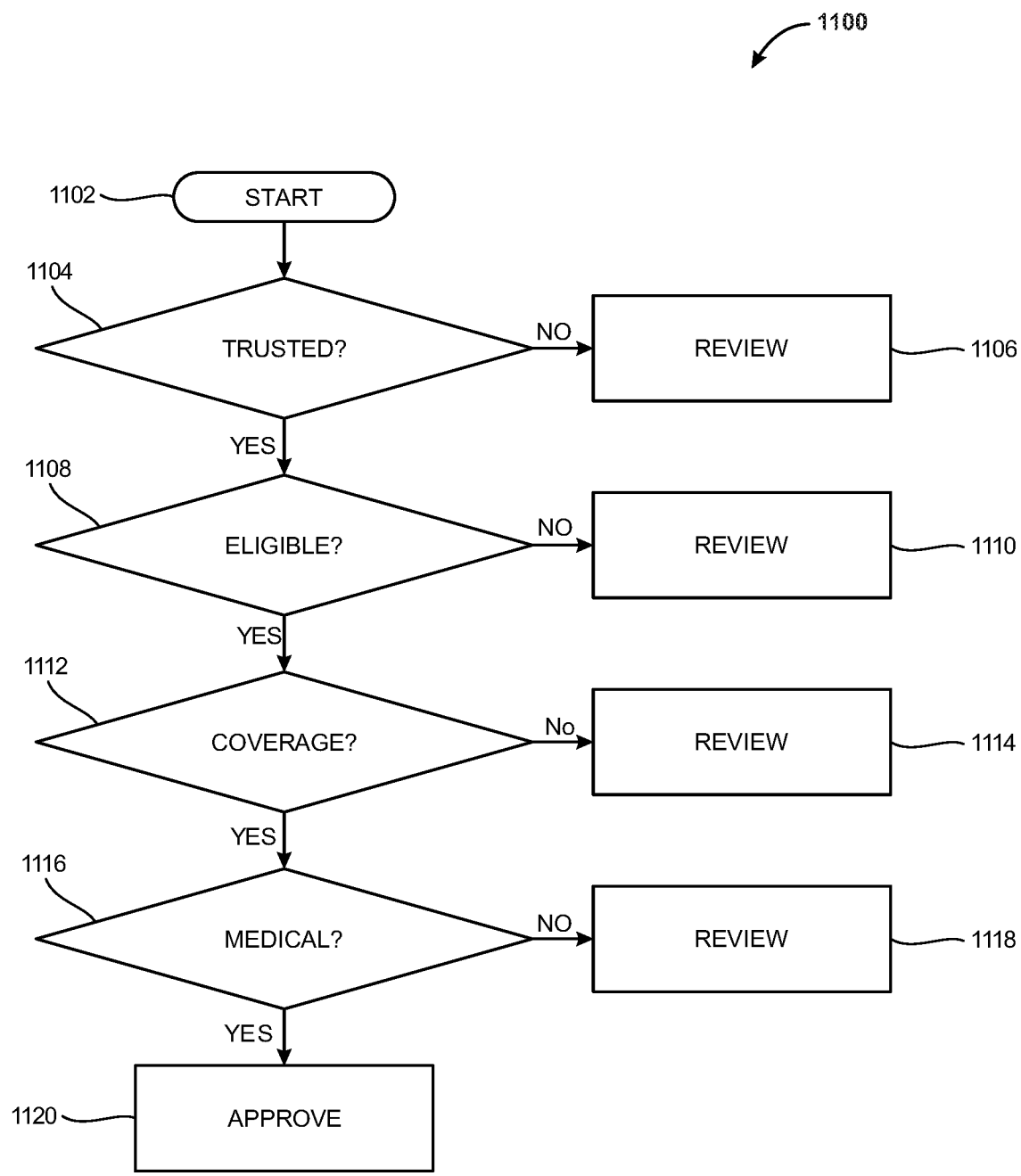
FIG. 11 is a flow diagram illustrating a process of evaluation and disposition of authorization requests using the classifier models, according to an exemplary embodiment.

FIG. 11 is a flow diagram illustrating process 1100 of evaluation and disposition of authorization requests using the classifier models, according to an exemplary embodiment. FIG. 11 is described in conjunction with FIGS. 1-4 and FIG. 10. FIG. 11 illustrates a process 1100 of evaluating the authorization requests using the implementation of the classifier models by the IAS 104 and 302 as shown and described in FIG. 10. The IAS 104 and 302 may execute operations to determine whether the service requests may be evaluated and disposed of based on multiple attributes, parameters, or criteria, as shown, and described in FIG. 10. The process 1100 begins at step 1102 and may include multiple validation steps (e.g., trusted 1104 provider, eligible 1108, coverage 1112, e.g., insurance coverage). The validation process is sequential and proceeds to the next step only upon successful (YES) validation of the previous step. When the validation of the authorization request fails at any step (NO), the service request may be flagged for review (e.g., 1106, 1110, 1114, and 1118) by IAS 104 and 302. If all the validation steps are successful, the authorization requests may be recommended for approval.

In an embodiment, the IAS 104 and 302 start processing the authorization requests at step 1102. The next step, at 1104, is assessing whether a provider submitting the input authorization request is trusted. If true, process 1100 proceeds to evaluate or determine whether the patient related to the authorization request is eligible to receive the service (i.e., whether the patient is eligible to receive the service on the date of the request) in step 1108. If true, process 1100 proceeds to determine or evaluate whether the service being requested is covered in step 1112. If true, process 1100 proceeds to determine or evaluate whether the specific service being requested is a medical necessity in step 1116. If true, the IAS 104 and 302 will recommend the authorization request for approval. In all other cases (at each step including 1104, 1108, 1112, and 1116 when the determination or evaluation fails (NO)), the IAS 104 and 302 recommend the authorization request be reviewed (e.g., 1106, 1110, 1114, and 1118) by the human reviewer. The IAS 104 and 302 may have an arbitrary number of validation steps and may be customized based on the overall context of the provider, patient, payor, or other global contexts. Further, each downstream validation step may be customized based on the collective context of outcomes of previous validation steps. The validation steps shown in FIG. 11 are sequential, but they may be implemented in parallel. The overall validation may be undertaken in a single step based on the collective information available.

In an embodiment, each of the evaluation or determination steps (e.g., 1104, 1108, 1112, and 1116) may be implemented using either a rule-based or based on a machine-learned model. The rules may be designed machine learned. Depending on which classifier is being employed for the given validation, the authorization requests are differently organized as cohorts. For example, all authorization requests requesting a specific CPT service (e.g., 97161) constitute CPT-97161 cohorts and facilitate learning the model that recommends approval/review action for an input service requesting 97161 services.

Figure 12A:
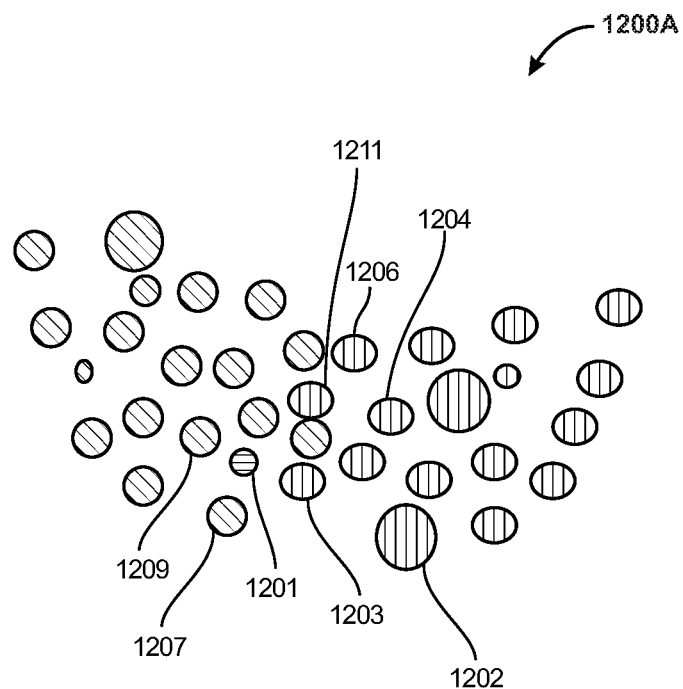
FIG. 12A is a block diagram showing an illustration of a collective representation of the authorization requests, according to an exemplary embodiment.

FIG. 12A is a block diagram 1200 showing an illustration of a collective representation of the authorization requests, according to an exemplary embodiment. FIG. 12A, each dot in FIG. 12A may represent an authorization request. The authorization requests labeled as 1203, 1209, 1207, 1201, and 1211 may, for example, correspond to or represent the prior authorization requests that have been successfully authorized (e.g., approved). The authorization requests labeled 1206, 1204, and 1202 may represent authorizations that may be denied or may be flagged for review or redirected to Medicaid or Medicare for further scrutiny. In an embodiment, the authorization requests labeled 1206, 1204, and 1202 may represent authorizations that may require further review and may provide information for denial or rejection that may necessitate a further review. The size of the dot reflects a measurement of the credibility/reliability of the source of the data point. The authorization requests are shown in FIG. 12A and may include multidimensional information.

For example, the multidimensional information may include various attributes of the authorization request, including the medical condition, service being requested, and age of the patient, and other global contexts of the request, including social determinants of the health of the patient, patient's medical history, results of the medical tests performed, etc. In an embodiment, a transformation function or mechanism (e.g., transformation 1) may be applied to the information present in the authorization request, and the machine learning engines in the IAS 104 and 302 may generate or create visualizations and render them on the UI for consideration for data exploration. In an embodiment, the transformation function or mechanism may be rule-based or machine-learned. For example, when the transformation function or mechanism is implemented, only the first few major principal components suggested by principal component analysis of the distribution of the authorization request representations may be retained. Further, the transformation mechanism may be a machine-learned representation such as an auto-encoder.

Figure 12B:
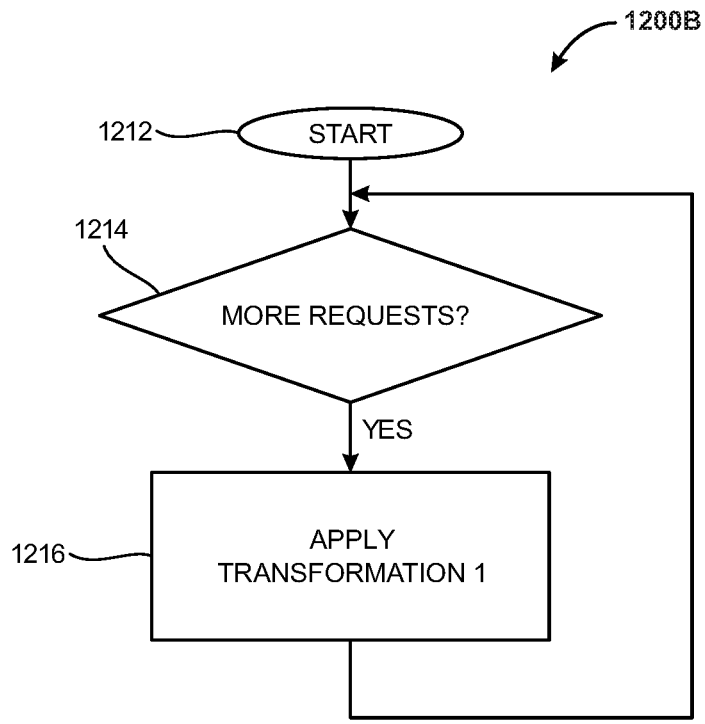
FIG. 12B is a flow diagram illustrating a process for authorization requests, according to an exemplary embodiment.

FIG. 12B is a flow diagram illustrating a process 1200B for authorization requests, according to an exemplary embodiment. FIG. 12B is described in conjunction with FIGS. 1-4 and FIG. 12A. FIG. 12B illustrates a process 1200B for processing authorization requests based on, for example, some criteria. Process 1200 may include evaluating the authorization requests, making computations based on the evaluations, applying transformations based on the computations, and making decisions on whether to authorize or deny the requests. In an embodiment, the process starts at step 1212. At step 1214, the IAS 104 and 302 may check or determine whether there are any pending authorization requests. At step 1216, the transformation function is shown and described in FIG. 12A is applied if true (YES). IAS 104 and 302 implement the transformation function on each authorization request with transformation 1 to obtain a collective representation of a collection of the authorization requests, as shown in FIG. 12A.

FIGS. 13A and 13B are illustrations showing the implementation of the machine learning model by the IAS for authorizing requests, according to an exemplary embodiment. FIGS. 13A and 13B are described in conjunction with FIGS. 1-4, FIG. 12A and FIG. 12B. FIGS. 13A and 13B show illustrations, including a collective initial representation of the authorization request (e.g., 1307). As described with reference to FIG. 2 and FIG. 3, the machine learning engines train the machine learning models, and the IAS 104 and 302 may execute operations for authorization of requests in real-time. In an embodiment, the dots in FIG. 13A may represent historical or prior authorization requests, while the dots in FIG. 13B may represent authorization requests (e.g., 1302, 1302, 1311, 1304) received in real-time. The authorization requests, as shown in FIG. 13B may represent adjusting the dimensions to improve the efficacy of the model to distinguish approved authorization requests from denied authorization requests by stretching the individual dimensions and data point representations appropriately. In an embodiment, the transformation function, as shown and described in FIGS. 12A and 12B, may be applied to transform the initial authorization request representation to the final authorization request.

Figure 14A:
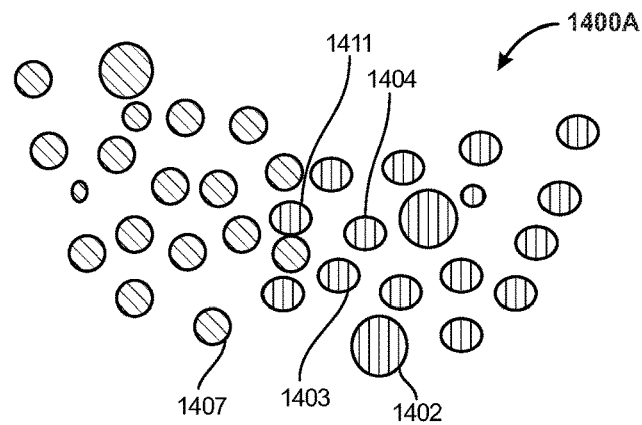
FIGS. 14A and 14B illustrate a collective representation of historical authorization requests to train the IAS, according to an exemplary embodiment.
Figure 14B:
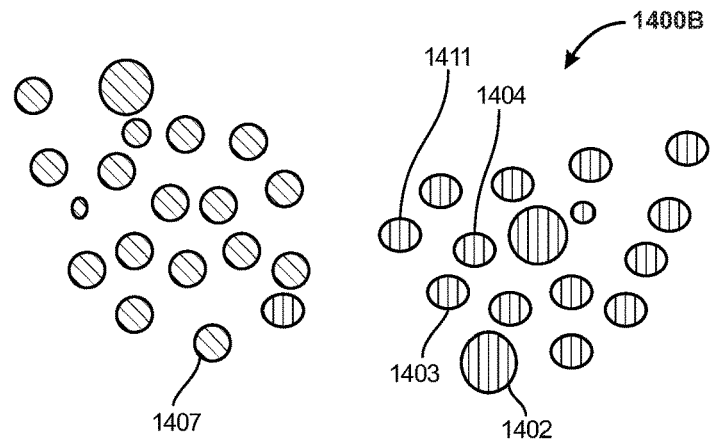

FIGS. 14A and 14B are illustrations showing a collective representation of historical authorization requests to train the IAS, according to an exemplary embodiment. FIGS. 14A and 14B are illustrations showing a representation of authorization requests. The collective representation of the authorization requests shown in the close vicinity of labeled 1407 and 1411 may represent the historical requests that have been successfully authorized (e.g., approved). The collective representation of the authorization requests in the close vicinity of 1402, 1403, and 1404 may represent authorization requests that may be denied or may require further review. In an embodiment, the authorization requests in the close vicinity of 1402, 1403, and 1404 may represent authorizations that may require further review and may provide information for denial that may need a further review.

In an embodiment, the authorization requests are represented by dots with diagonal lines in FIG. 14A shows the collective representation of the historical authorization requests constituting the training data for IAS 104 and 302. In FIG. 14B, the authorization requests represented by dots with diagonal lines represent the collective final representation of the historical authorization requests constituting the training data for IAS 104 and 302 in FIG. 14A, the authorization requests represented by dots with vertical lines (e.g., 1402, 1403, 1411) show a single prior authorization request (which happens to be denied). In an embodiment, upon applying a transformation function, for example, transformation 2, the authorization requests were transformed.

In an embodiment, when the IAS 104 and 302 implement the above-referenced transformation function, thereby providing information about the authorization requests. In an embodiment, the dots representing the authorization requests or the data points may be: (a) randomly sampled, i.e., each data point is equally likely to be selected in the final representation; (b) sampled based on their criticality to the decision making; (c) Sampled based on importance, for example, the trustworthy data points get sampled more frequently than the less trustworthy data points.

Figure 14C:
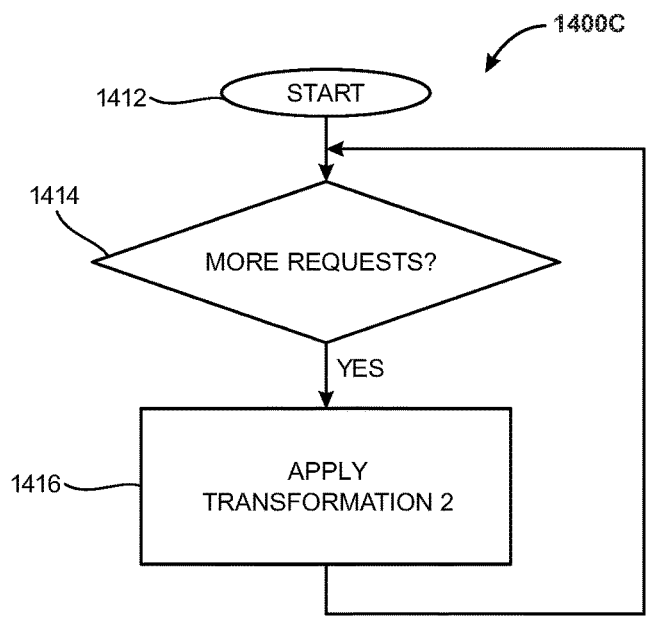
FIG. 14C is a flow diagram showing a process of representing a final authorization, according to an exemplary embodiment.

FIG. 14C is a flow diagram showing a process 1400C of representing a final authorization, according to an exemplary embodiment. FIG. 14C is described in conjunction with FIGS. 1-4, and FIGS. 12A-14B. FIG. 14 is an illustration showing a process 1400C for authorizing requests, for example, based on certain criteria. The process 1400C may include evaluating the requests, making computations based on the evaluations, applying transformations based on the computations, and making recommendations as to whether to authorize or deny the requests. The IAS 104 and 302 may implement the steps of the process 100C. At step 1412, the process 1400C starts execution. The IAS 104 and 302 may implement previously learned information from the training data and implement the execution of operations. At step 1414, the IAS 104 and 302 checks if there are more requests. The IAS 104 and 302 may apply previously implemented transformation (e.g., transformation 2) at step 1416. A collective representation may be created or generated and rendered or displayed on the UIs that may represent the cohorts based on the application of the transformation function (e.g., transformation 2).

Figure 15B:
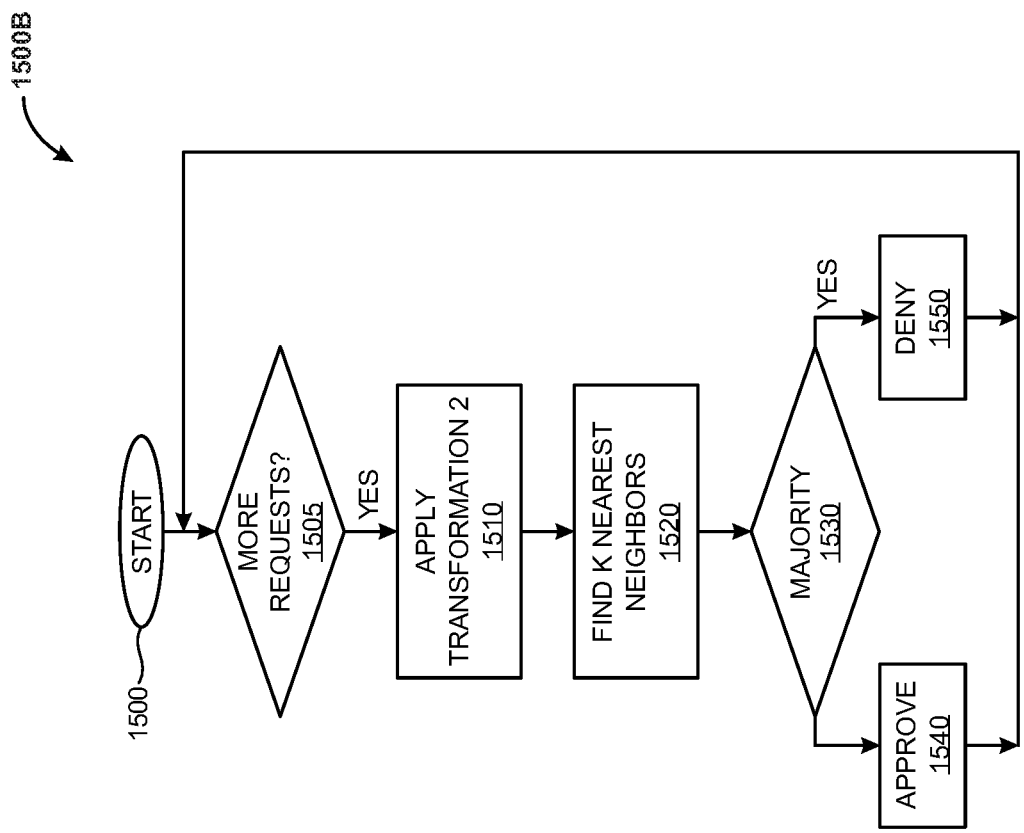
FIG. 15B is a flow diagram illustrating a process for recommending action for the authorization request, according to an exemplary embodiment.
Figure 15A:
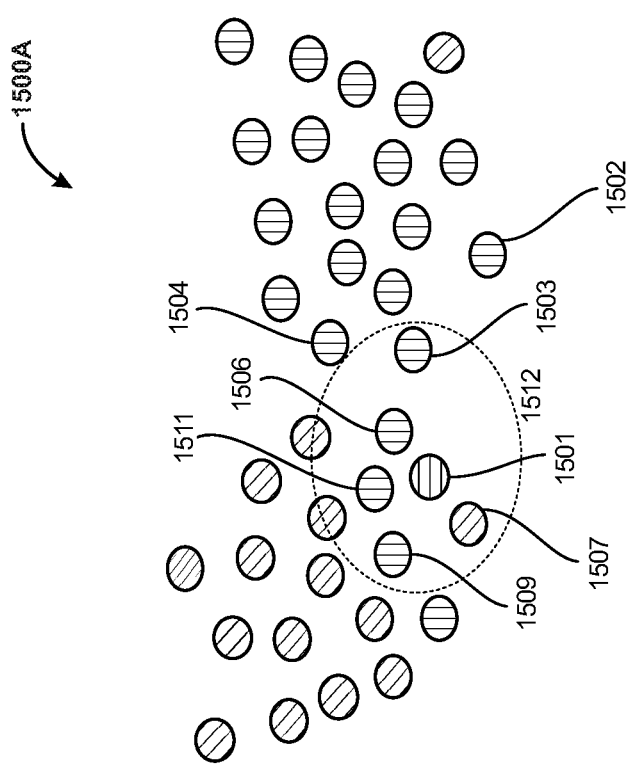
FIG. 15A illustrates a recommendation for action regarding the authorization request, according to an exemplary embodiment.

FIG. 15A is an illustration representing a recommendation of an action for the authorization request, according to an exemplary embodiment. FIG. 15A is described in conjunction with FIGS. 1-4. FIG. 15A is an illustration showing a collective representation of the authorization requests. The authorization requests represented as dots labeled 1511, 1509, 1507, and 1506 may correspond to the authorization requests that have been successfully approved. The authorization requests represented as dots labeled 1504, 1503, and 1302 may represent authorizations that may be denied, or that may be flagged for review or redirected to Medicaid or Medicare for further scrutiny. In an embodiment, the authorization requests represented as dots labeled 1504, 1503, and 1502 may represent authorizations that may require further review and may provide information for denial that may need a further review. The authorization request corresponding to the dot represented by 1501 may represent the authorization request whose disposition needs to be determined by applying the nearest neighbor decision logic. For example, the decision logic may be based on parameters, attributes, etc., associated with the authorization requests that may have been approved or denied previously.

For example, in order to determine the recommendation for authorization request 1501, IAS 104 and 302 may execute operations to determine k-nearest neighbors to authorization request 1501 in the representation space. The IAS 104 and 302 may determine or look for a certain number of predetermined K-nearest neighbors. For example, the nearest neighbors may be, for k=5. In such cases, IAS 104 and 302 may check for 5 nearest neighbors. In this illustration, the system may determine that the authorizations represented by 1507, 1509, 1506, and 1511 may qualify as the nearest neighbors of the authorization request 1501. Note that of the 5 neighbors, 4 neighbors (e.g., 1506, 1511, 1507, 1509) represent prior authorizations that have been previously approved, while one neighbor (i.e., 1503) represents an authorization that has been previously denied. Since the majority of the authorizations selected in the nearest neighborhood have been approved, IAS 104 and 302 may determine to recommend the authorization request corresponding to 1501 for approval. The number of neighbors to be used by the IAS 104 and 302 for the determination of the recommendation may be fixed or dynamic. Additional parameters may be included, such as the maximum neighborhood radius (1512) within which k neighbors are selected. This parameter may be changed based on the authorization representation and tuned based on the desired KPI objects and representative authorization datasets.

FIG. 15B is a flow diagram illustrating a process 1500B representing a recommendation of action for the authorization request, according to an exemplary embodiment. FIG. 15B is described in conjunction with FIGS. 1-4, FIG. 14C and FIG. 15A. FIG. 15B is an illustration showing a process 1500B representing a recommendation of action for the authorization request, according to an exemplary embodiment. The process 1500B may include evaluating the requests, making computations based on the evaluations, applying transformations based on the computations, and deciding whether to authorize or deny the authorization requests. In an embodiment, the process 1500B may be implemented by the machine learning engines in the IAS 104 and 302. The process 1500B may further include determining the nearest neighbor, for example, the K-Nearest neighbor, based on an implementation of decision logic. For example, the decision logic may be based on parameters, attributes, etc., associated with authorizations that may have been approved or denied previously. The process 1500B starts at step 1500. At step 1505, the IAS 104 and 302 may determine if there are more authorization requests. The process 1500B proceeds to step 1510 upon confirmation of the more requests (YES). At step 1510, the transformation function, for example, transformation 2, may be executed, as described with reference to FIG. 14C. At step 1520, k-nearest neighbors may be determined as described with reference to FIG. 15A.

In an embodiment, when it is determined that the majority of the authorization requests are similar to the prior historical authorizations selected as the K neighbors are "approved," IAS 104 and 302 recommend that the authorization requests be "approved." Otherwise, the authorization requests are recommended to be "denied" or may be flagged for human intervention or further review or redirected to Medicaid or Medicare for further scrutiny. In an embodiment, it is often the case that the historical authorization data or historical authorization requests may include some noise. For example, the noise may correspond to data due to data entry errors and (occasional) errors in decision-making. In another instance, the noise may correspond to systematic errors in the data or labels due to incorrect training/understanding of the human operators. Further, there may be imperfections in the data because some of the measurements may be systematically biased (e.g., a sensor in the test instrument is faulty). As long as the errors are infrequent and consistent, they may be machine-learned, and the IAS 104 and 302 may execute operations to identify such noise. In an embodiment, the consistency may enable the operations executed by the IAS 104 and 302 to be more robust and the results of the operations (e.g., approvals, denials, or flagged for reviews or redirected to Medicaid or Medicare for further scrutiny) to be more reliable and accurate.

Figures 16, 17:
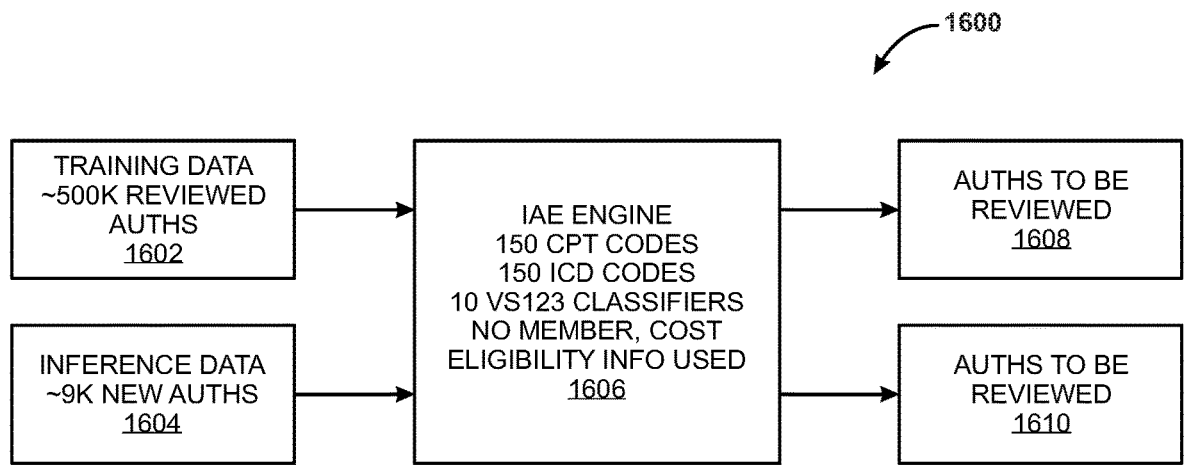
FIG. 16 is a block diagram illustrating an exemplary implementation of the IAS, according to an exemplary embodiment.
FIG. 17 is a block diagram showing an illustration of a table including the results of operations executed by the IAS, according to an exemplary embodiment.

FIG. 16 is a block diagram 1600 illustrating an exemplary implementation of the IAS, according to an exemplary embodiment. FIG. 16 is described in conjunction with FIGS. 1-4 and FIG. 10. FIG. 16 shows a block diagram 1600 illustrating an exemplary implementation of the IAS 104 and 302. In an embodiment, the IAS 104 and 302 may receive data. For example, such data may correspond to training data associated with the authorization requests (e.g., 1602) and inference data that may correspond to new authorization requests received in real-time. In an embodiment, the authorization requests may include ICD codes, CPT codes, classifiers, cost eligibility information associated with the patient member, etc. (e.g., 1606).

In an embodiment, as described in the detailed description with reference to FIGS. 2-4, the machine learning models may be trained, and the machine learning engines in the IAS 104 and 302 may execute operations. In response to the execution of the operations or functions, the IAS 104 and 302 may either automatically approve the authorization requests, deny or reject the authorization requests, or flag the authorization requests for further review (e.g., 1608, 1610). In another embodiment, IAS 104 and 302 may execute operations as described in FIG. 10. Recommendations for each service request from the authorization requests may be combined based on classifiers, and overall recommendations for the authorization request may be obtained. Typically, suppose any service from the multiple services associated with one authorization request is flagged for review or redirected to Medicaid or Medicare for further scrutiny. In that case, the IAS 104 and 302 may prompt the end user to review the other service requests associated with the authorization request. In an embodiment, the approved or denied, or flagged for review authorization requests may be displayed on a dashboard or UI, for example.

FIG. 17 is a block diagram 1700 showing an illustration of a table including results of operations executed by the IAS, according to an exemplary embodiment. FIG. 17 is described in conjunction with FIGS. 1-4 and FIG. 10. In an embodiment, FIG. 17 shows a table including the results or response to the evaluation of the authorization requests executed by IAS 104 and 302. For example, the table shows data that may be approved and flagged for review by the IAS 104 and 302 based on retrospective concurrence (or disagreement) with the human operator. Further, the table in FIG. 17 further shows results in response to the execution of operations by the IAS 104 and 302 that may include evaluation, processing and analysis, computations, transformations, etc., as described with reference to FIGS. 1-4. In an embodiment, the table in FIG. 17 also shows true approve, 1706, true deny 1708, including cascaded classifier approved 1702, classifier review 1704, etc. The IAS 104 and 302 may approve or deny the authorization requests. The authorization requests that may be denied may be flagged for a review based on attributes, parameters, or criteria associated with the classifiers, as described with reference to FIG. 10. Historically, correctly approved/reviewed service requests will improve the accuracy of the IAS 104 and 302 associated with the service requests.

Figure 18:
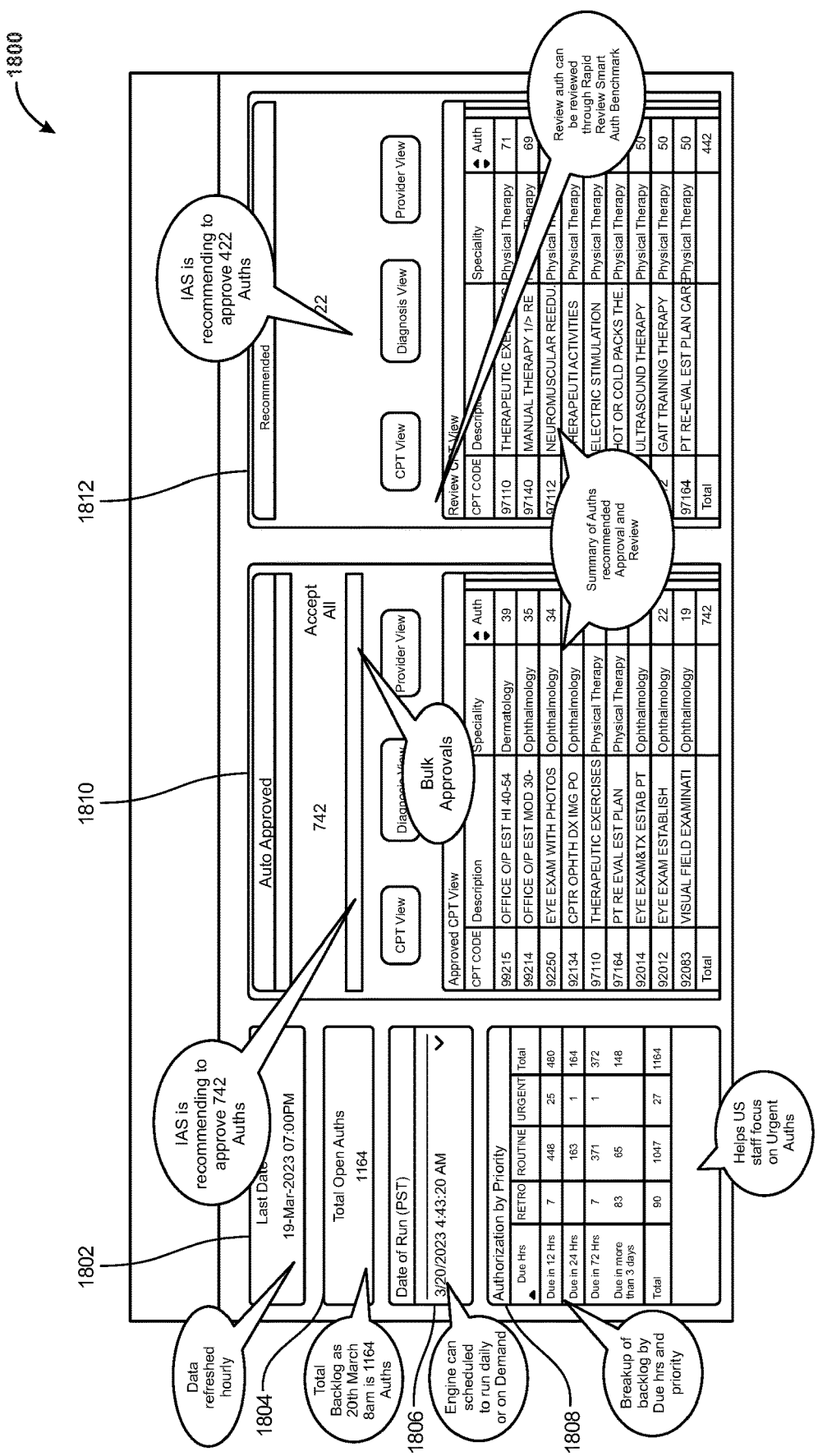
FIG. 18 is a block diagram showing an illustration of an IAS dashboard, according to an exemplary embodiment.

FIG. 18 is a block diagram 1800 showing an illustration of an IAS dashboard, according to an exemplary embodiment. FIG. 18 is described in conjunction with FIGS. 1-4. FIG. 15 is a block diagram 1800 showing an illustration of a UI or dashboard. The UI or dashboard displays results in response to the execution of the operations by the IAS 104 and 302. In an embodiment, FIG. 18 provides information on service requests that were recommended for auto-approval (e.g., 1810) and denied or flagged for review (e.g., 1812). In an embodiment, the UI or dashboard provides options for bulk approvals (e.g., 1810) to improve the productivity of the human operator. The dashboard also provides a facility for the human reviewer to override the IAS 104 and 302 recommendations. The dashboard or UI may provide additional information (e.g., 1804, 1806, 1808) that may aid or help human reviewers in the review process. For example, the dashboard may indicate the percentage of confidence associated with each recommendation; the higher confidence recommendations typically require less scrutiny from the human operator and thus provide an opportunity for a quick final disposition. Similarly, IAS 104 and 302 may indicate the urgency of recommendation (e.g., 1808 Authorizations by priority) disposition. In an embodiment, the higher priority recommendations may typically require sooner review from the human operator and thus provide an opportunity for earlier attention and disposition.

FIG. 19 is a block diagram 1900 showing an illustration of a dashboard including a detailed view of authorization requests, according to an exemplary embodiment. FIG. 19 is described in conjunction with FIGS. 1-4. FIG. 19 shows a block diagram 1900, including a dashboard or UI arranged in a table of rows (e.g., 1904) and columns (e.g., CPT Code 1906, CPT Code Description 1908, Auth No. 1910, Action 1912, Specialty 1914, Diagnosis description 1916, Member ID 1918, and HP group 1920). The human operator gets an opportunity to review individual authorization further and determine its final disposition or recommendation for further review (e.g., by a peer or a superior).

Figure 20:
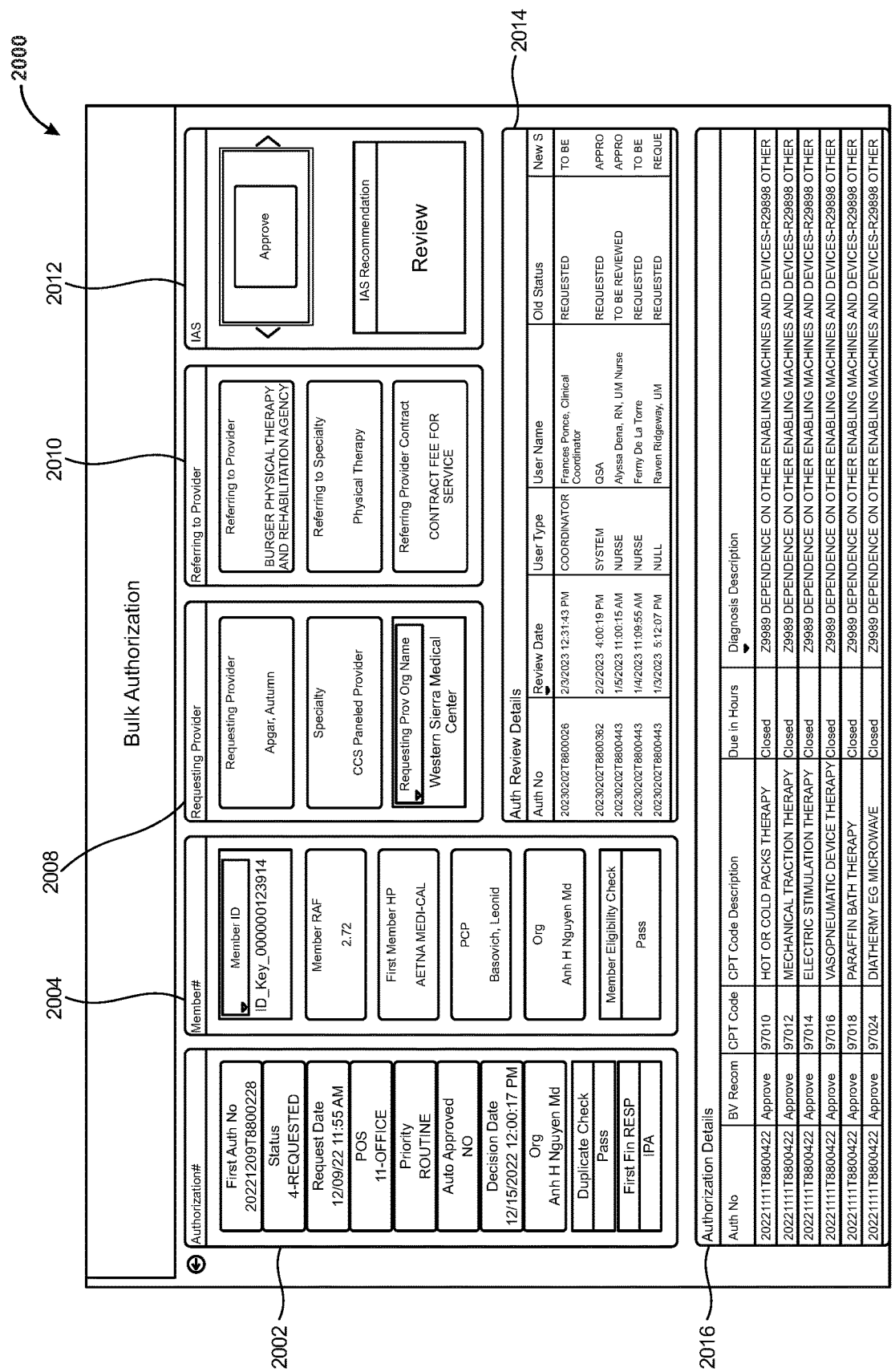
FIG. 20 is a block diagram showing an illustration of a dashboard for bulk approving multiple authorization requests, according to an exemplary embodiment.

FIG. 20 is a block diagram 2000 showing an illustration of a dashboard for bulk approving multiple authorization requests, according to an exemplary embodiment. FIG. 20 is described in conjunction with FIGS. 1-4. FIG. 18 is a block diagram 2000 showing an illustration of a dashboard or UI for bulk review of the authorization requests. In an embodiment, the authorization requests may be reviewed in bulk and flagged as approved or denied, or they may require further review/information or redirect the authorization requests to Medicaid or Medicare for further scrutiny. The bulk approval features either collective approvals of all authorizations recommended for approval or all authorizations requesting certain services. For example, the dashboard or UI in FIG. 20 shows data fields that include authorization details 2016, authorization number 2002, member ID 2004, referring to provider 2010, IAS 104 and 302 related information 2012 (e.g., reviews, approved, etc.), and auth review details 2014.

Figure 21:
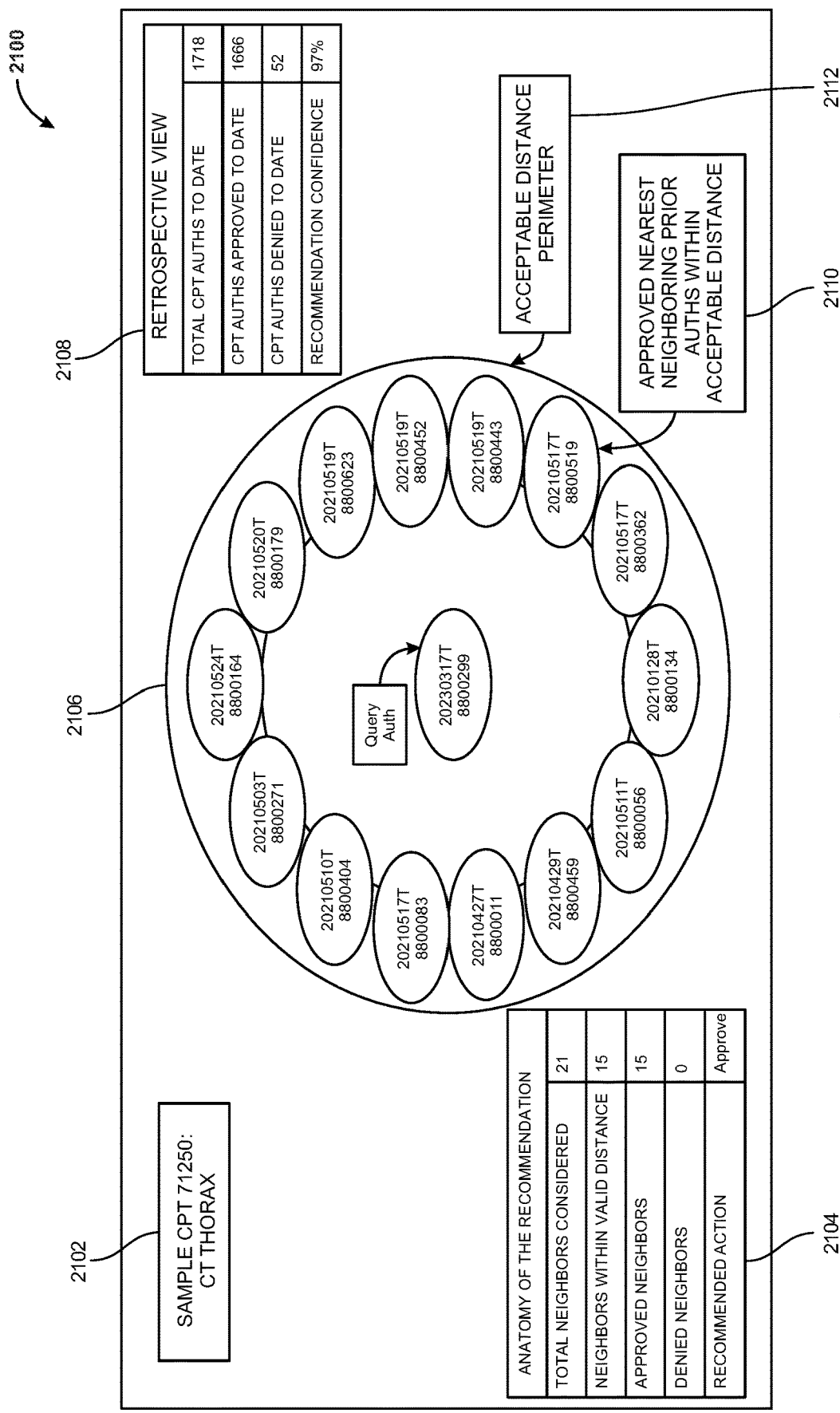
FIG. 21 is a block diagram showing an illustration of a dashboard for a detailed review of the authorization requests, according to an exemplary embodiment.

FIG. 21 is a block diagram 2100 showing an illustration of a dashboard for a detailed review of the authorization requests, according to an exemplary embodiment. FIG. 21 is described in conjunction with FIGS. 1-4. FIG. 21 illustrates a block diagram 2100 that shows a dashboard or UI. In an embodiment, FIG. 19 shows the dashboard or UI that includes a query corresponding to an authorization request associated with sample CPT 71250 that corresponds to, for example, a sample CT thorax 2102. The query shown at the center in 2106 shows approved nearest neighboring prior authorizations with an acceptable distance and acceptable distance perimeter (e.g., 2110, 2112). This feature facilitates the human operator in understanding why IAS 104 and 302 made specific recommendations or suggestions. In an embodiment, the nearest neighbors that are approved historical prior authorizations naturally support the decision of approval recommendation. The nearest neighbors that are denied historical prior authorizations naturally support the decision of review. The dashboard further shows data or information related to the anatomy of recommendation 2104, retrospective view 2108, etc. For example, the anatomy of the recommendation 2104 dashboard element shows quantitative details of the neighborhood analysis executed by the IAS 104 and 302. The retrospective view 2108 dashboard element displays confidence the IAS 104 and 302 have in the recommendation based on the accuracy of historical decisions for that specific service request.

Figure 22:
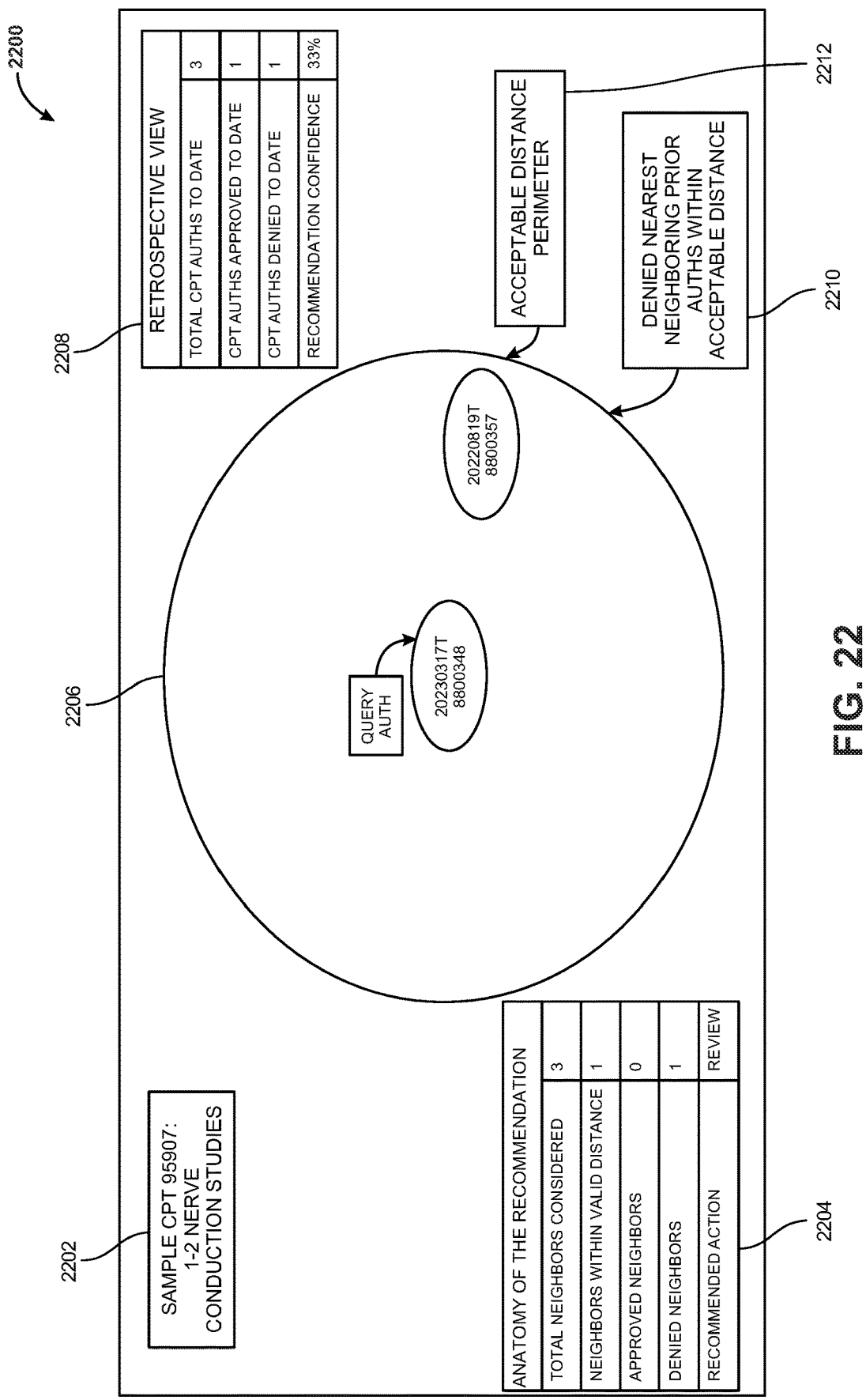
FIG. 22 is a block diagram showing an illustration of a dashboard for a detailed review by a human operator, according to an exemplary embodiment.

FIG. 22 is a block diagram 2200 showing an illustration of a dashboard for a detailed review by a human operator, according to an exemplary embodiment. FIG. 22 is described in conjunction with FIGS. 1-4. FIG. 22 shows a block diagram 2200, including a dashboard or UI. In an embodiment, the dashboard or UI displays a query corresponding to an authorization request associated with sample CPT 95907 that corresponds to 1-2 nerve conduction studies 2202. The query auth flagged at the center of 2206 includes other denied nearest neighboring prior authorizations within acceptable distance and acceptable distance perimeter (e.g., 2210, 2212). The dashboard further shows data or information related to the anatomy of recommendation 2204, retrospective view 2208, etc. For example, the anatomy of the recommendation 2204 dashboard element shows quantitative details of the neighborhood processing and analysis executed by the IAS 104 and 302. The retrospective view 2208 dashboard element displays confidence the IAS 104 and 302 have in the recommendation based on the accuracy of historical decisions for that specific service request.

Figure 23:
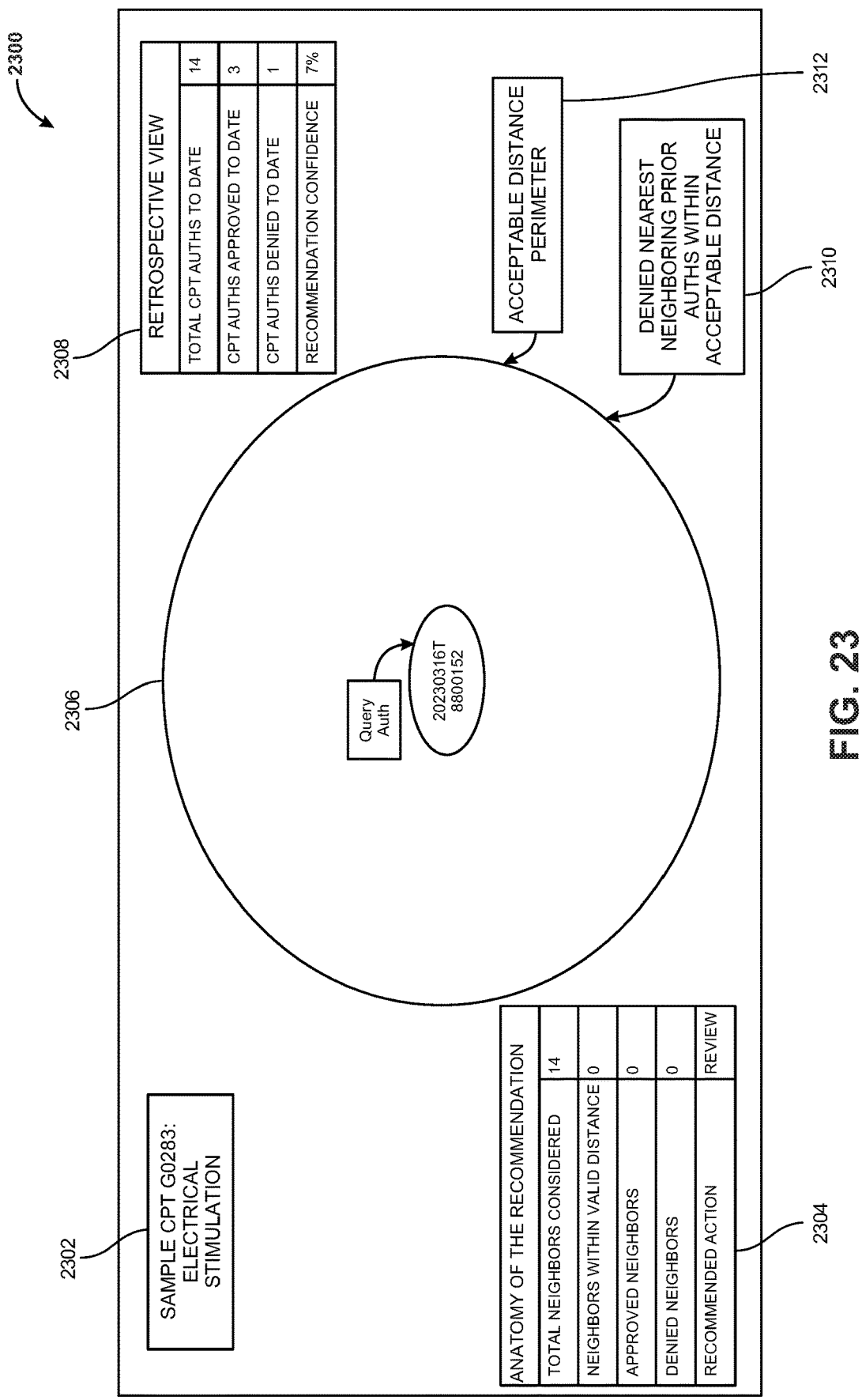
FIG. 23 is a block diagram illustrating a dashboard for a detailed review by a human operator, according to an exemplary embodiment.

FIG. 23 is a block diagram 2300 illustrating a dashboard for a detailed review by a human operator, according to an exemplary embodiment. FIG. 23 is described in conjunction with FIGS. 1-4. FIG. 23 shows a block diagram 2300, including a dashboard or UI that displays a query corresponding to an authorization request associated with sample CPT G0283 that corresponds to 1-2 Electrical Stimulation 2302. The query auth flagged at the center of 2306, including the other denied nearest neighboring prior authorizations within acceptable distance and acceptable distance perimeter (e.g., 2310, 2312). The dashboard further shows data or information related to the anatomy of recommendation 2304, retrospective view 2308, etc. For example, the anatomy of the recommendation 2304 dashboard element shows quantitative details of the neighborhood processing and analysis executed by the IAS 104 and 302. The retrospective view 2308 dashboard element displays confidence the IAS 104 and 302 have in the recommendation based on the accuracy of historical decisions for that specific service request.

Figure 24A:
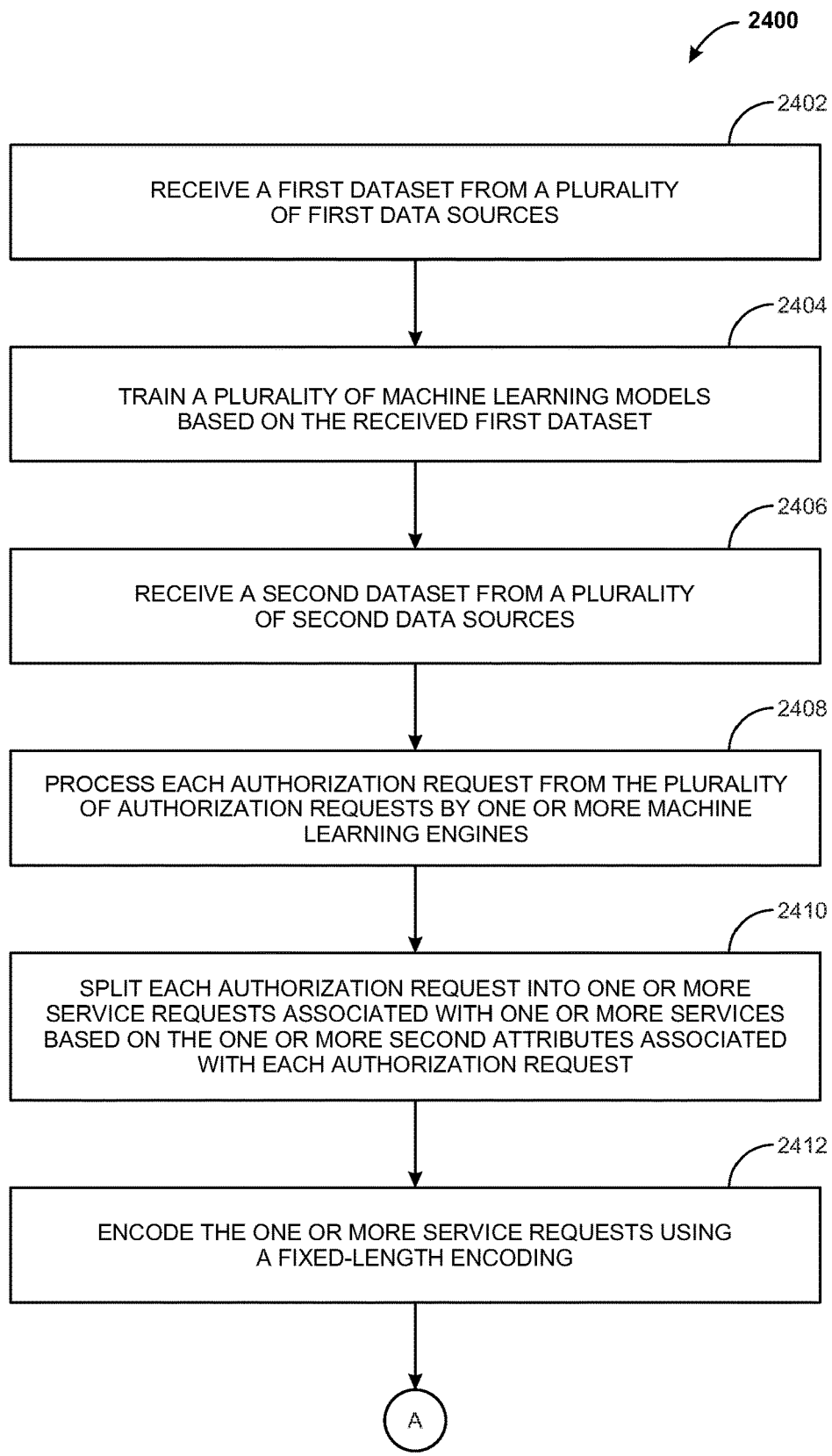
FIGS. 24A and 24B are flow diagrams showing a process for authorizing requests, according to an exemplary embodiment.
Figure 24B:
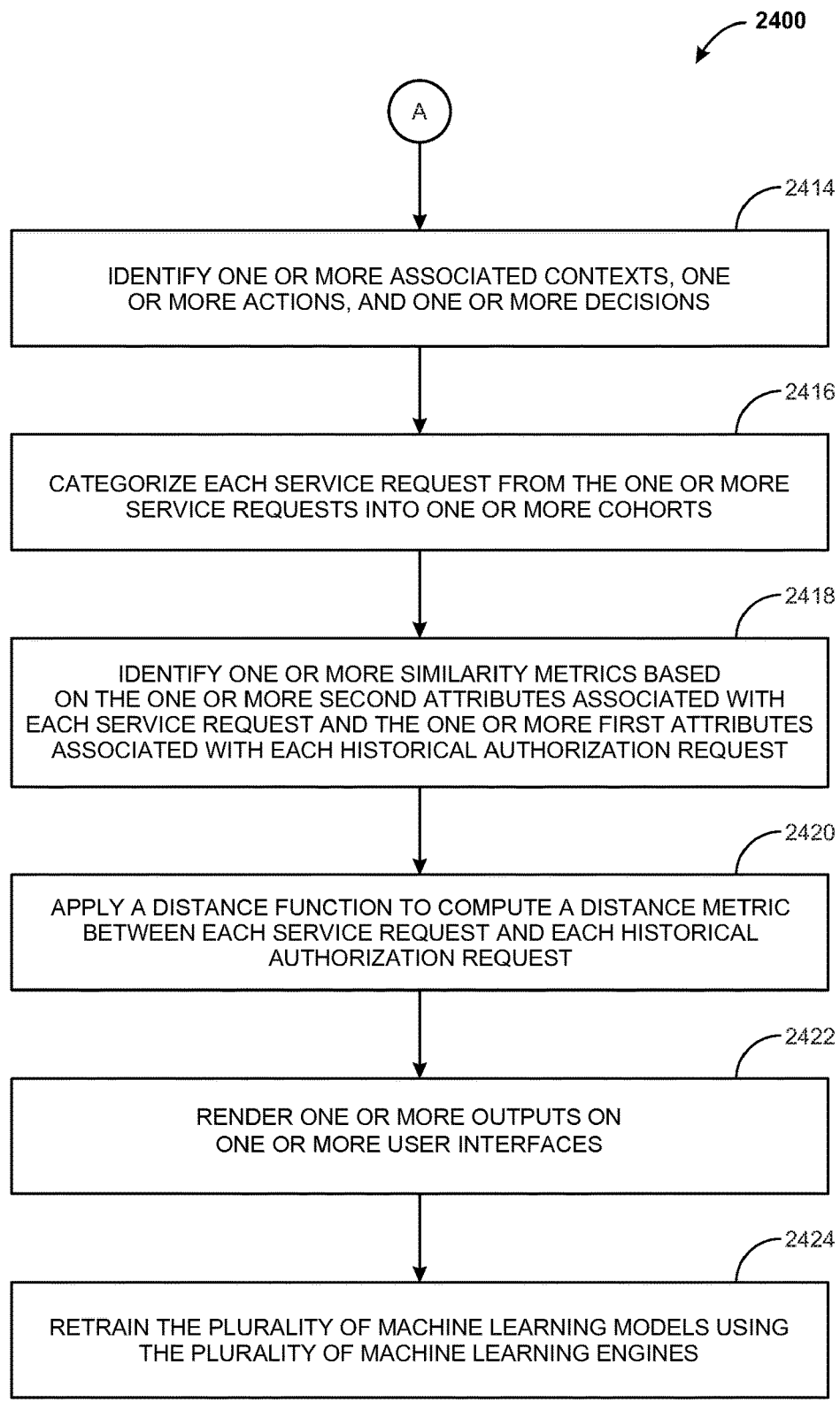

FIGS. 24A and 24B are flow diagrams showing process 2400 for authorizing requests, according to an exemplary embodiment. FIGS. 24A and 24B are described in conjunction with FIGS. 1-4. FIGS. 24A and 24B are illustrations showing a process 2400 to authorize requests. Each step in process 2400 is implemented or executed by corresponding machine learning engines as described with reference to FIG. 4. In an embodiment, the following described process steps of process 2400 may be implemented by the IAS 104 and 302.

At step 2402, a first dataset from multiple first data sources are received. For instance, the first dataset includes multiple historical authorizations associated with one or more medical claims. Each historical authorization request may consist of multiple attributes or parameters, for example, one or more first attributes. At step 2404, multiple machine learning engines train multiple machine learning models. For instance, the multiple machine learning models may be trained by the multiple machine learning engines based on the received first dataset. At step 2406, a second dataset from multiple secondary data sources is received. In an embodiment, the second dataset may include multiple authorization requests that may be received in real-time and may be associated with medical claims related to medical procedures, treatments, medications, hospital stays, etc. The authorization requests received in real-time may consist of multiple attributes or parameters, such as second attributes.

At step 2408, each authorization request received in real-time is processed or analyzed. For instance, based on the trained machine learning models, each authorization request received in real-time may be processed or analyzed by the multiple machine learning engines in the IAS 104 and 302, as shown and described with reference to FIGS. 1-4. At step 2410, each authorization request is split into multiple service requests. For instance, each authorization request is split or partitioned into multiple service requests based on one or more second attributes. In an embodiment, the splitting may be performed using a specialized request parsing module implemented on a field-programmable gate array (FPGA). The one or more second attributes may include identifiers associated with one or more services that may be related to medical procedures, treatments, medications, hospital stays, etc. At step 2412, each service request is encoded using a fixed-length encoding. The fixed-length encoding may assign a unique numeric identifier based on the presence of a categorical variable. In an embodiment, the encoding may be performed using a dedicated encoding processor optimized for fast encoding operation. At step 2414, one or more associated contexts, one or more actions, and one or more decisions may be identified or determined. For instance, for each encoded service request, the above-described parameters may be determined by applying the trained machine learning models to compare the first attributes associated with each authorization request with the second attributes associated with each authorization request in real-time. For example, the first attributes associated with the historical authorization requests may be compared with the second attributes associated with the authorization requests received in real-time. In an embodiment, the machine learning models may be executed on specialized machine learning accelerators comprising tensor processing units (TPUs) or GPUs for high-performance parallel processing.

At step 2416, each service request is categorized into one or more cohorts. In an embodiment, categorizing the service requests into one or more cohorts may include execution of the following steps: At step 2418, one or more similarity metrics between the historical authorization requests and the authorization requests received in real-time. One or more second attributes are associated with each service request. In an embodiment, one or more second attributes are associated with each authorization request received in real-time, and when the authorization requests received in real-time are split into multiple service requests, one or more second attributes are associated with each service request. In an embodiment, the similarity metrics are computed using a custom similarity calculation engine implemented on an application-specific integrated circuit (ASIC).

At step 2420, a distance function is applied to compute the distance metric or distance between each service request and each historical request. The above-described computations are performed based on the determined one or more similarity metrics. In an embodiment, the distance function-based computations may be accelerated by a graphics processing unit (GPU) optimized for parallel distance calculations. Upon performing the computations, one or more service requests may be categorized into one or more cohorts. In an embodiment, the categorization function or operation may be executed on a distributed computing framework tailored for large-scale data processing. At step 2422, one or more outputs are rendered on one or more user interfaces. In an embodiment, one or more outputs are based on the processing of the one or more categorized service requests that may be categorized and associated with one or more authorization requests. In an embodiment, one or more outputs consist of an approval of one or more service requests, a rejection of one or more service requests, or flagging of one or more service requests for review or redirecting the authorization requests to Medicaid or Medicare for further scrutiny. At step 2424, the multiple machine learning models are retrained by the multiple machine learning engines in response to one or more outputs.

In an embodiment, the system and method described above may provide a transformative approach to medical claim authorization, introducing a range of technical advantages that revolutionize the process. The IAS 104 and 302 execute operations that may include, for example, analyzing vast and complex datasets, allowing the uncovering of subtle patterns indicative of fraudulent activity that would go unnoticed by human auditors. This heightened fraud detection capability safeguards resources and ensures funds are used for legitimate medical expenses. Beyond accuracy, the IAS 104 and 302 improve efficiency by automating routine authorization requests. This not only reduces claim processing times but also frees up skilled staff to focus their expertise on complex or high-risk cases.

The machine learning engines and machine learning models ensure consistency in the application of authorization rules and criteria, fostering greater transparency and fairness. The machine learning models continuously learn from historical data and new patterns, resulting in steadily increasing accuracy and minimizing the likelihood of incorrect authorization requests. In an embodiment, the IAS 104 and 302's capacity for trend analysis offers invaluable insights into service utilization, pinpointing potential areas of fraud and highlighting opportunities for optimizing healthcare delivery processes. The predictive analytics operations executed by the IAS 104 and 302 may empower the providers and insurers to anticipate claim outcomes, guiding them in strategic resource allocation and proactive problem-solving for an increasingly streamlined and cost-effective system overall.

In an embodiment, the system method described above that implements the IAS 104 and 302 in a hospital ecosystem may provide several technical advantages, such as improved productivity and improved accuracy of the authorization requests. Further technical advantages of the IAS 104 and 302 include the ability to process large volumes of data, detect patterns, and make accurate predictions. In an embodiment, the IAS 104 and 302 may provide or facilitate a mechanism for data analysis and Pattern Recognition. For instance, machine learning engines and machine learning models may analyze vast amounts of historical data related to medical claims. The machine learning engines in the IAS 104 and 302 may identify patterns and correlations that might not be immediately apparent to human reviewers. By recognizing patterns in past authorization decisions and outcomes, machine learning models may make more informed predictions about the likelihood of approval for new requests.

In an embodiment, the system and method described above may provide or facilitate real-time decision-making. The machine learning models may process authorization requests in real-time, providing instant decisions based on the information available. This rapid processing enables faster responses to patients and healthcare providers, improving overall efficiency in the authorization requests process. In an embodiment, the IAS 104 and 302 may facilitate scalability. For example, Machine learning models may scale to handle a large volume of authorization requests efficiently. As the number of claims or authorization requests increases, the IAS 104 and 302 may adapt and continue to provide timely responses without experiencing significant slowdowns or bottlenecks.

In an embodiment, the system and method described above may provide adaptability and learning. For example, one of the key advantages of machine learning engines and models is their ability to learn and adapt over time. As new data becomes available, machine learning engines and models may continuously refine their techniques or mechanisms to improve accuracy and effectiveness. This adaptability ensures that the authorization process remains up to date with evolving medical practices and guidelines.

In an embodiment, the system and method described above may provide or facilitate reduced error rates. For instance, by automating the authorization of the request process, the machine learning engines in the IAS 104 and 302 may reduce human error rates associated with manual review. While human reviewers may overlook certain patterns or factors, the training of the machine learning models by the machine learning engines in the IAS 104 and 302 is designed to be consistent and thorough in analysis, leading to more accurate decision-making. In an embodiment, the system and method described above may provide or facilitate fraud detection. For example, machine learning models may be trained to detect patterns indicative of fraudulent claims, such as unusual billing practices or inconsistencies in medical records. By flagging potentially fraudulent requests, the machine learning models may help prevent financial losses and maintain the integrity of the claims processing system. The machine learning engine and the machine learning model's strength lies in their ability to analyze large volumes of datasets, detecting subtle patterns and anomalies that would be near-impossible for humans to spot. This helps identify fraudulent claims like duplicate billing, upcoding (billing for more expensive procedures than were performed), phantom billing (claims for services that were never provided), or unusual service combinations.

In an embodiment, the system and method described above may provide or facilitate customization and personalization. For instance, the machine learning engines and the machine learning models may be customized to suit the specific needs and preferences of healthcare organizations. By incorporating factors such as patient history, treatment guidelines, and provider preferences, these machine learning models may tailor authorization decisions to individual cases, ensuring more personalized care. In an embodiment, the use of machine learning engines and machine learning models in authorizing medical claims offers significant technical advantages, including improved efficiency, accuracy, scalability, and adaptability. By harnessing the power of data and automation, the IAS 104 and 302 may transform the claims authorization process and enhance the quality of healthcare delivery.

In an embodiment, the IAS 104 and 302 may reduce the volume of authorization requests that need review from a human operator by automatically approving the authorization requests that meet specific criteria. The authorization requests may be analyzed in multiple dimensions by machine learning models, machine learning engines, etc., based on multidimensional contexts (e.g., based on patient history, service provider history, trust score associated with the providers, etc.) and prioritize authorizations thereby reducing the likelihood of the authorization denials. The IAS may enable faster approvals of authorization requests and improve the identification of cases that may be denied due to accidental or overlooked practices. In an embodiment, by identifying the denied authorization requests and providing accurate data insights, a healthy industry-standard denial rate may be maintained.

Figure 25:
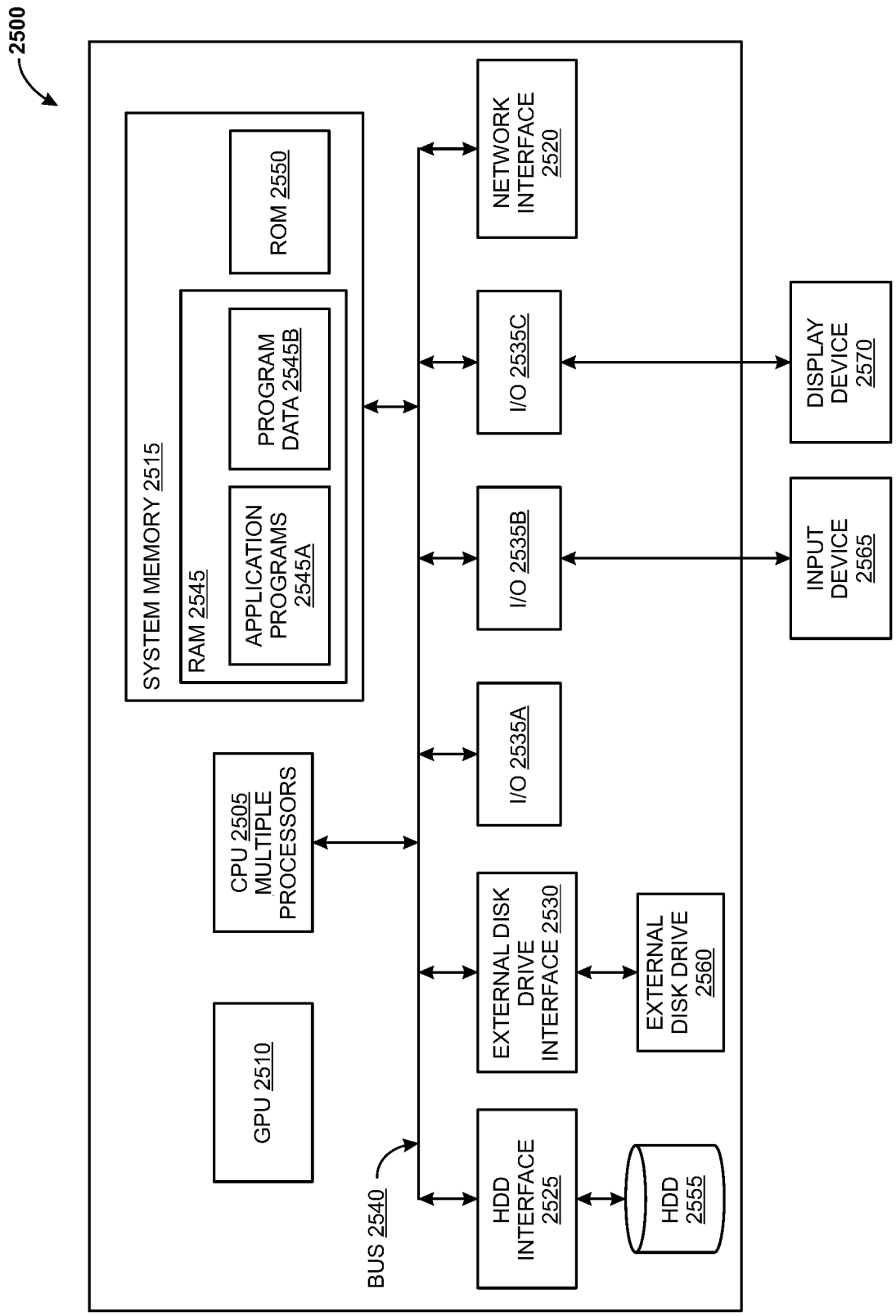
FIG. 25 shows an exemplary hardware configuration of a computer that may implement components of an intelligent authorization system, according to exemplary embodiments.

FIG. 25 shows an exemplary hardware configuration of computer 2500 that may be used to implement components of an intelligent authorization system, in accordance with exemplary embodiments. The computer 2500 is shown in FIG. 25 includes CPU 2505, GPU 2510, system memory 2515, network interface 2520, hard disk drive (HDD) interface 2525, external disk drive interface 2530, and input/output (I/O) interfaces 2535A, 2535B, 2535C. These elements of the computer are coupled to each other via system bus 2540. The CPU 2505 may perform arithmetic, logic, and/or control operations by accessing system memory 2515. The CPU 2505 may implement the processors of the exemplary devices and/or systems described above. The GPU 2510 may perform operations for processing graphic or AI tasks. In case computer 2500 is used to implement an exemplary central processing device, GPU 2510 may be GPU 2510 of the exemplary central processing device as described above. The computer 2500 does not necessarily include GPU 2510, for example, in case computer 2500 is used for implementing a device other than a central processing device. The system memory 2515 may store information and/or instructions for use in combination with the CPU 2505. The system memory 2515 may include volatile and non-volatile memory, such as random-access memory (RAM) 2545 and read-only memory (ROM) 2550. A basic input/output system (BIOS) containing the basic routines that help to transfer information between elements within the computer 2500, such as during start-up, may be stored in ROM 2550. The system bus 2540 may be any of several types of bus structures, including a memory bus or memory controller, a peripheral bus, and a local bus using any of a variety of bus architectures.

The computer may include a network interface 2520 for communicating with other computers and/or devices via a network.

Further, the computer may include a hard disk drive (HDD) 2555 for reading from and writing to a hard disk (not shown) and an external disk drive 2560 for reading from or writing to a removable disk (not shown). The removable disk may be a magnetic disk for a magnetic disk drive or an optical disk such as a CD ROM for an optical disk drive. The HDD 2555 and external disk drive 2560 are connected to the system bus 2540 by HDD interface 2525 and external disk drive interface 2530, respectively. The drives and their associated non-transitory computer-readable media provide non-volatile storage of computer-readable instructions, data structures, program modules, and other data for the general-purpose computer. The relevant data may be organized in a database, such as a relational or object database.

Although the exemplary environment described herein employs a hard disk (not shown) and an external disk (not shown), it should be appreciated by those skilled in the art that other types of computer-readable media which may store data that is accessible by a computer, such as magnetic cassettes, flash memory cards, digital video disks, random access memories, read-only memories, and the like, may also be used in the exemplary operating environment.

Several program modules may be stored on the hard disk, external disk, ROM 2550, or RAM 2545, including an operating system (not shown), one or more application programs 2545A, other program modules (not shown), and program data 2545B. The application programs may include at least some of the functionality described above.

The computer 2500 may be connected to input device 2565, such as mouse and/or keyboard, and display device 2570, such as liquid crystal display, via corresponding I/O interfaces 2535A to 2535C and the system bus 2540. In addition to an implementation using a computer 2500, as shown in FIG. 25, part or all of the functionality of the exemplary embodiments described herein may be implemented as one or more hardware circuits. Examples of such hardware circuits may include but are not limited to Large Scale Integration (LSI), Reduced Instruction Set Circuits (RISC), Application Specific Integrated Circuit (ASIC), and Field Programmable Gate Arrays (FPGA).

One or more embodiments are now described with reference to the drawings, wherein reference numerals refer to elements throughout. Numerous specific details are set forth in the following description to provide a thorough understanding of the various embodiments. It is evident, however, that the various embodiments may be practiced without these specific details (and without applying them to any networked environment or standard).

As used in this application, in some embodiments, the terms "component," "system," and the like are intended to refer to, or comprise, a computer-related entity or an entity related to an operational apparatus with one or more specific functionalities, wherein the entity may be either hardware, a combination of hardware and software, software, or software in execution. As an example, a component may be, but is not limited to, a process running on a processor, a processor, an object, an executable, a thread of execution, computer-executable instructions, a program, and/or a computer. By way of illustration and not limitation, both an application running on a server and the server may be a component.

The above descriptions and illustrations of embodiments, including what is described in the Abstract, are not intended to be exhaustive or to limit one or more embodiments to the precise forms disclosed. While specific embodiments of, and examples for, one or more embodiments are described herein for illustrative purposes, various equivalent modifications are possible within the scope, as those skilled in the relevant art will recognize. These modifications may be made considering the above-detailed description. Rather, the scope is to be determined by the following claims, which are to be interpreted in accordance with established doctrines of claim construction.

What is claimed is:

1. A system to authorize requests associated with medical claims, comprising:
   a processor;
   a memory storing instructions which, when executed by the processor, causes the system to execute operations, to:
   receive a first dataset from a plurality of first data sources, wherein the first dataset includes a plurality of historical authorization requests associated with one or more medical claims, wherein each historical authorization request from the plurality of historical authorization requests consists of one or more first attributes;
   using a plurality of machine learning engines, train a plurality of machine learning models based on the received first dataset, wherein the training includes adjusting weights of one or more nodes in the machine learning models based on patterns detected in the first dataset;
   receive a second dataset from a plurality of second data sources, wherein the second dataset includes a plurality of authorization requests in real-time and is associated with the one or more medical claims related to one or more medical procedures, one or more treatments, one or more medications, one or more hospital stays, or a combination thereof, wherein each authorization request from the plurality of authorization requests in real-time consists of one or more second attributes;

based on the trained plurality of machine learning models, process each authorization request from the plurality of authorization requests by one or more machine learning engines, by:

splitting each authorization request into one or more service requests based on the one or more second attributes, wherein the one or more second attributes include identifiers associated with one or more services;

encoding the one or more service requests using a fixed-length encoding, wherein the fixed-length encoding assigns a unique numeric identifier based on a categorical variable; and for each encoded service request, identifying one or more associated contexts, one or more actions, and one or more decisions by applying the trained machine learning models to compare the one or more first attributes associated with each historical request and the one or more second attributes associated with each authorization request in real-time;

categorize each service request from the one or more service requests into one or more cohorts, by:

for each service request, identifying one or more similarity metrics based on the one or more second attributes associated with each service request and the one or more first attributes associated with each historical authorization request;

based on the identified one or more similarity metrics, applying a distance function to compute a distance metric between each service request and each historical authorization request; and categorizing the one or more service requests into the one or more cohorts based on the computation;

render one or more outputs associated with the one or more service requests on one or more user interfaces, wherein the one or more outputs are based on the processing of the one or more categorized service requests, wherein the one or more service requests correspond to the one or more authorization requests; and in response to rendering the one or more outputs, retrain the plurality of trained machine learning models using the plurality of machine learning engines by adjusting the weights of the one or more nodes in the machine learning models.

2. The system of claim 1, wherein the one or more service requests are encoded using one-hot encoding.

3. The system of claim 1 further comprises: processing the one or more service requests based on a plurality of classifiers, wherein the plurality of classifiers includes one or more of eligibility, coverage, medical necessity, trust model, cost, or a combination thereof.

4. The system of claim 1, wherein the one or more outputs consist of an approval of the one or more service requests, a rejection of the one or more service requests, an audit of the one or more service requests for a review, and a redirection of the one or more service requests for a review by one or more of a Medicare or Mediclaim.

5. The system of claim 1, further comprising:
render a plurality of visualizations corresponding to the one or more outputs on the one or more user interfaces;
receive one or more inputs via the one or more user interfaces; and
based on the received inputs, modify the plurality of visualizations rendered on the one or more user interfaces.

6. The system of claim 1, further comprising:
create one or more forecasts corresponding to the one or more authorization requests received in real-time based on patterns associated with the plurality of historical authorization requests; and
based on the created one or more forecasts, identify one or more trends and one or more correlations between the one or more authorization requests received in real-time and the plurality of historical authorization requests.

7. The system of claim 1, further comprising:
compute a trust score for each of one or more providers and one or more groups of providers, and
classify the one or more providers and the one or more groups of providers based on computed trust score.

8. A method to authorize requests associated with medical claims, comprising:
receiving a first dataset from a plurality of first data sources, wherein the first dataset includes a plurality of historical authorization requests associated with one or more medical claims, wherein each historical authorization request from the plurality of historical authorization requests consists of one or more first attributes;

using a plurality of machine learning engines, training a plurality of machine learning models based on the received first dataset, wherein the training includes adjusting weights of one or more nodes in the machine learning models based on patterns detected in the first dataset;

receiving a second dataset from a plurality of second data sources, wherein the second dataset includes a plurality of authorization requests in real-time and is associated with the one or more medical claims related to one or more medical procedures, one or more treatments, one or more medications, one or more hospital stays, or a combination thereof, wherein each authorization request from the plurality of authorization requests in real-time consists of one or more second attributes;

based on the trained plurality of machine learning models, processing each authorization request from the plurality of authorization requests by one or more machine learning engines, by:

splitting each authorization request into one or more service requests based on the one or more second attributes, wherein the one or more second attributes include identifiers associated with one or more services;

encoding the one or more service requests using a fixed-length encoding, wherein the fixed-length encoding assigns a unique numeric identifier based on a categorical variable; and for each encoded service request, identifying one or more associated contexts, one or more actions, and one or more decisions by applying the trained machine learning models to compare the one or more first attributes associated with each historical request and the one or more second attributes associated with each authorization request in real-time;

categorizing each service request from the one or more service requests into one or more cohorts, by:

for each service request, identifying one or more similarity metrics based on the one or more second attributes associated with each service request and the one or more first attributes associated with each historical authorization request;

based on the identified one or more similarity metrics, applying a distance function to compute a distance metric between each service request and each historical authorization request; and categorizing the one or more service requests into the one or more cohorts based on the computation;

rendering one or more outputs associated with the one or more service requests on one or more user interfaces, wherein the one or more outputs are based on the processing of the one or more categorized service requests, wherein the one or more service requests correspond to the one or more authorization requests; and in response to rendering the one or more outputs, retraining the plurality of trained machine learning models using the plurality of machine learning engines by adjusting the weights of the one or more nodes in the machine learning models.

9. The method of claim 8, wherein the one or more service requests are encoded using one-hot encoding.

10. The method of claim 8, further comprises: processing the one or more service requests based on a plurality of classifiers, wherein the plurality of classifiers includes one or more of eligibility, coverage, medical necessity, trust model, cost, or a combination thereof.

11. The method of claim 8, wherein the one or more outputs consists of an approval of the one or more service requests, a rejection of the one or more service requests, an audit of the one or more service requests for a review, and a redirection of the one or more service requests for a review by one or more of a Medicare or Mediclaim.

12. The method of claim 8, further comprises:

rendering a plurality of visualizations corresponding to the one or more outputs rendered on the one or more user interfaces;

receiving one or more inputs via the one or more user interfaces; and based on the received inputs, modifying the plurality of visualizations on the one or more user interfaces.

13. The method of claim 8, further comprises:

creating one or more forecasts corresponding to the one or more authorization requests received in real-time based on patterns associated with the plurality of historical authorization requests; and based on the created one or more forecasts, identifying one or more trends and one or more correlations between the one or more authorization requests received in real-time and the plurality of historical authorization requests.

14. The method of claim 8, further comprises:

computing a trust score for each of one or more providers and one or more groups of providers; and classifying the one or more providers and the one or more groups of providers based on computed trust score.

15. A non-transitory computer-readable device having instructions stored thereon that, when executed by at least one computing device, cause the at least one computing device to perform operations comprising:

receiving a first dataset from a plurality of first data sources, wherein the first dataset includes a plurality of historical authorization requests associated with one or more medical claims, wherein each historical authorization request from the plurality of historical authorization requests consists of one or more first attributes;

using a plurality of machine learning engines, training a plurality of machine learning models based on the received first dataset, wherein the training includes adjusting weights of one or more nodes in the machine learning models based on patterns detected in the first dataset;

receive a second dataset from a plurality of second data sources, wherein the second dataset includes a plurality of authorization requests in real-time and is associated with the one or more medical claims related to one or more medical procedures, one or more treatments, one or more medications, one or more hospital stays, or a combination thereof, wherein each authorization request from the plurality of authorization requests in real-time consists of one or more second attributes;

based on the trained plurality of machine learning models, processing each authorization request from the plurality of authorization requests by one or more machine learning engines, by:

splitting each authorization request into one or more service requests based on the one or more second attributes, wherein the one or more second attributes include identifiers associated with one or more services;

encoding the one or more service requests using a fixed-length encoding, wherein the fixed-length encoding assigns a unique numeric identifier based on a categorical variable; and for each encoded service request, identifying one or more associated contexts, one or more actions, and one or more decisions by applying the trained machine learning models to compare the one or more first attributes associated with each historical request and the one or more second attributes associated with each authorization request in real-time; categorizing each service request from the one or more service requests into one or more cohorts, by:

for each service request, identifying one or more similarity metrics based on the one or more second attributes associated with each service request and the one or more first attributes associated with each historical authorization request;

based on the identified one or more similarity metrics, applying a distance function to compute a distance metric between each service request and each historical authorization request; and categorizing the one or more service requests into the one or more cohorts based on the computation;

rendering one or more outputs associated with the one or more service requests on one or more user interfaces, wherein the one or more outputs are based on the processing of the one or more categorized service requests, wherein the one or more service requests correspond to the one or more authorization requests; and in response to rendering the one or more outputs, retraining the plurality of trained machine learning models using the plurality of machine learning engines by adjusting the weights of the one or more nodes in the machine learning models.

16. The non-transitory computer-readable device of claim 15, wherein the one or more service requests are encoded using one-hot encoding.

17. The non-transitory computer-readable device of claim 15 further comprises:

processing the one or more service requests based on a plurality of classifiers, wherein the plurality of classifiers includes one or more of eligibility, coverage, medical necessity, trust model, cost, or a combination thereof.

18. The non-transitory computer-readable device of claim 15, wherein the one or more outputs consists of an approval of the one or more service requests, a rejection of the one or more service requests, an audit of the one or more service requests for a review, and a redirection of the one or more service requests for a review by one or more of a Medicare or Mediclaim.

19. The non-transitory computer-readable device of claim 15, further comprising:
   rendering a plurality of visualizations corresponding to the one or more outputs rendered on the one or more user interfaces;
   receiving one or more inputs via the one or more user interfaces; and
   based on the received inputs, modifying the plurality of visualizations on the one or more user interfaces.

20. The non-transitory computer-readable device of claim 15, further comprising:
   creating one or more forecasts corresponding to the one or more authorization requests received in real-time based on patterns associated with the plurality of historical authorization requests; and
   based on the created one or more forecasts, identifying one or more trends and one or more correlations between the one or more authorization requests received in real-time and the plurality of historical authorization requests.

* * * * *